US012584181B2

(12) United States Patent
Grant et al.

(10) Patent No.: US 12,584,181 B2
(45) Date of Patent: Mar. 24, 2026

(54) **DETECTION OF *MYCOBACTERIUM* SPECIES**

(71) Applicant: The Queen's University of Belfast, Belfast (GB)

(72) Inventors: Irene Grant, Belfast (GB); Antonio Foddai, Belfast (GB)

(73) Assignee: THE QUEEN'S UNIVERSITY OF BELFAST, Belfast (GB)

( * ) Notice: Subject to any disclaimer, the term of this patent is extended or adjusted under 35 U.S.C. 154(b) by 1037 days.

(21) Appl. No.: 17/754,091

(22) PCT Filed: Sep. 23, 2020

(86) PCT No.: PCT/EP2020/076632
§ 371 (c)(1),
(2) Date: Mar. 23, 2022

(87) PCT Pub. No.: WO2021/058606
PCT Pub. Date: Apr. 1, 2021

(65) Prior Publication Data
US 2023/0340617 A1      Oct. 26, 2023

(30) Foreign Application Priority Data
Sep. 23, 2019    (GB) ..................................... 1913705

(51) Int. Cl.
C12Q 1/68      (2018.01)
C12N 1/205      (2026.01)
C12Q 1/689      (2018.01)
C12R 1/32      (2006.01)

(52) U.S. Cl.
CPC ............. C12Q 1/689 (2013.01); C12N 1/205 (2021.05); *C12R 2001/32* (2021.05)

(58) Field of Classification Search
None
See application file for complete search history.

(56) References Cited

FOREIGN PATENT DOCUMENTS

| WO | WO-2013142003 A1 * | 9/2013 | ............... C12Q 1/04 |
| WO | WO2015015472 A1 | 2/2015 | |
| WO | WO-2015049516 A1 * | 4/2015 | ........... C12Q 1/6806 |
| WO | WO2018102350 A1 | 6/2018 | |

OTHER PUBLICATIONS

Stratmann (Journal of Clinical Microbiology, Nov. 2002, p. 4244-4250) (Year: 2002).*
Foddai (Journal of Applied Microbiology 122, 1357-1367 © 2017) (Year: 2017).*
Grant (Grant, I.R., Stewart, L.D. (2015) . . . In: Cunha, M., Inácio, J. (eds) Veterinary Infection Biology: Molecular Diagnostics and High-Throughput Strategies. Methods in Molecular Biology, vol. 1247. Humana Press, New York, NY. https://doi.org/10.1007/978-1-4939-2004-4_11) pp. 153-161 (Year: 2015).*
Muzard. small 2012, 8, No. 15, 2403-2411 (Year: 2012).*
Arutyunov,D, et al. Mycobacteriophage cell binding proteins for the capture of mycobacteria. Bacteriophage. 2014;4(4):e960346. Published Dec. 16, 2014. doi:10.4161/21597073.2014.960346.
Brovko, Lubov Y., et al., Bacteriophages for Detection and Control of Bacterial Pathogens in Food and Food-Processing Environment, In: "Advances in Food and Nutrition Research vol. 67", Jan. 1, 2012 (Jan. 1, 2012), Elsevier, XP055192905, ISSN: 1043-4526, ISBN: 978-0-12-394598-3, vol. 67, pp. 241-288, DOI: 10.1016/B978-0-12-394598-3.00006-X.
Calabrese, F, et al., Phage-coated paramagnetic beads as selective and specific capture system for biosensor applications, 2015 XVIII AISEM Annual Conference, IEEE, Feb. 3, 2015 (Feb. 3, 2015), pp. 1-4, XP032751430, DOI: 10.1109/AISEM.2015.7066851.
Smartt, Abby E., et al., Bacteriophage reporter technology for sensing and detecting microbial targets. Anal Bioanal Chem. May 2011;400(4):991-1007. doi: 10.1007/s00216-010-4561-3. Epub Dec. 17, 2010. PMID: 21165607.
Smartt, Abby E., et al., Pathogen detection using engineered bacteriophages, Analytical and Bioanalytical Chemistry, Springer, Berlin, DE, vol. 402, No. 10, Nov. 20, 2011 (Nov. 20, 2011), pp. 3127-3146, XP035029168, ISSN: 1618-2650, DOI: 10.1007/S00216-011-5555-5.
Stratmann J, et al., Development of a peptide-mediated capture PCR for detection of *Mycobacterium avium* subsp. paratuberculosis in milk, Journal of Clinical Microbiology, American Society for Microbiology, US, vol. 40, No. 11, Nov. 1, 2002 (Nov. 1, 2002), pp. 4244-4250, XP002265157, ISSN: 0095-1137, DOI: 10.1128/JCM.40.11.4244-4250.2002.

(Continued)

*Primary Examiner* — Juliet C Switzer
(74) *Attorney, Agent, or Firm* — Karen S. Canady; canady + lortz LLP

(57) ABSTRACT

The invention provides a method for detecting desired *Mycobacterium* species in a sample, the method comprising the steps of: a) mixing mycobacteriophage-coupled paramagnetic particles with the sample to form a reaction mixture under conditions suitable to allow the mycobacteriophage to bind to any mycobacteriophage-sensitive *Mycobacterium* species present in the sample; b) applying a magnetic field to the sample to collect, and separate, mycobacteriophage-coupled paramagnetic particles with bound desired *Mycobacterium* species; c) incubating a suspension of the separated paramagnetic particles with bound *Mycobacterium* species under conditions to allow the mycobacteriophage to replicate inside viable *Mycobacterium* species cells and to lyse the viable *Mycobacterium* species cells; d) recovering, from the incubated suspension, nucleotide, optionally DNA, of lysed *Mycobacterium* species DNA; and e) analysing the nucleotide, optionally DNA, released from the lysed *Mycobacterium* species to identify a signature nucleotide, optionally DNA, sequence that occurs in the desired *Mycobacterium* species. The invention also provides use of a mycobacteriophage; and a kit suitable for performing the aforementioned method.

Figure 1:
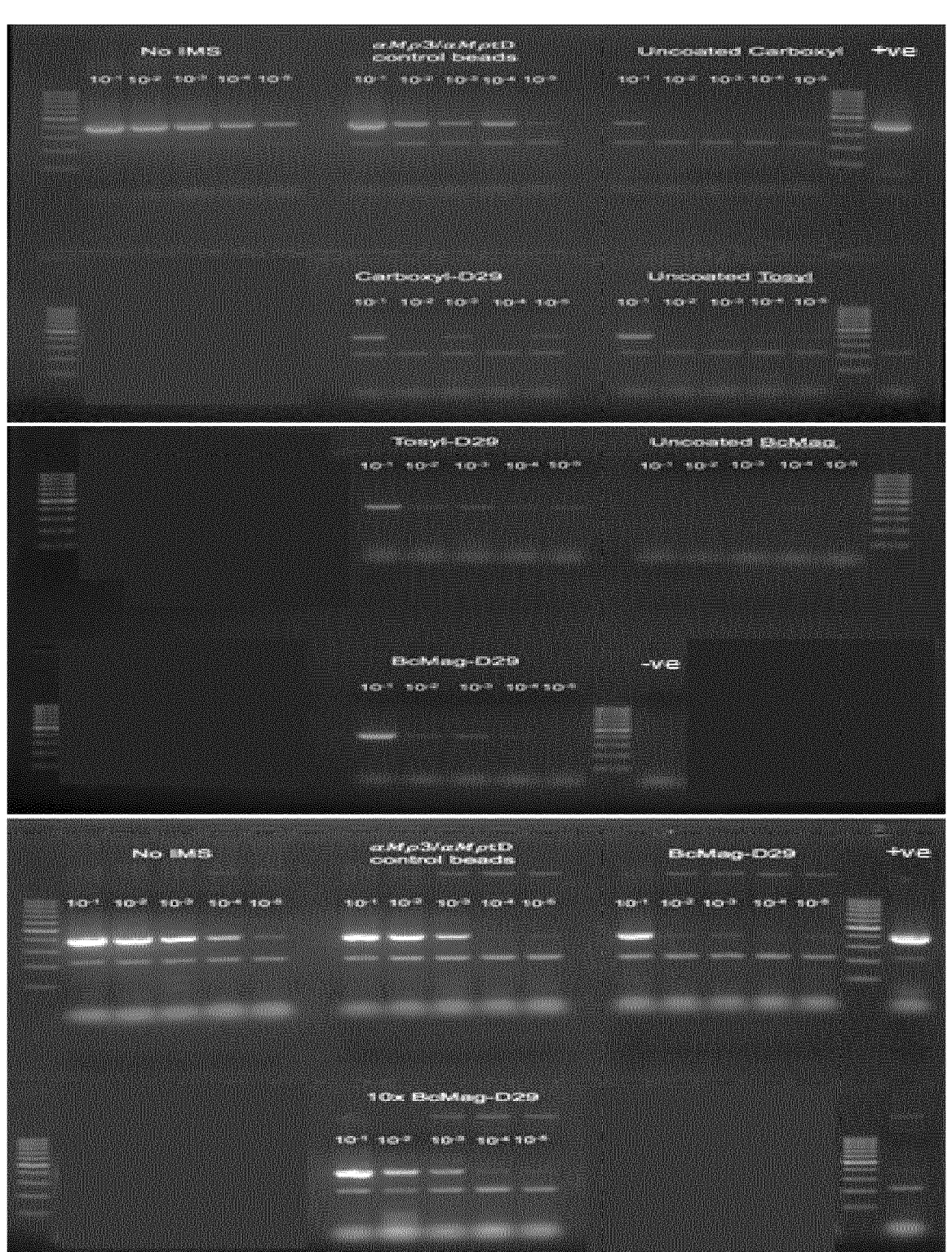

17 Claims, 15 Drawing Sheets
Specification includes a Sequence Listing.

(56)     References Cited

OTHER PUBLICATIONS

Swift, Benjamin, et al., Development of a rapid phage-based method for the detection of viable *Mycobacterium avium* subsp. paratuberculosisin blood within 48 h, Journal of Microbiological Methods, vol. 94, No. 3 , pp. 175-179, XP028700679, ISSN: 0167-7012, DOI: 10.1016/J.MIMET.2013.06.015.

International Search Report for PCT/EP2020/076632 (WO2021058606 Published Apr. 1, 2021).

\* cited by examiner

3 - IS900 Plaque PCR

2 - Phage Amplification Assay

1 - Magnetic Separation

A

1 µm

5 µm

B

5 µm

5 µm

MAP cell bound to phage tail(s)

C

500 nm

Figure 15

N/A = Test not applied due to previous unsatisfactory outcome

DETECTION OF *MYCOBACTERIUM* SPECIES

Detection of pathogenic bacteria has become an area of prime interest because infectious disease has become a life-threatening problem for millions of people around the world.

*Mycobacterium* is a genus of Actinobacteria. Over 190 species are recognized in this genus. This genus includes pathogens known to cause serious diseases in animals and humans, including tuberculosis (*Mycobacterium tuberculosis, Mycobacterium bovis*), *Mycobacterium avium* subsp. *paratuberculosis* (Johne's disease) and leprosy (*Mycobacterium leprae*).

Preferred *Mycobacterium* species are pathogenic.

Pathogenic *Mycobacterium* species include, but are not limited to:

Slowly growing (Runyon's group I, II and III) species, such as *Mycobacterium tuberculosis* complex (MTBC) members are causative agents of human and animal tuberculosis. Species in this complex include: *M. africanum, M. bovis, M. bovis BCG, M. canetti, M. caprae, M. microti, M. mungi, M. orygis, M. pinnipedii, M. suricattae, M. tuberculosis*, the major cause of human tuberculosis;

*Mycobacterium avium* complex—a group of species that, in a disseminated infection but not lung infection, used to be a significant cause of death in AIDS patients. Species in this complex include: *M. avium* subsp. *avium, M. avium* subsp. *paratuberculosis*, which has been implicated in Crohn's disease in humans and is the causative agent of Johne's disease in ruminants such as cattle and sheep, *M. avium* subsp. *silvaticum, M. avium* subsp. *hominissuis, M. colombiense, M. indicus pranii, M. intracellulare;*

Mycolactone-producing mycobacteria such as *M. ulcerans*, which causes the "Buruli", or "Bairnsdale" ulcer;

Ungrouped such as *M. leprae*, which causes leprosy, *M. lepromatosis* (another (less significant) cause of leprosy, described in 2008), *M. marinum* (causes a rare disease called Aquarium granuloma).

This invention relates to a method for detecting viable *Mycobacterium* species, such as, but not limited to *Mycobacterium avium* complex including *M. avium* and *M. avium* subsp. *paratuberculosis*, as well as *M. bovis* and *M. tuberculosis*. The invention also relates to a kit for use in the method.

*Mycobacterium avium* subspecies *paratuberculosis* (MAP) is known to cause disease in animals and may cause disease in humans. MAP is a Gram-positive bacterium of the *Mycobacterium* genus. The bacterium is non-motile and rod-shaped with an average length of approximately 1.5 microns. The bacterial genome is contained within a single, circular chromosome which is around 5 Mbp in length. This bacterium is the causative agent of Johne's disease (JD, also known as *Paratuberculosis*) in ruminants. Johne's disease can cause the loss of milk production, persistent weight loss of cows and refractory diarrhoea and even death.

Infection initially occurs in the lymphoid tissue of the gastrointestinal tract after ingestion of contaminated food or water. The infection presents no clinical signs for up to 10 years and can only be diagnosed when the immune response begins. Due to the long incubation period, vaccination that only decreases the disease rate rather than offer immunity to infection, has been deemed impracticable.

Studies have also shown that MAP is associated, in humans, with Crohn's disease, and potentially other chronic conditions such as Type 1 Diabetes mellitis, Multiple Sclerosis, Hashimoto's thyroiditis. MAP leads to the main infection of cattle and sheep and other ruminants. In addition, MAP can also be isolated from protozoa, animals such as rabbits, red deer, bison, and other wild animals. Its presence has been reported in carnivorous birds, primates and the human body. Infected animals show stubborn diarrhoea, with the continuation of diarrhoea symptoms, sick animals appear anaemic with progressive weight loss. The MAP infection incubation period is a long and slow course, it may occur in asymptomatic hosts that shed viable bacteria in their faeces, leading to the infection of other healthy animals.

Detecting the presence of *Mycobacterium* species in people or animals is of interest for the diagnosis of mycobacterial infections. Rapid and reliable detection of infection by *Mycobacterium* species is important for controlling disease, and the ability to use high-throughput techniques allows screening of large numbers of samples. It would be of great value, for example, to provide high-throughput screening that could rapidly and reliably test samples from individual animals within a herd of cattle for *Mycobacterium bovis* (Bovine TB) or *Mycobacterium avium* subsp. *paratuberculosis* (Johne's disease), both of which are endemic diseases of cattle in the UK. Both *Mycobacterium* species can be detected in the blood of animals exposed to *M. bovis* or MAP, even when they are in the subclinical stage of disease. The rapid and reliable detection of these organisms within a herd is a very important step in control of disease.

Current rapid methods for detection of viable *Mycobacterium* species are able to detect and enumerate viable MAP in blood within two or three days. However, the method used is labour intensive and would be difficult to scale up for high-throughput analysis of samples. In a veterinary setting, where animals from a whole herd need to be tested, often hundreds of samples need to be tested at the same time, and current methods are too costly and labour-intensive to make large scale testing practicable.

The current clinical standard tests for TB and Johne's disease are antibody-based (immune response) tests. Antibody-based tests detect the response of the host immune system to the organism rather than detecting viable organisms. The sensitivity of these tests is known to be low when used as a diagnostic, requiring repeat results or advanced stages of infection before a clear positive result is obtained. A particular disadvantage of antibody-based tests is that these tests also do not distinguish between infected and vaccinated animals. In previous PCR-based methods for detecting *Mycobacterium* species, the sensitivity of the assay was limited by the ability to recover DNA from the *Mycobacterium* species which are physically robust and difficult to lyse. In addition, previous PCR-based methods do not easily differentiate between live and dead cells. In the food industry especially, the ability to differentiate between live and dead *Mycobacterium* species is very important since processed food may still contain the DNA of inactivated cells. Potentially, the ability to distinguish between live and dead *Mycobacterium* species is also important in clinical diagnostics using blood samples, since dead cells within macrophages would also be detected, even if the animal or human was recovering from infection.

Many of the major disease-causing *Mycobacterium* species such as *Mycobacterium avium* subsp. *paratuberculosis* (MAP), *Mycobacterium tuberculosis*, and *Mycobacterium bovis* are slow-growing and therefore difficult to culture. The length of time that it takes to culture these species makes it difficult to use culture as a diagnostic test for infection.

Over recent years, there has been increasing interest in bacteriophage-based methods as a potential alternative to culture for the rapid detection and enumeration of viable MAP. A phage-based assay for detecting MAP was first reported by Stanley et al. (2007), who demonstrated that the FASTPlaqueTB phage amplification assay for detecting *Mycobacterium tuberculosis* in sputum (commercially available at the time from Biotec Laboratories, Ipswich, UK) could be repurposed for detection of viable MAP in cows' milk. Foddai et al. (2009) subsequently optimised the FASTPlaqueTB assay conditions to ensure accurate quantitation of the number of viable MAP present in milk. The main changes introduced were a longer incubation time after phage infection (3.5 h instead of 1 h) before plating with *Mycobacterium smegmatis* and molten 7H9 agar, and virucide (ferrous ammonium sulphate, FAS) treatment at the 2 h point within this incubation period rather than at 1 h just before plating. The ability of the optimised phage assay as a tool to monitor the inactivation kinetics of MAP in milk during heat treatment was subsequently demonstrated (Foddai et al. 2010a). Later, the same researchers combined the optimised phage amplification assay with peptide-mediated magnetic separation (PMS) employing MyOne tosylactivated Dynabeads coated with two biotinylated peptides aMp3 and aMptD, originally described by Stratmann et al. (2002, 2006). The PMS-phage assay was optimized in order to maximize sensitivity for MAP detection (Foddai et al. 2010b) and then used to detect viable MAP in bovine milk and faeces (Foddai et al. 2011). PMS achieves two important things in advance of the phage amplification assay: (1) selective capture of mycobacterial cells from other microorganisms present, and (2) physical separation of MAP cells from the complex milk sample matrix. This means that the D29 phages can encounter the MAP cells in a sample more easily, since milk components are largely eliminated. There is also the potential to 10-fold concentrate MAP cells from a milk sample if the beads are resuspended in a smaller volume (0.1 ml rather than 1 ml) of broth after PMS.

At Queen's University Belfast (QUB), we have been using the PMS-phage assay with some modifications, in terms of milk sample preparation mainly (Foddai and Grant 2015), for many years now, chiefly to test for viable MAP in milk (Foddai and Grant 2017, O'Brien et al. 2018) and calf milk replacer (Grant et al. 2017). Our studies have consistently shown that the PMS-phage assay is a very sensitive test for detecting viable MAP, and a promising rapid alternative to MAP culture; which takes a long time to return results but is still considered the gold standard method for demonstrating the presence of viable MAP in veterinary samples. In our hands, the PMS-phage assay performs consistently well since we have become proficient in its application and recognise the key steps within the assay that need to be performed correctly to avoid false positive or false negative results. However, when researchers in other laboratories have attempted to adopt the optimised phage assay or the PMS-phage assay, technology transfer has generally not been a smooth process (e.g. Butot et al. 2019), and considerable training and troubleshooting has been needed from QUB researchers. We acknowledged some time ago (Foddai and Grant 2017) that the PMS-phage assay has a complex, multi-step protocol that does not lend itself well to high throughput testing of milk samples. There are a couple of key parts of the PMS-phage assay protocol that must be performed with care, otherwise false positive plaques due to non-inactivated seed phages (as a consequence of ineffective virucide treatment) or release of progeny phages before plating in agar (due to non-adherence to stipulated incubation times) may result. False negative results may also occur because plaque PCR does not confirm the presence of MAP DNA within the maximum 10 plaques harvested (irrespective of the number of plaques present).

If phage-based assays for viable MAP are to have any future application for the diagnosis of JD, for example, then a much simpler, user-friendly test protocol is going to be required. This urgent need prompted us to develop a novel one-day phage-based test for viable MAP.

The invention provides a specific and sensitive method of detecting viable *Mycobacterium* species and, in particular, a method which could be performed in a 'single-tube' format that has the potential to be automated to allow rapid and cost effective testing of large sample numbers. It would be particularly advantageous to provide a test that could differentiate between infected and vaccinated individuals.

According to a first aspect of the invention, there is provided a method for detecting desired *Mycobacterium* species in a sample, the method comprising the steps of:

a) mixing mycobacteriophage-coupled paramagnetic particles with the sample to form a reaction mixture under conditions suitable to allow the mycobacteriophages to bind to any mycobacteriophage-sensitive *Mycobacterium* species present in the sample;

b) applying a magnetic field to the sample to collect, and separate, the mycobacteriophage-coupled paramagnetic particles with bound desired *Mycobacterium* species;

c) incubating a suspension of the separated paramagnetic particles with bound *Mycobacterium* species under conditions to allow the mycobacteriophage to replicate inside viable *Mycobacterium* species cells and to lyse the viable *Mycobacterium* species cells;

d) recovering, from the incubated suspension, nucleotide, optionally DNA, of the lysed *Mycobacterium* species; and e) analysing the nucleotide, optionally DNA, released from the lysed *Mycobacterium* species to identify a signature nucleotide sequence that occurs in the desired *Mycobacterium* species.

The method of the first aspect of the invention employs mycobacteriophage-coupled paramagnetic particles, such as D29 mycobacteriophages, in a different manner. Mycobacteriophages were coupled to paramagnetic beads to permit physical capture of mycobacteriophage-sensitive *Mycobacterium* species (hereinafter MAP cells as an example) and then natural lysis of MAP cells in advance of MAP-specific qPCR, rather than phage amplification within MAP cells and a plaque assay endpoint. The objectives of this study were to: (1) successfully coat D29 phages onto paramagnetic beads and use these phage-coated beads for phagomagnetic separation (PhMS) of MAP cells from milk; (2) determine the best protocol for harvesting DNA released from viable MAP cells lysed by action of the D29 phages; and (3) combine the PhMS and DNA harvesting steps with quantitative IS900 PCR (qPCR) to produce a rapid, sensitive and specific PhMS-qPCR assay for viable MAP in milk. From the outset, we are aware of the existence of the Actiphage® Rapid test, which is a commercially available rapid phage-based test from PBD Biotech Limited (Thurston, UK) based on technology developed by Drs Cath Rees and Ben Swift at the University of Nottingham, UK (Swift et al. 2019). The PhMS-qPCR test we describe here may appear similar to the Actiphage® Rapid test, but it has a different modus operandi.

Optionally, before step c), the collected paramagnetic particles (in a first volume) with bound *Mycobacterium* species are washed to remove residual sample that is not paramagnetic particles with bound desired *Mycobacterium* species, and resuspended in a smaller (or second) volume. For example, the ratio of the first volume to the second volume may be 10 to 30:1, optionally, about 20:1 (all v/v).

Optionally, the step c) incubation is carried out to the endpoint of cell lysis.

Optionally, in step c), the suspension of the separated paramagnetic particles with bound *Mycobacterium* species is incubated at 37° C. for 1 to 5 hours, optionally about 4 hours, to allow mycobacteriophage to replicate inside viable *Mycobacterium* species cells and to lyse the viable *Mycobacterium* species cells.

Optionally, step e) comprises probe-based qPCR.

Optionally, following step c), the incubated suspension is subjected to heat shock conditions. Such heat shock conditions may comprise a temperature in the range of 40 to 70° C. for a period of at least 15 seconds to 1 minute; optionally about 55° C. for about 1 minute to ensure maximal release of *Mycobacterium* species DNA from cells lysed or weakened by the action of internal mycobacteriophages.

Optionally, the mycobacteriophage is selected from Barnyard mycobacteriophage, Black Raspberry mycobacteriophage, Bxz2 mycobacteriophage, Che8 mycobacteriophage, L5 mycobacteriophage, Omega mycobacteriophage, PBI1 mycobacteriophage, PG2 mycobacteriophage, Rosebush mycobacteriophage, SB1 mycobacteriophage, Cooper mycobacteriophage, Wildcat mycobacteriophage, TM4 mycobacteriophage and D29 mycobacteriophage; optionally D29 mycobacteriophage.

Optionally, the *Mycobacterium* species is *Mycobacterium avium* subsp. *paratuberculosis* and the mycobacteriophage are selected from Bxz2 mycobacteriophage, L5 mycobacteriophage, PBI1 mycobacteriophage, and D29 mycobacteriophage; optionally D29 mycobacteriophage.

Optionally, the paramagnetic particles have a diameter in the range of 0.25 to 1.5 μm; optionally about 1 μm. Further optionally, the paramagnetic particles are selected from MyOne 1 μm Tosylactivated Dynabeads, BcMag 1 μm tosylactivated beads and Carboxyl-Adembeads (300 nm); optionally BcMag 1 μm tosylactivated beads.

Optionally, about 5 to 25, further optionally about 10, mycobacteriophages are coupled to each paramagnetic particle.

Optionally, about $2.5 \times 10^7$ D29 phage-coated beads are present in the step a) reaction mixture, when the sample is milk.

Optionally, the *Mycobacterium* species is *Mycobacterium avium* subsp. *paratuberculosis*; further optionally for detecting and monitoring Johne's disease in ruminants such as cattle and sheep.

Optionally, the method is for detecting and monitoring MAP infection or presence in humans. For example, the MAP infection or presence may be associated with Crohn's disease.

Optionally, the *Mycobacterium* species is *Mycobacterium bovis*; further optionally for detecting and monitoring bovine tuberculosis in ruminants such as cattle.

Optionally, the *Mycobacterium* species is *Mycobacterium tuberculosis*; further optionally for detecting and monitoring tuberculosis in humans.

The mycobacteriophage used may be selected because it specifically infects the desired *Mycobacterium* species to be detected. Alternatively, the mycobacteriophage used may be selected because it is a broad host range bacteriophage and infects a range of *Mycobacterium* species including the desired *Mycobacterium* species.

Mycobacteriophages are only able to lyse viable cells (also called replication competent cells). Viable *Mycobacterium* species in a sample allow the mycobacteriophage to replicate which eventually results in host cell lysis. However, non-viable *Mycobacterium* species cannot support the mycobacteriophage replication and are not lysed by the mycobacteriophage. This allows the method to distinguish between samples that contain viable *Mycobacterium* species and samples that contain non-viable *Mycobacterium* species.

Phages are extremely resistant in a range of harsh conditions including pH and temperature, and can even be used in the presence of nucleases or proteolytic enzymes, without degradation. Following this, the advantage of the phage assay is that it is able to detect viable mycobacterial cells quickly. Phages have the very strong and specific ability to bind to target bacteria. Phagomagnetic separation technology (of the present invention) is using magnetic beads coated with an appropriate mycobacteriophage to capture mycobacterial cells.

The main advantages of using phagomagnetic separation instead of immunomagnetic separation rely on the use of the bacteriophages for biorecognition. In contrast to antibody generation, phages are animal-free, cost-efficiently produced by bacterial infection, taking only a few hours. Another feature which makes them suitable as a biorecognition element is their outstanding stability.

Unlysed *Mycobacterium* species cells are removed from the reaction mixture at step d). Unlysed *Mycobacterium* species may be removed from the reaction mixture by any suitable method. Unlysed *Mycobacterium* species may be removed from the reaction mixture by centrifugation, filtration or by barrier methods such as spin columns. For example, centrifuging the incubated suspension to recover nucleotide, optionally DNA, of the lysed *Mycobacterium* species from a supernatant phase The sample may be any sample suspected of containing *Mycobacterium* species. For example, the sample may be milk or faeces, a blood or tissue sample, or a sample of food or animal feed. The sample may be made by mixing or dispersing a sample suspected of containing mycobacteria in a buffer solution.

The desired *Mycobacterium* species cell may be any species belonging to the genus *Mycobacterium*, for example *Mycobacterium avium* subsp. *paratuberculosis* (MAP), *Mycobacterium tuberculosis*, *Mycobacterium bovis*, *Mycobacterium leprae*, *Mycobacterium avium*. The desired *Mycobacterium* species cell may belong to any *Mycobacterium* species of interest. The desired *Mycobacterium* species cell may be *Mycobacterium avium* subsp. *paratuberculosis*; optionally from strain K 10, or B4.

The mycobacteriophage may be any lytic mycobacteriophage that is able to infect and lyse the desired *Mycobacterium* species. The mycobacteriophage may be specific to the desired *Mycobacterium* species. The mycobacteriophage may be any broad host range mycobacteriophage that is able to infect and lyse the desired *Mycobacterium* species. For example, the mycobacteriophage may be D29 or TM4 mycobacteriophage. Alternatively, the mycobacteriophage may be Bxz2 or L5.

The D29 and TM4 mycobacteriophages have a broad host range (see Table 2 of Rybniker et al, Journal of Medical Microbiology (2006), 55, 37-42, incorporated herein by reference).

The mycobacteriophage may only lyse live desired *Mycobacterium* species. The mycobacteriophage may not lyse dead or non-viable *Mycobacterium* species.

Nucleotide, optionally DNA, from the lysed *Mycobacterium* species may be analysed by any suitable technique to identify signature sequences that are found in the desired *Mycobacterium* species cell. The reaction mixture may be analysed to identify signature sequences from one or more than one different desired *Mycobacterium* species, for example from one or two different desired *Mycobacterium* species, or three, four, five, six, seven, eight, nine, ten, eleven or twelve or more different desired *Mycobacterium* species. The nucleotide, optionally DNA, may be analysed by PCR using primers that anneal, allow amplification, specifically to a signature nucleotide sequence that occurs in the desired *Mycobacterium* species cell or each of the desired *Mycobacterium* species.

The nucleotide, optionally DNA, may be analysed by PCR using primers that anneal specifically to a signature nucleotide, optionally DNA, sequence that occurs in the desired *Mycobacterium* species cell or each or the desired type of *Mycobacterium* species. To increase the specificity more than one, more than two, more than three, more than four, more than five, more than six, more seven or more than eight signature sequences may be considered for each *Mycobacterium* species to be detected.

The signature DNA sequence may be selected from an insertion element IS900, a unique gene sequence f57 for *Mycobacterium avium* subsp. *paratuberculosis* (MAP)—see Table below—or target 251 (MAP2765c).

Suitable forward and reverse primers include IS900QF and IS900QR, the probe being IS900QP.

Applied Biosystems TaqMan TAMRA probes are dual-labelled probes used for real-time PCR applications using TaqMan chemistry. TaqMan TAMRA Probes comprise a 5' fluorescent reporter dye (FAM, VIC, or TET) and a 3' fluorescent quencher (TAMRA, a fluorescent dye that can be multiplexed with up to three dyes).

Alternatively, Applied Biosystems TaqMan MGB (minor groove binder) probes are dual-labelled probes used for real-time PCR applications using TaqMan chemistry. TaqMan MGB Probes comprise a 5' fluorescent reporter dye and a 3' nonfluorescent quencher (NFQ). The NFQ offers the advantage of lower background signal, which results in better precision in quantitation. TaqMan MGB probes are available with FAM, VIC, TET, and NED reporter dyes.

The TaqMan system detects PCR products using the 5 nuclease activity of Taq DNA polymerase on fluorogenic DNA probes during each extension cycle. The TaqMan probe is labelled with a fluorescent reporter dye at the 5 end and a fluorescent quencher dye at the 3 end. When the probe is intact, the quencher dye reduces the emission intensity of the reporter dye. If the desired sequence is present, the probe anneals to the target and is cleaved by the 5 nuclease activity of Taq DNA polymerase as the primer extension proceeds. As the cleavage of the probe separates the reporter dye from the quencher dye, the reporter dye fluorescence increases as a function of cycle number. Threshold cycle ($C_T$) is defined as the cycle number at which the reporter fluorescence passes a fixed threshold above baseline. The greater the initial concentration of the desired DNA, the sooner a significant increase in fluorescence is observed. Using the standard curve generated with a desired DNA sequence of known copy number, the starting amount of desired DNA in unknown samples can be determined. Quantitative PCR has several advantages over the conventional end-point PCR: qPCR increases the specificity by including an internal hybridization probe, reduces cross-contamination by including UNG (dUTP N-glycosylase) and eliminating post-PCR processing, determines the starting concentration of desired sequence in the sample, and is less sensitive to PCR inhibitors.

Further alternative suitable forward and reverse primers include F57QF and F57QR, the probe being F57QP.

Suitable PCR primer and probe sequences to amplify the multicopy element IS900 and the single copy element F57 of *Mycobacterium avium* subsp. *paratuberculosis* include:

| Desired gene | Primers and probe Sequence (5'-3') |
|---|---|
| IS900 (ATCC 19698) | IS900QF CCGGTAAGGCCGACCATTA (SEQ ID NO: 1) 67 bp<br>IS900QR ACCCGCTGCGAGAGCA (SEQ ID NO: 2)<br>IS900QP FAM-CATGGTTATTAACGACGACGCGCAGC (SEQ ID NO: 3)-TAMRA |
| F57 (acc. No. X70277) | F57QF AACTAAGCGGATCGACAATTC (SEQ ID NO: 4) 80 bp<br>F57QR TGGTGTACCGAATGTTGTTG (SEQ ID NO: 5)<br>F57QP FAM-TGCAACTCGAACACACCTGGGA (SEQ ID NO: 6)-TAMRA |

FAM, fluorescent reporter dye 6-carboxyfluorescein; TAMRA, quencher dye N',N',N',N'-tetramethyl-6-carboxyrhodamine.

Other suitable primers and TaqMan probes to detect *M. avium* subsp. *paratuberculosis* include:

| Desired (GenBank accession no.) | Oligonucleotide sequence |
|---|---|
| Amplicon I IS900 (AE016958.1) | |
| Forward | 5'-AAT GAC GGT TAC GGA GGT GGT-3' |
| Reverse | 5'-GCA GTA ATG GTC GGC CTT ACC-3' |
| Probe | FAM-TCC ACG CCC GCC CAG ACA GG-TAMRA |
| Amplicon II 251 (AF445445) | |
| Forward | 5'-GCA AGA CGT TCA TGG GAA CT-3'2, 38 |
| Reverse | 5'-GCG TAA CTC AGC GAA CAA CA-3' |
| Probe | FAM-CTG ACT TCA CGA TGC GGT TCT TC-TAMRA |
| Amplicon III f57 (X70277) | |
| Forward | 5'-TAC CGA ATG TTG TTG TCA CCG-3' |
| Reverse | 5'-TGG CAC AGA CGA CCA TTC AA-3' |
| Probe | FAM-CCG GTC CCA GGT GTG TTC GAG TTG-TAMRA |
| Amplicon IV MAP0865 (AE016958.1) | |
| Forward | 5'-GCG CGG CCA GTA TGG ATA TA-3' |
| Reverse | 5'-GAC TCA ACC CAA CGA GCT CC-3' |
| Probe | FAM-AGA TGC CTC TCC GAT GCT CGA TGG-TAMRA |

Further alternatively, the signature DNA sequence may be the insertion element IS900 and the gene sequence f57 for

*Mycobacterium avium* subsp. *paratuberculosis* (MAP) (in other words using both IS900 and F57 as desired genes) for the screening and confirmation of the presence of MAP DNA. This method and kit is intended for use with cattle, sheep, and goats, for sample types such as faeces, organs, bacterial colonies, and broth culture.

The DNA may be analysed using Sidoti et al. primers (see Table 2 above) and TaqMan probe (see Table 2 above) targeting IS900 gene, as set out above, for *M. avium* subsp. *paratuberculosis* (MAP) genomes—this is designed for the in vitro quantification of MAP genomes. The kit is designed to have the broadest detection profile possible whilst remaining specific to the MAP genome. The primers and probe sequences in this kit have 100% homology with a broad range of MAP sequences. The F57 sequence is a well characterized marker for this strain and the primers and probe have 100% homology to the four sequences currently in the NCBI database EU379657.1, X70277.1, AE016958.1, EU092638.1. The primer and probe mix provided exploits the so-called TaqMan® principle. During PCR amplification, forward and reverse primers hybridize to the MAP DNA. When an Applied Biosystems TaqMan TAMRA probe is used, a fluorogenic probe is included in the same reaction mixture, the probe being a DNA probe labelled with a 5'-dye (FAM) and a 3'-quencher (TAMRA). During PCR amplification, the probe is cleaved and the reporter dye and quencher are separated. The resulting increase in fluorescence can be detected on a range of real-time PCR platforms.

The sample may be a sample of blood, body fluid or tissue. The sample may be a sample of blood, serum, sputum, milk, saliva, urine, faeces. The sample may be a semen sample from bulls used in herd assurance programmes. The sample may be a sample of a product for human or animal consumption. For example, the sample may be a sample of milk, cheese or a dairy product containing raw milk.

The method may be performed in one reaction vessel, for example one test tube, one microcentrifuge tube or one well of a multiwell plate. All steps of the method may be performed in one reaction vessel. It is advantageous that the method may be performed in one reaction vessel because it allows the method to be carried out as a high throughput screening method. The method may be a high throughput screening method. This is advantageous if a large number of samples need to be tested, for example if a herd of cattle needs to be tested for MAP.

Steps a) to e) of the method may be performed within 24 hours. This is advantageous because it can be determined whether there are live, or viable, *Mycobacterium* species in a sample within 24 hours or within 48 hours. Preferably, results can be obtained in less than 48 hours, less than 24 hours, less than 12 hours, less than 10 hours, less than 8 hours, less than 6 hours or less.

The method of the invention would be able to distinguish between an animal or individual that had been vaccinated against a *Mycobacterium* species and an individual that had been infected with the *Mycobacterium* species. This allows vaccination of the animals, for example humans and cows against *Mycobacterium* species to be carried out and a test still to be available to detect mycobacterial infection.

Previous methods for detecting *Mycobacterium* species that use anti-mycobacterial antibodies produced by an infected animal or individual as markers of infection cannot be used on animals or individuals that have been vaccinated because the immune reaction to the vaccine produces antibodies that may be detected by these tests.

The present method can distinguish between an infected animal/individual and a vaccinated animal/individual because the present method detects viable *Mycobacterium* species cells.

The method of the invention also allows detection of *Mycobacterium* species, for example in blood samples, at very early stages of infection, and before any clinical symptoms are visible. The method may be able to identify the presence of live mycobacteria when they are present in a sample at very low numbers, for example less than 10 cells per ml of sample.

The method of the invention could also be used to monitor the efficacy of a treatment, and to screen for whether the numbers of bacteria are reducing as treatment is given.

Two or more different desired *Mycobacterium* species may be identified in a sample at the same time by using a broad host range mycobacteriophage or by using two or more mycobacteriophages that specifically infect the two or more different desired *Mycobacterium* species. Signature sequences from the two or more different *Mycobacterium* species may be identified by any method capable of identifying a specific nucleotide, optionally DNA, sequence, for example using PCR reactions with primers specific to each desired *Mycobacterium* species. This allows two or more different desired *Mycobacterium* species to be identified in a sample at the same time.

In another aspect, the present invention provides the use of a mycobacteriophage that specifically infects a desired *Mycobacterium* species in a method for detecting infection by the desired *Mycobacterium* species wherein the mycobacteriophage lyses the desired *Mycobacterium* species to release mycobacterial nucleotide, optionally DNA, and signature mycobacterial nucleotide, optionally DNA, sequences are identified by PCR, or other method capable of identifying a specific nucleotide, optionally DNA, sequence.

In still another aspect, the present invention provides a kit suitable for performing the method of the present invention. A kit may comprise a bacteriophage that is specific to a desired *mycobacterium* and instructions for their use according to the method of the present invention.

The kit may comprise mycobacteriophage-coupled paramagnetic particles that specifically bind to the desired *Mycobacterium* species.

The kit may further comprise oligonucleotides (or primers) and probe that allow the specific amplification of a signature nucleotide, optionally DNA, sequence in the desired *Mycobacterium* species.

There now follows by way of example only a detailed description of the present invention with reference to the accompanying drawings, in which;

FIG. 1. Magnetic separation of MAP ATCC 19698 from a dilution series prepared in 7H9 broth using Carboxyl-Adembeads 300 nm, MyOne Tosylactivated Dynabeads, 1× and 10× BcMag Tosylactivated Beads coated with D29 phages, compared to the currently used biotin-aMp3 and biotin-aMptD biotinylated peptide-coated BcMag 1 μm tosylactivated beads.

Figure 2:
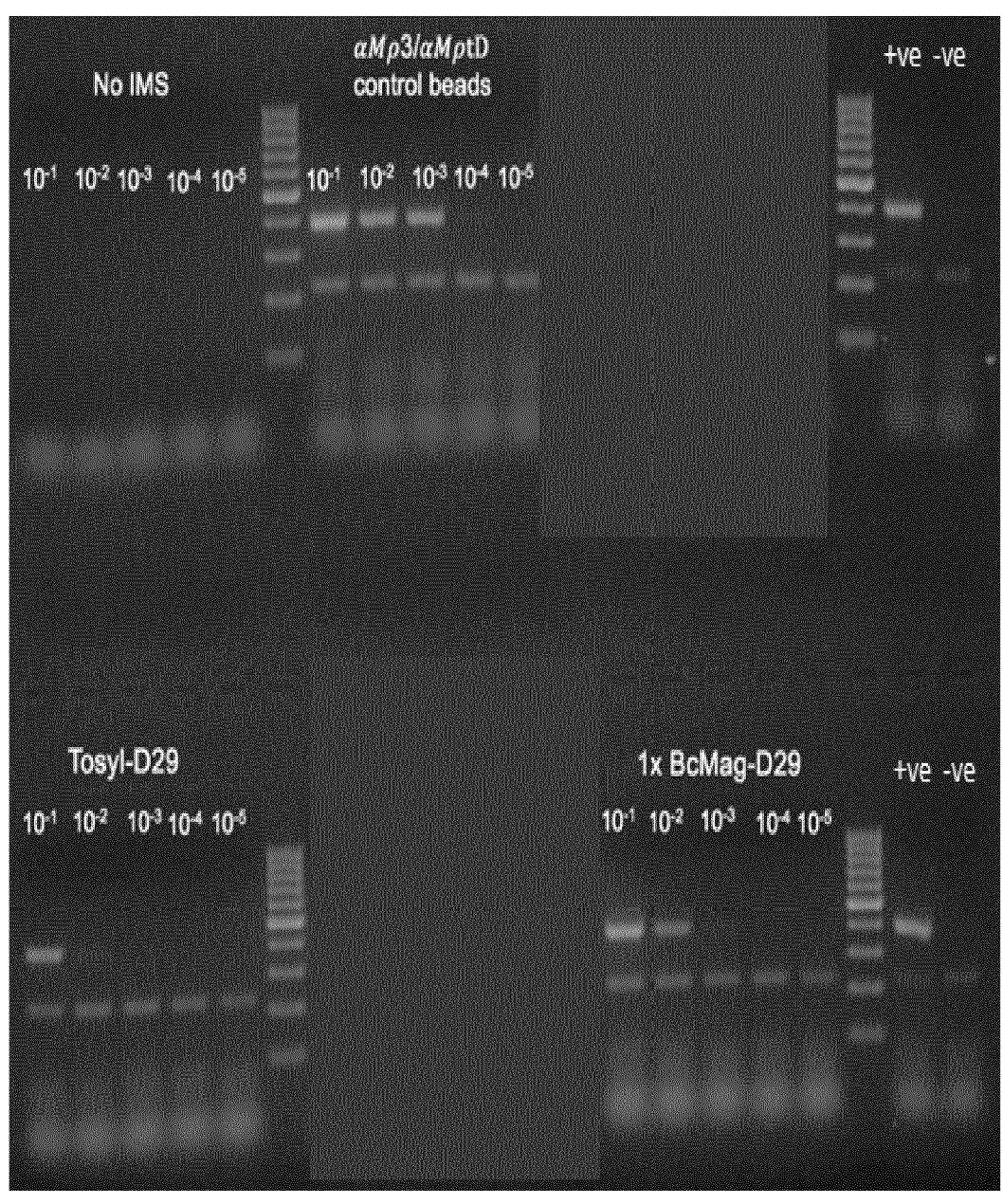

FIG. 2. Magnetic separation of MAP ATCC 19698 from a dilution series prepared in UHT Whole Milk using MyOne Tosylactivated Dynabeads, 1× and 10× BcMag 1 μm Tosylactivated Beads coated with D29 phages, compared to the currently used biotin-aMp3 and biotin-aMptD biotinylated peptide-coated BcMag 1 μm tosylactivated beads.

Figure 3:
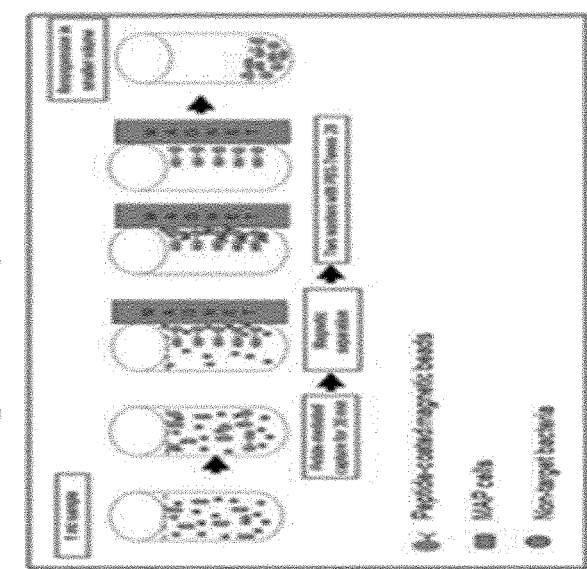

FIG. 3 compares, figuratively, Magnetic separation using peptide-coated paramagnetic beads to selectively capture MAP cells from milk; Phage amplification assay to give an indication of the number of viable MAP within 24 h; and IS900 PCR.

Figure 4:
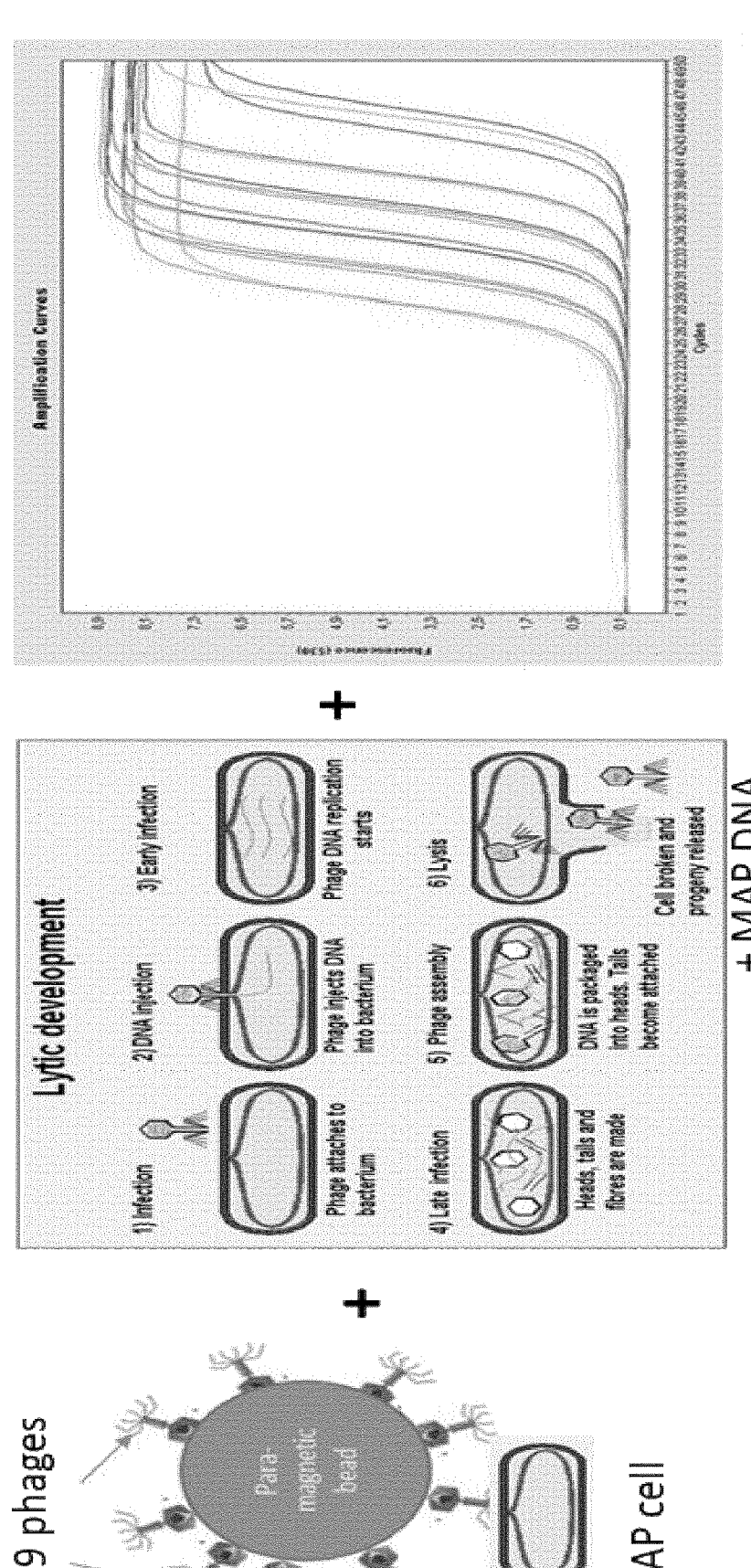

FIG. 4 illustrates, figuratively, the detection of MAP based on D29 bacteriophage-mediated magnetic separation (phagomagnetic separation) combined with a MAP-specific qPCR, and is comprised of three parts:

capture of desired MAP cells by phage coated magnetic beads

DNA release from phage-infected viable MAP cells due to phage lytic action

Detection of resultant MAP DNA by qPCR

Figure 5:
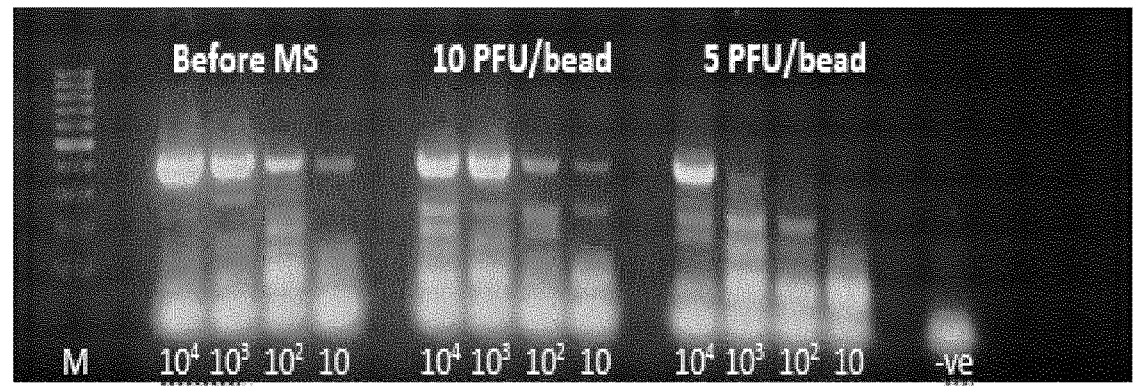
Figure 5:
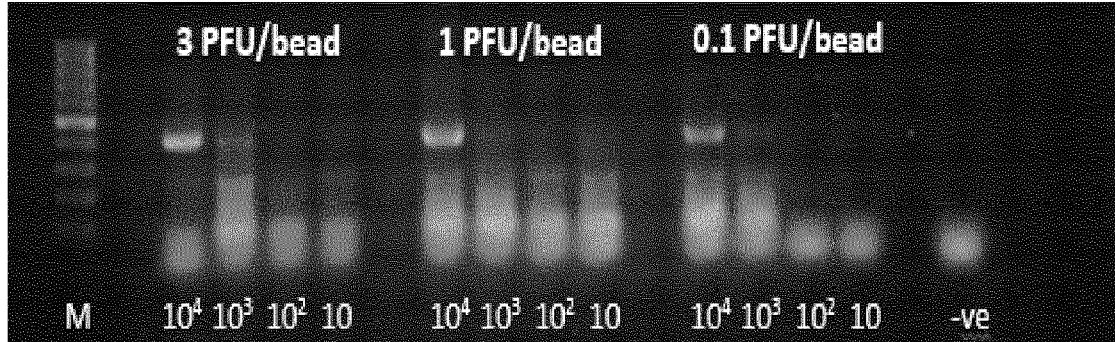

FIG. 5: 'Before MS' are the control samples, against which capture capability of different types of coated bead was compared—results clearly indicate a PFU/bead ratio of 10 PFU/bead is optimal as all four MAP cell concentrations are still detectable and PCR bands are of similar intensity at all four concentrations, whereas, at other coating ratios, fewer and fewer MAP cell concentrations test PCR positive.

Figure 6:
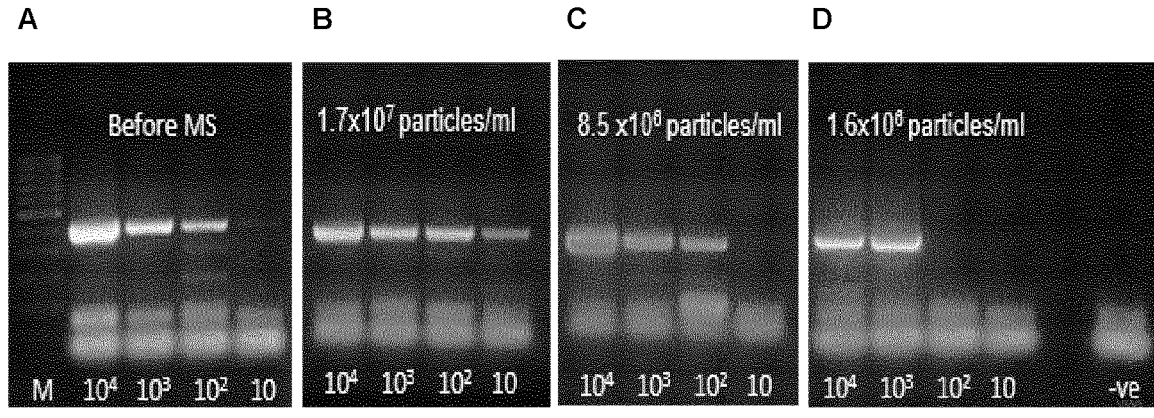

FIG. 6: MAP cell capture from spiked broth suspensions (10 to $10^4$ cells/ml) processed through PhMS using decreasing amounts of D29-coated paramagnetic beads assessed by IS900 PCR. Results are for DNA extracted by boiling at 99° C. for 25 min from samples (A) before magnetic separation (Before MS), and immediately after PhMS using: (B) 10 μl of coated beads prepared using 10 mg BcMag™ tosylactivated beads (final concentration $1.7×10^7$ beads/ml of test sample); (C) 5 μl of coated beads prepared using 10 mg BcMag™ tosylactivated beads (final concentration $8.5×10^6$ beads/ml of test sample), and (D) 1 μl of coated beads prepared using 10 mg BcMag™ tosylactivated beads (final concentration $1.7×10^6$ beads/ml of test sample). M: TrackIt 100 bp DNA Ladder (Thermofisher Scientific), −ve: negative control. A to D are left to right in FIG. 6. 'Before MS' are the control MAP cell concentrations tested by PCR directly, against which capture capability of three different coated bead concentrations are compared. Results indicate that a bead concentration of $1.7×10^7$ beads/ml is optimal for MAP capture, while lower bead concentrations will miss lower MAP concentrations, i.e. won't have sufficient detection sensitivity.

Figure 7:
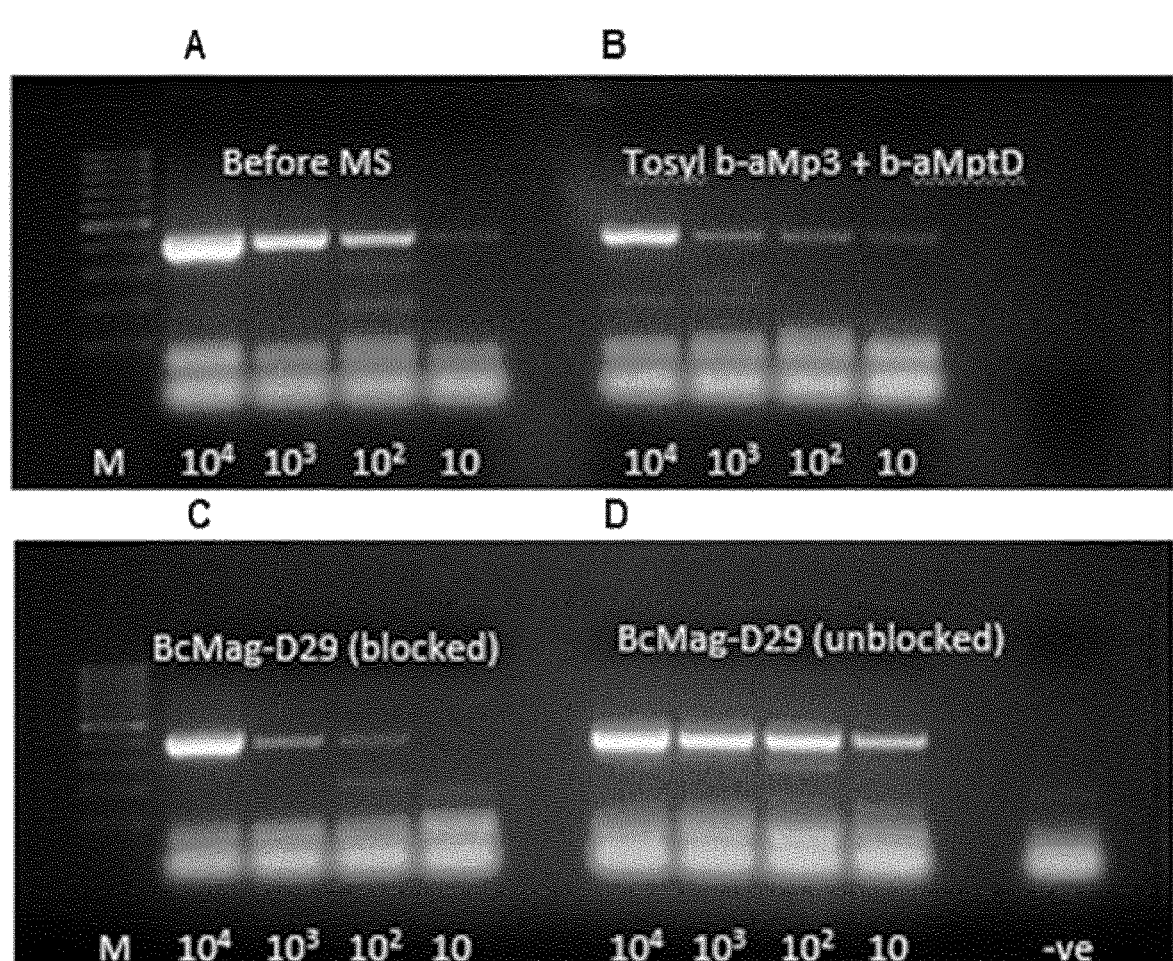

FIG. 7: Comparison of MAP cell capture from spiked broth suspensions (10 to $10^4$ cells/ml) by magnetic separation using peptide- and phage-coated paramagnetic beads assessed by IS900 PCR. Results are for DNA extracted by boiling at 99° C. for 25 min from samples (A) before magnetic separation (Before MS), (B) after Peptide-mediated MS involving a 50:50 mixture of MyOneTosylactivated beads (Life Sciences) covalently coated to two biotinylated peptides aMp3 and aMptD (PMMS); (C) D29 phage-coated BcMag tosylactivated beads blocked overnight with PBS-0.5% bovine serum albumin, and (D) unblocked D29 phage-coated BcMag tosylactivated beads. M: TrackIt 100 bp DNA Ladder (Thermofisher Scientific), −ve: negative control. A and B are left to right, top row; and C and D are left to right, bottom row, of FIG. 7. FIG. 7 shows that phage-coated BcMag tosylactivated beads should not be blocked with PBS-BSA, as unblocked beads demonstrated superior MAP capture capability than blocked phage-coated beads, and also than blocked peptide-coated beads.

Figure 8:
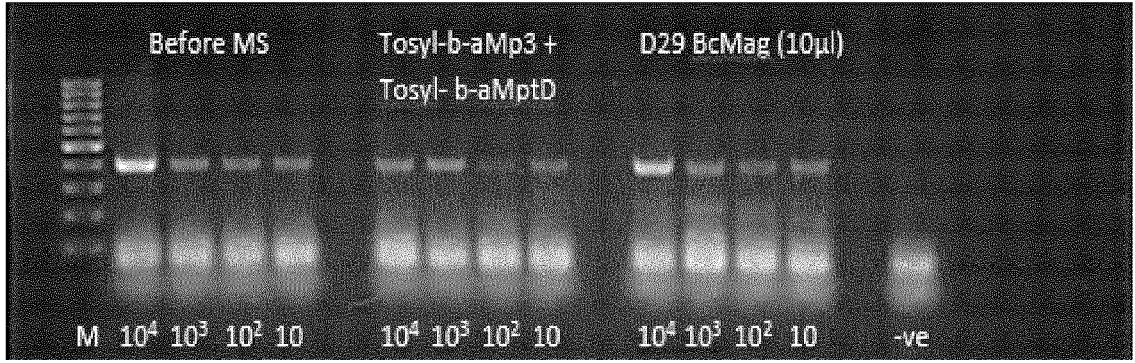
Figure 8:
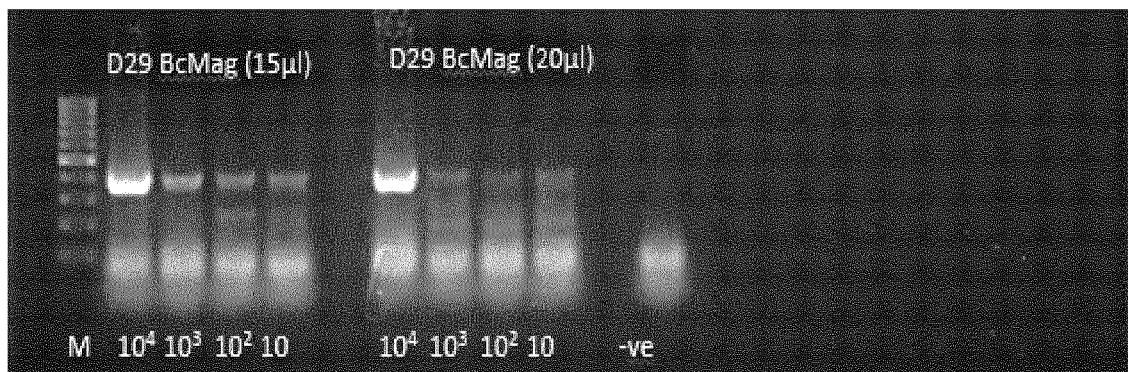

FIG. 8: Comparison of the recovery of MAP cells from UHT milk samples spiked at four concentrations ($10^4$, $10^3$, $10^2$ and 10 MAP/ml) after MS assessed by IS900 PCR. Results are for DNA extracted by boiling at 99° C. for 25 min from samples before MS and immediately after PMS using 10 μl of peptide-coated MyOne tosylactivated Dynabeads and PhMS using 10, 15 and 20 μl ($1.7×10^7$, $2.2×10^7$ and $3.4×10^7$ beads/ml of sample, respectively) of the optimally coated D29 phage-coated BcMag tosylactivated beads. M: TrackIt 100 bp DNA Ladder (Thermofisher Scientific), −ve: negative control. Capture capabilities of different volumes (10, 15 and 20 μl) of D29-BcMag paramagnetic beads from milk samples spiked with decreasing numbers of MAP cells in comparison to peptide-mediated magnetic separation. Results indicate 15 μl beads achieve greatest capture capability and detection sensitivity.

Figure 9:
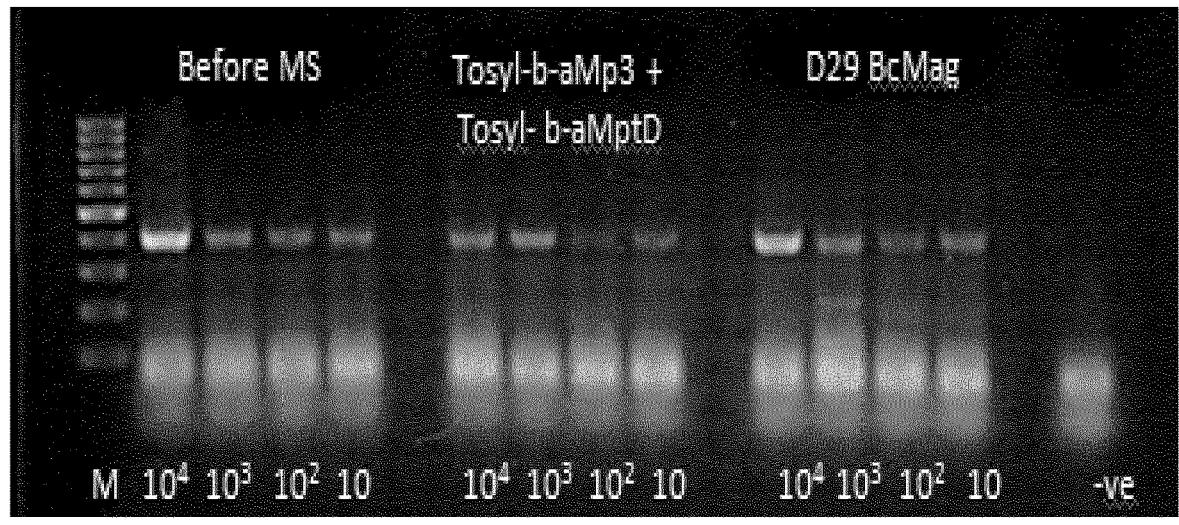

FIG. 9 'Before MS' is the original inoculum; "tosyl-b-aMp3+tosyl-b-aMptD is PMS (control); "D29 BcMag" is the novel D29-MS of the present invention. Capture of MAP by phage-coated beads was as good as, or slightly better than, peptide-coated beads, and a detection sensitivity of 10 MAP/50 ml (when the sample is milk) was achieved.

Figure 10:
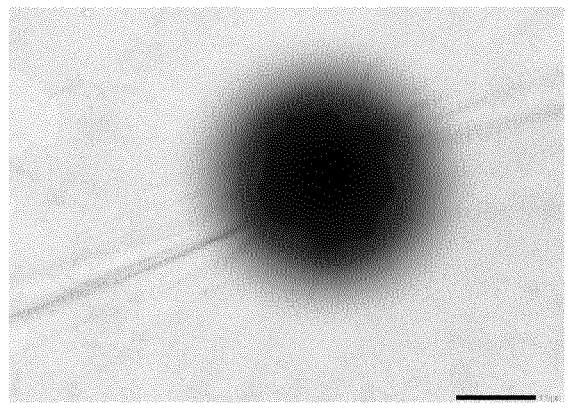
Figure 10:
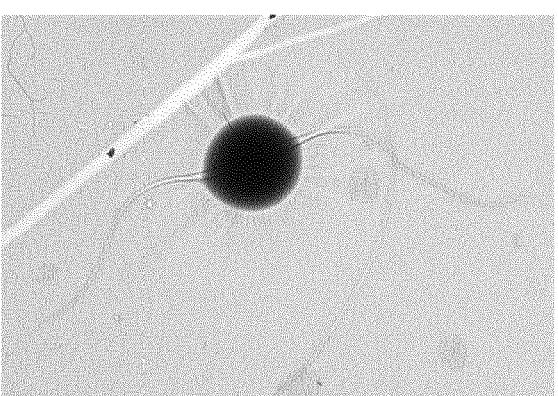
Figure 10:
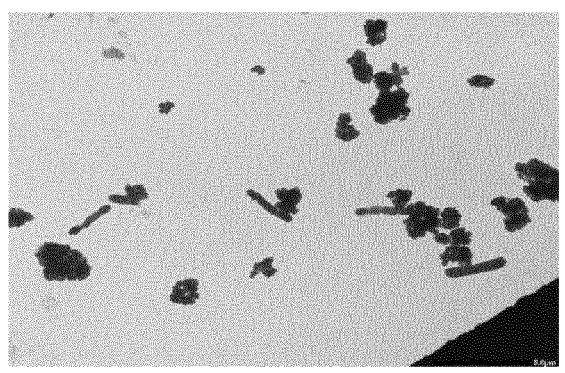
Figure 10:
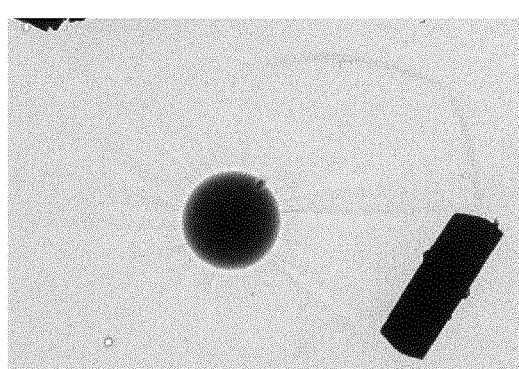
Figure 10:

FIG. 10 Transmission electron photomicrographs of: (A) BcMag tosylactivated paramagnetic beads coated with D29 phages in 'tail out' orientation; (B) multiple MAP cells captured by phage-coated beads; and (C) a single MAP cell attached to single phage-coated bead. Note: the TEM sample preparation procedure has affected the integrity of the beads, so they do not appear as uniform spheres. Electron micrographs showing D29 successfully bound to BcMag tosylactivated beads with tails oriented outwards (top row), and MAP cells captured by D29-coated beads (bottom row).

Figure 11:
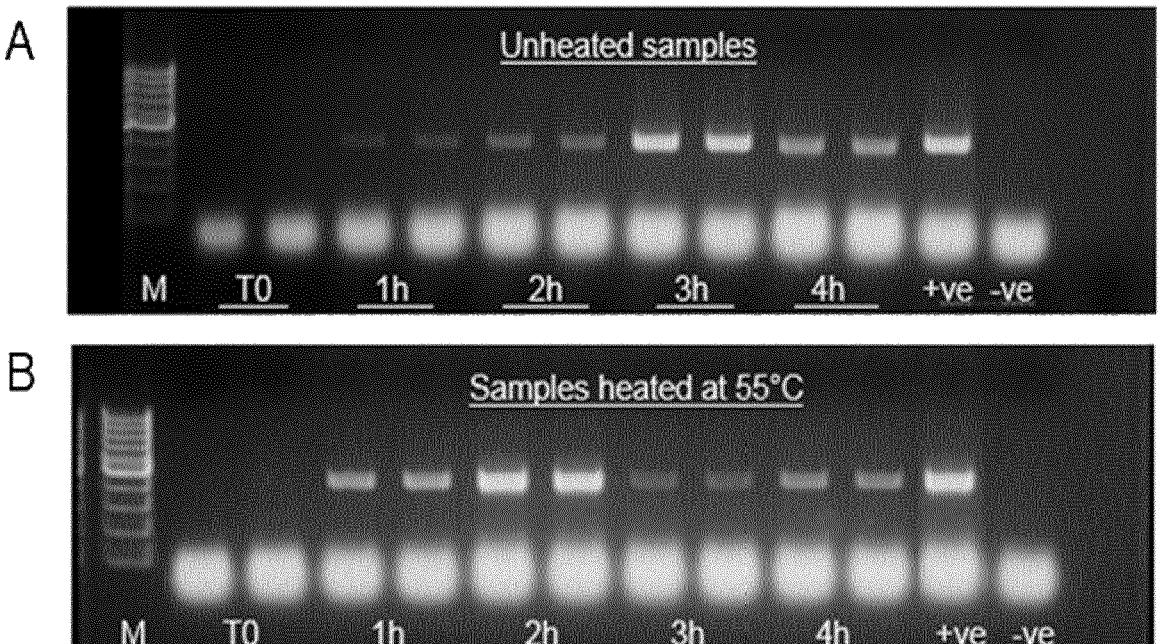

FIG. 11 Results of IS900 PCR after PhMS applied to broth suspensions spiked at $10^4$ cells/ml with viable MAP cells. After PhMS all samples were incubated at 37° C. for increasing incubation times before being subjected to IS900 PCR applied (A) without (top gel, unheated samples) and (B) with prior heating at 55° C. from 1 min (bottom gel, heated samples). M: Trackit 100 bp DNA Ladder (Thermofisher Scientific), +ve: positive MAP DNA control, −ve: negative water only control. These results demonstrate the benefit of the heat shock step in terms of earlier release of maximal DNA and hence a shorter incubation time required.

Figure 12:
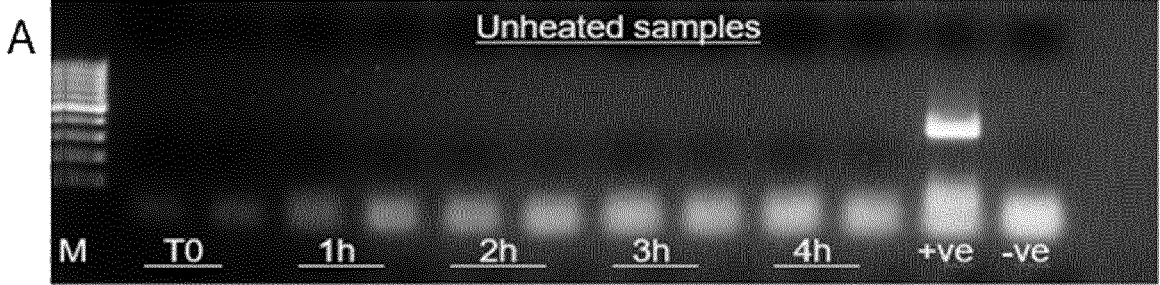
Figure 12:
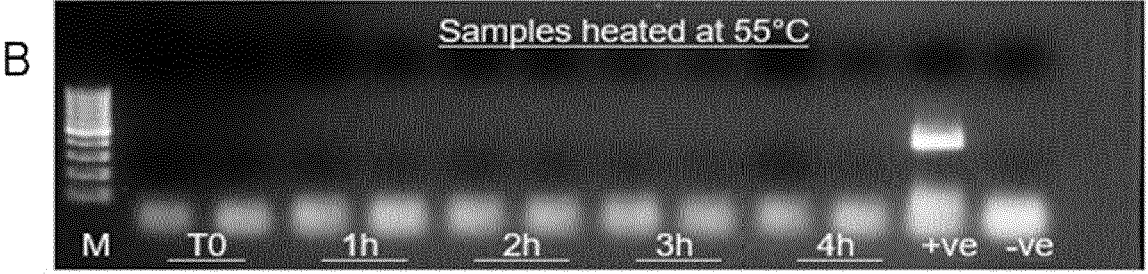

FIG. 12 Results of IS900 PCR after PhMS applied to broth suspensions spiked at $10^4$ cells/ml with gamma-irradiated (inactivated) MAP. After PhMS all samples were incubated at 37° C. for increasing incubation times before being subjected to IS900 PCR applied (A) without (top gel, unheated samples) and (B) with prior heating at 55° C. from 1 min (bottom gel, heated samples). M: Trackit 100 bp DNA Ladder (Thermofisher Scientific), +ve: positive MAP DNA control, −ve: negative water only control. No DNA was released from MAP cells that had been completely inactivated by gamma-radiation treatment, irrespective of whether a heat shock step was applied or not, demonstrating the specificity of the novel phagomagnetic—PCR test for only viable MAP.

Figure 13:
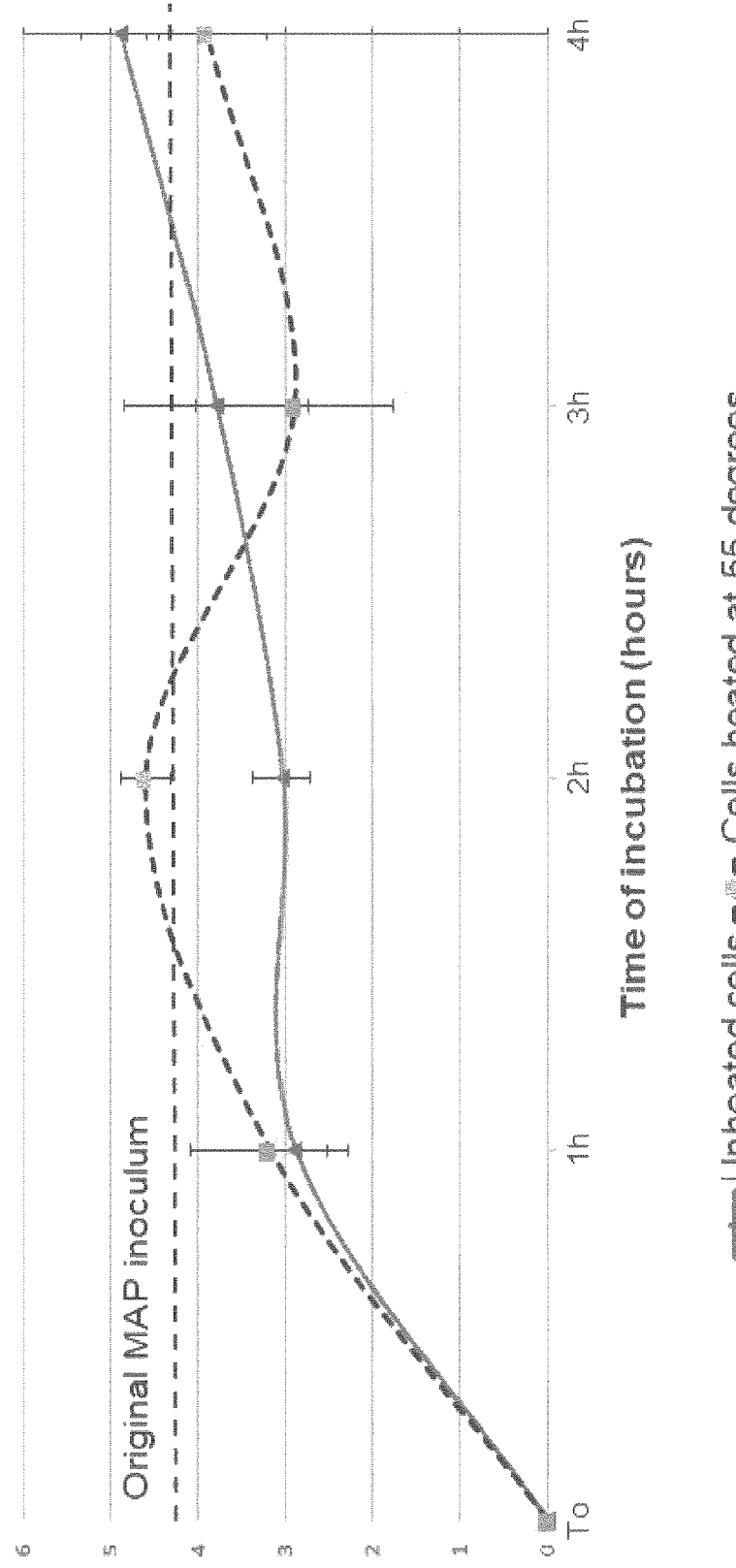

FIG. 13 Numbers of viable MAP detected by IS900 Taqman qPCR in broth suspensions spiked with MAP at $10^4$ cells/ml (indicated by dashed line) following PhMS and incubation of samples at 37° C. for 1-4 h, with (solid line) and without (dotted line) a heat treatment at 55° C. for 1 min. Results are mean $log_{10}$ MAP count/ml±standard deviation of three MAP strains tested in separate experiments. Quantitative phagomagnetic qPCR results confirming the same trends as seen in FIG. 11 in terms of quantity of DNA released over time from phage lysed MAP cells, and the benefit of the heat shock step to release maximal DNA earlier from MAP cells weakened by action of phage lytic enzymes.

Figure 14:
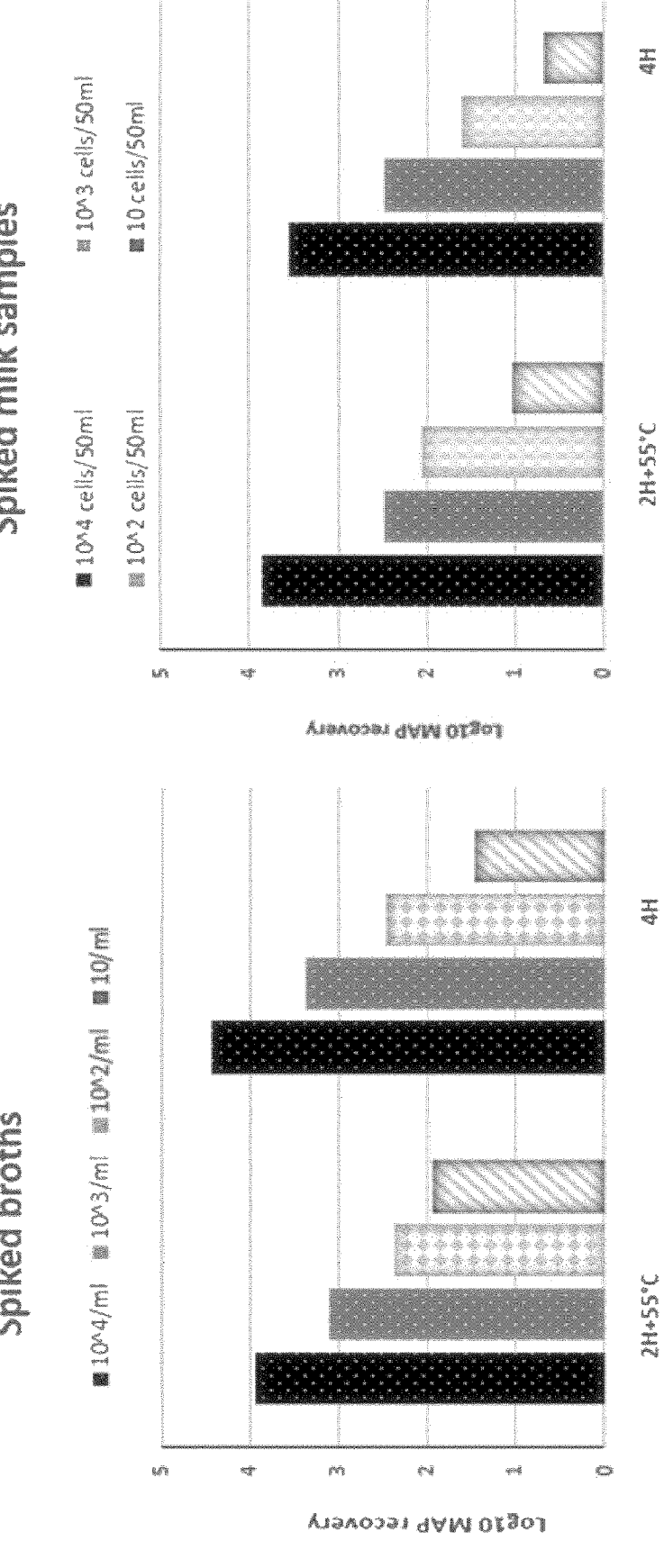

FIG. 14 Numbers of MAP detected by PhMS-qPCR assay in 7H9 broth and UHT milk samples spiked at four levels ($10^4$, $10^3$, $10^2$ and 10 cells/50 ml) with three laboratory-grown MAP strains. Before IS900 TaqMan qPCR, samples were processed through PhMS followed by incubation for 2 h or 4 h at 37° C. and a mild heat treatment at 55° C. for 1 min before qPCR. Results represent mean counts of viable MAP±standard deviation for three MAP strains tested in three separate experiments. Similar detection sensitivity demonstrated for the novel phagomagnetic qPCR assay when applied to either MAP spiked broth or MAP spiked milk.

FIG. 15A comparison of the shelf-lives of D29 phage-coated BcMag tosylactivated beads stored at 4° C. in various suspension buffers or broth. The same dilution series of MAP cells was tested using the differently stored magnetic beads on a monthly basis for up to six months. The 7H9/OADC/2 mM CaCl$_2$ broth maintained the detection capability of the D29 phage-coated beads for longer than any of the other buffers.

Figure 16:
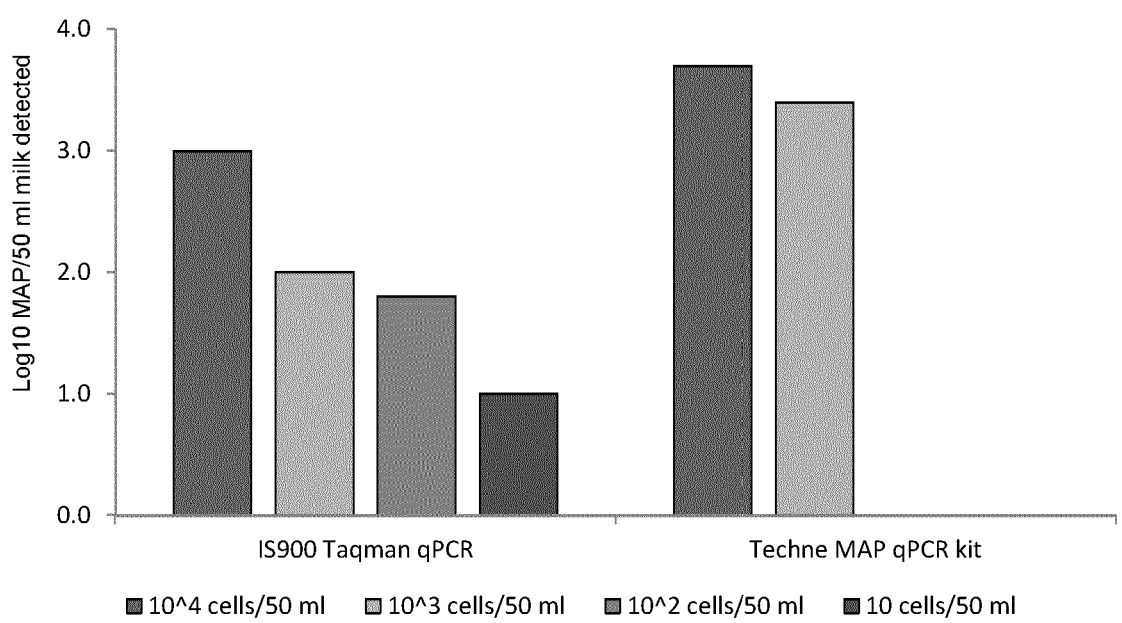

FIG. 16 Superior detection capability of an IS900 Taqman qPCR (Sidoti et al. primers and probe) applied after phagomagnetic separation of MAP cells from 50 ml spiked milk, compared to a commercially available Techne™ MAP qPCR kit.

Figure 17:
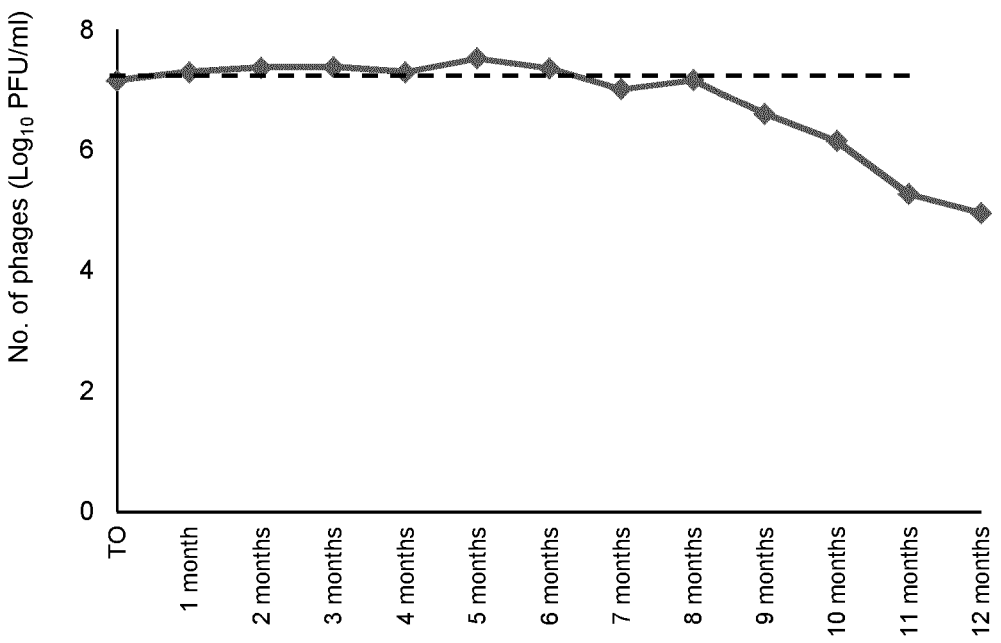

FIG. 17 Stability of D29 phage-coated BcMag tosylactivated paramagnetic beads during refrigerated storage at 4° C. for 12 months assessed by plaque assay. The number of active mycobacteriophages on the coated beads stored in 7H9-OADC-2 mM CaCl$_2$ at 4° C. remained constant for 8 months, but then declined by two $\log_{10}$ cycles by 12 months; which may potentially impact their use for the phagomagnetic-qPCR assay.

Figure 18:
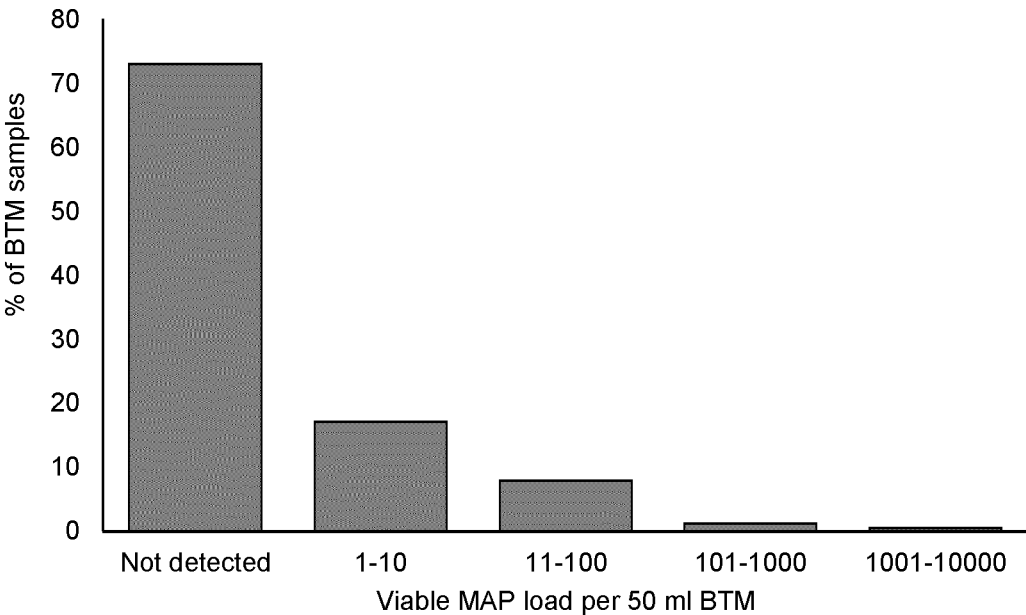

FIG. 18. Distribution of viable MAP load per 50 ml of bulk tank milk (BTM) from 392 Northern Ireland dairy farms indicated by results of the PhMS-qPCR assay. Viable MAP were detected in 26.5% of the bulk tank milks, with MAP contamination levels ranging from 1-8432 MAP/50 ml milk, however <2% of farms had MAP contamination levels >100 MAP/50 ml in their bulk tank milk.

Figure 19:
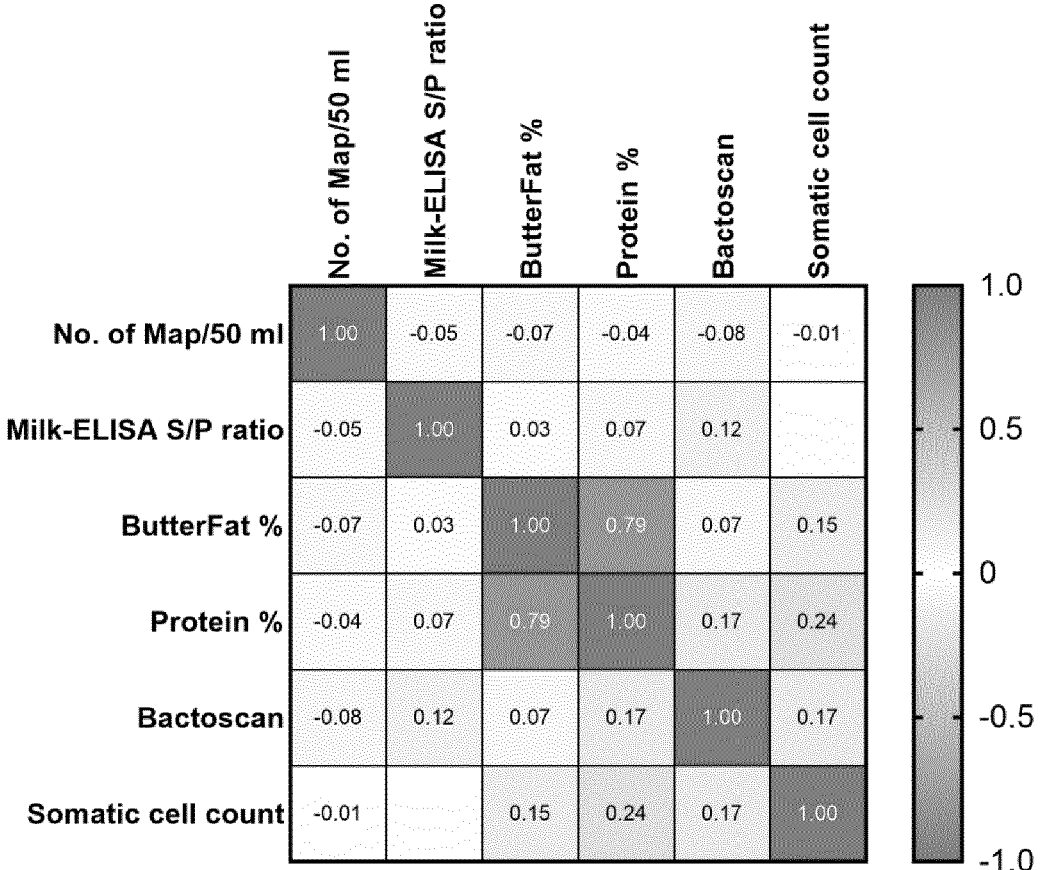

FIG. 19. Correlation coefficient matrix (heat map) for results of bulk tank milk testing. PhMS-qPCR result is 'No. of MAP/50 ml', milk-ELISA result is Milk-ELISA S/P ratio. Other results are milk recording parameters. There was no significant correlation, positive or negative, between the PhMS-qPCR result for bulk tank milks and parallel milk-ELISA result, or indeed any other milk recording test result for the bulk tank milk.

Figure 20:
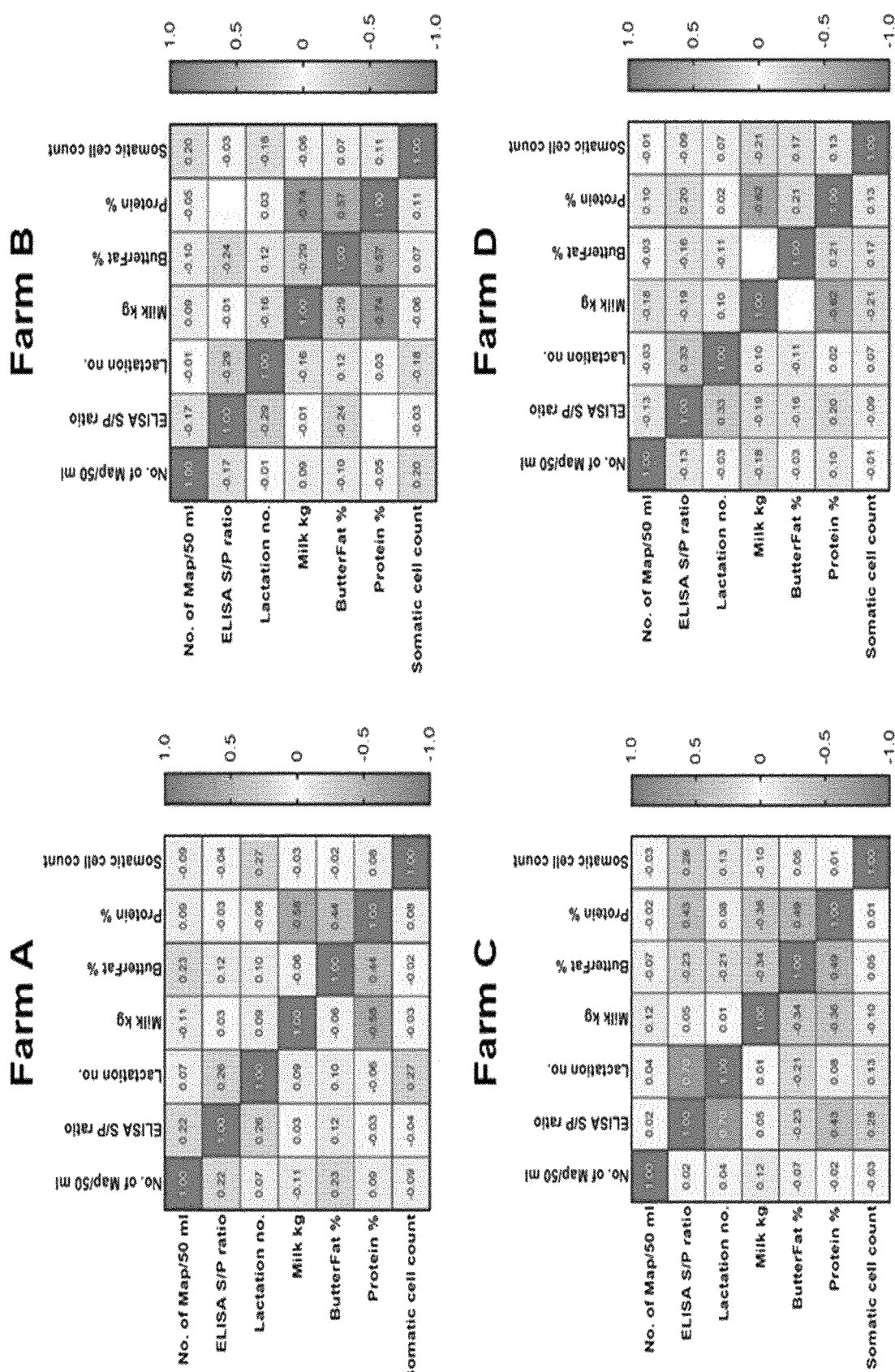

FIG. 20. Correlation coefficient matrices (heat maps) for results of individual milk testing for followed up Farms A-D. PhMS-qPCR result is 'No. of MAP/50 ml', milk-ELISA result is Milk-ELISA S/P ratio. Other results are milk recording parameters. There was no significant correlation, positive or negative, between the PhMS-qPCR result for individual milks and parallel milk-ELISA result, or indeed any other milk recording test result for milk from Farms A-D.

DETAILED DESCRIPTION OF THE INVENTION

Magnetic separation (MS) was used to capture pathogenic *Mycobacterium* species from milk using beads coated with antibodies or peptides. Viable mycobacterial cells were subsequently captured by beads coated with mycobacteriophages. The advantage of a phage assay is that it is able to detect viable mycobacterial cells quickly, unlike PCR which detects DNA of all desired cells whether living or dead.

Immunomagnetic separation (IMS) technology is a technique of capturing and enriching the desired bacterium by using modified magnetic microspheres as carriers for antibodies. In recent years, the technology has been widely used in the separation and purification of biochemical products, cell separation and purification, and microbial detection areas. Especially in the detection of pathogenic microorganisms, IMS has been increasingly widely used, the technology has been gradually applied to the relevant laboratory daily testing work.

In recent years, IMS based on magnetic microspheres has been widely used in the separation of foodborne pathogens and replacing or shortening pre-enrichment culture. However, the separation efficiency of the method is limited by the capture efficiency and diffusion rate of magnetic microbeads. The main advantages of using phagomagnetic MS, instead of IMS, rely on the use of the bacteriophages for biorecognition. Contrary to antibody generation, phages are animal-free, cost-efficiently produced by bacteria infection, taking only few hours.

A mycobacteriophage is a DNA virus able to specifically infect mycobacteria, which has been found more than 250 species in nature. Phages have strict host specificity and can only infect and replicate inside live bacterial cells. Through adsorption, penetration and other processes phages insert DNA into the host cells, subsequently relying on the host cell metabolic enzymes for progeny proliferation, the final lysis of cells due to action of phage enzymes release offspring. This is the theoretical basis of phage bio-amplification.

The present method uses beads coated with phages for magnetic separation, referred to herein as phagomagnetic MS.

However, the original phage amplification assay (PMS-phage assay) is a multi-step, rather laborious assay that doesn't lend itself well to testing large numbers of milk samples. It needs to be streamlined to offer any possibility of its future adoption for milk testing. Phagomagnetic separation, using magnetic beads coated with an appropriate mycobacteriophage to capture mycobacterial cells, offers a solution. Theoretically, the advantage would be that, once captured and infected by the lytic phages, mycobacterial cells would lyse from inside out and release their DNA after a few hours, which could then be quantified by real-time PCR.

Comparative Example 1

PMS—phage assay (see FIG. 3):

Magnetic separation using peptide-coated paramagnetic beads to selectively capture MAP cells from milk Phage amplification assay to give an indication of the number of viable MAP within 24 h IS900 PCR applied on DNA extracted from plaques to confirm that MAP DNA is present.

This method takes 48—72 hours. This is too slow for commercial use.

Example 1

Materials and Methods 1.1. Cultural of bacterial strains. Twelve MAP strains and nine other *Mycobacterium* spp. were used in this study as detailed in Table 1. MAP strains were grown for 4 to 6 weeks at 37° C. to stationary phase in Middlebrook 7H9 broth containing 10% (v/v) oleic acid-albumin-dextrose-catalase (OADC) supplement (broth from Difco) and 2 µg/ml mycobactin J (Synbiotics Europe SAS, Lyon, France). Nine non-target (non-desired) *Mycobacterium* spp. were cultivated at 37° C. to stationary phase in the same 7H9 medium without the addition of mycobactin J.

TABLE 1

Details of *Mycobacterium avium* subsp. *paratuberculosis*
(MAP) strains and non-target (or non-desired) *Mycobacterium*
spp. tested to confirm specificity of the new phage assay of
the present invention for MAP, using D29 mycobacteriophage.

| Test *Mycobacterium* sp. | Strain ID | Phage assay result |
|---|---|---|
| MAP | ATCC 19698 | + |
| MAP | NCTC 8578 | + |
| MAP | B2 | + |
| MAP | ATCC 43015 | + |
| MAP | 796 PSS | + |
| MAP | 806R | + |
| MAP | B4 | + |
| MAP | (ROI) 40 | + |
| MAP | (ROI) 5966 | + |
| MAP | (ROI) 6914 | + |
| MAP | (ROI) 4516 | + |
| MAP | (ROI) 522 | + |
| *M. smegmatis* | mc² 155 | − |
| *M. avium* subsp. *avium* | NCTC 13034 | − |
| *M. bovis* BCG | NCTC 5692 | − |
| *M. fortuitum* | NCTC 10394 | − |
| *M. gordonae* | NCTC 10267 | − |
| *M. kansasii* | NCTC 10268 | − |
| *M. smegmatis* | NCTC 333 | − |

TABLE 1-continued

Details of *Mycobacterium avium* subsp. *paratuberculosis*
(MAP) strains and non-target (or non-desired) *Mycobacterium*
spp. tested to confirm specificity of the new phage assay of
the present invention for MAP, using D29 mycobacteriophage.

| Test *Mycobacterium* sp. | Strain ID | Phage assay result |
|---|---|---|
| *M. terrae* | NCTC 10856 | − |
| *M. xenopi* | NCTC 10042 | − |

2.2. Titering of D29 phages before and after coating on beads. 10-fold dilution series of the D29 mycobacteriophage stock (containing approximately $10^9 10^{10}$ CFU/ml) were prepared in Middlebrook 7H9/10% OADC broth by adding 10 μl of the D29 stock into 90 μl broth, vortex thoroughly.

For titering D29 stock, dilute *Mycobacterium smegmatis* mc² 155 to provide a suspension of sensor cells with $OD_{600\ nm}$ of 1.0. Transfer 10 μl of $10^{-6}$, $10^{-7}$, $10^{-8}$ and $10^{-9}$ dilutions of D29 phage into four empty 9 cm Petri dishes. To each petri dish, add 1 ml *Mycobacterium smegmatis* mc² 155 culture, 5 ml Middlebrook 7H9/10% OADC/1 mM CaCl₂ broth (pre-warmed at 37° C.° C.) and, finally, 5 ml molten Middlebrook 7H9 (1.5%) agar/10% OADC was added. Once 7H9 agar is added, promptly swirl Petri dish gently five times in each direction to mix contents, then let agar solidify for 10 min before incubating plates at 37° C. overnight.

Then examine the plates for evidence of plaques (zones of clearing). Count the plaques for the dilution containing up to 300 plaques and then calculate PFU/ml of original D29 stock suspension as follows:

$$\text{No. of plaques at countable dilution} \times \text{dilution factor} \times \text{inoculum factor}$$

For titering of D29 phages after coating on four types of beads use the same method as for titering D29 mycobacteriophages before coating on beads, as described before.

2.3. Covalent coupling of D29 mycobacteriophages to four types of Tosylativated magnetic beads and Carboxyl magnetic beads. Two types of Tosylativated magnetic beads and Carboxylated magnetic beads were used in this study, as detailed in Table 3a. D29 mycobacteriophages were covalently coupled to 1 μm MyOne Tosylactivated Dynabeads, 300 nm Carboxyl-Adembeads, and 1 μm BcMag Tosylactivated magnetic beads through the amine moieties of their capsid proteins. BcMag Tosylactivated beads were used as recommended by supplier (1×) and as 10-fold concentrated (10×) suspension, to increase number of beads in 10 μl aliquot used for MS.

TABLE 3a

Comparison of the diameter, original bead concentration, and
working bead concentration of Ademtech Carboxylated, MyOne
Tosylactivated and BcMag Tosylactivated magnetic beads.

| Beads | Bead diameter | Bead concentration | No. of beads in 10 μl used for MS |
|---|---|---|---|
| Ademtech Carboxylated beads (Ademtech SA, France) | 300 nm | $11 \times 10^{12} \times 10^{12}$ beads/ml; 30 mg/ml | $3.9 \times 10^9$ |
| MyOne Tosylactivated Dynabeads (Thermo Fisher Scientific, UK) | 1 μm | $1 \times 10^{12} \times 10^{12}$ beads/ml; 100 mg/ml | $3.5 \times 10^8$ |
| BcMag Tosylactivated beads (Bioclone Inc., USA) | 1 μm | $5.1 \times 10^9$ beads/ml; 30 mg/ml | $1.8 \times 10^6$ |

The composition of the solutions used for the immobilization on MyOne beads was: 0.1 mol/L sodium borate, pH 8.5 for coating buffer; Ammonium sulphate (3 mol/L prepared in coating buffer); 0.01 mol/L sodium phosphate, 0.15 mol/L NaCl, 0.5% w/v BSA, pH 7.4 for blocking buffer; 0.01 mol/L sodium phosphate, 0.15 mol/L NaCl, 0.1% w/v BSA, pH 7.2 for washing and storage buffer.

For the immobilization of phages on Carboxyl-Ademtech 300 nm beads, the following solutions were used: 1× Ademtech Activation buffer; 0.01 mol/L sodium phosphate, 0.15 mol/L NaCl, 0.5% w/v BSA, pH 7.4 for blocking buffer; 0.01 mol/L sodium phosphate, 0.15 mol/L NaCl, 0.1% w/v BSA, pH 7.2 for washing and storage buffer.

For the immobilization of phages on 1× and 10× BcMag, 1 μm Tosylactivated beads the following solutions were used: 0.1 M sodium carbonate buffer pH 9.5 for coupling buffer; 0.01 mol/L sodium phosphate, 0.15 mol/L NaCl, 0.5% w/v BSA, pH 7.4. for blocking buffer; 0.01 mol/L sodium phosphate, 0.15 mol/L NaCl, 0.1% w/v BSA, pH 7.2. for washing and storage buffer.

Coating mycobacteriophages to MyOne tosylactivated Dynabeads Wash 35 μl of MyOne Tosylactivated Dynabeads (100 mg/ml, $1×10^{12}$ magnetic particles/ml) twice with 1 ml sodium borate buffer. Add 150 μl of the purified D29 mycobacteriophage solution ($10^{11}$ PFU/ml) to 100 μl of (NH$_4$)SO$_4$ and mix properly. Magnetic particles were incubated at 37° C. with mixing for 17 h. After incubation, remove the supernatant and place in another tube to count active phages by double agar layered conventional method. Add phage-modified magnetic particles to 1 ml PBS blocking buffer to incubate at 37° C.° C. with agitation for 2 h. Then, phage-modified Tosylactivated beads were submitted to five washing steps for 5 min at room temperature in 1 ml washing buffer. For magnetic separation use 10 μl of phage-coated MyOne Tosylactivated Dynabeads per 1 ml test sample.

Coating mycobacteriophages to Carboxyl-Adembeads Firstly, wash 35 μl of Carboxyl-Adembeads 300 nm (30 mg/ml, 1.1×10$^{12}$ beads/ml) twice in Ademtech activation buffer. Add the washed beads to 80 μl EDC (4 mg/ml) and 80 μl sulfo-NHS (9 mg/ml) to incubate for 5 h at room temperature under shaking to activate carboxylic groups on nanoparticles. Then, wash the beads twice with activation buffer, before adding 150 μl of D29 bacteriophage solution and 100 μl of activation buffer. Incubate the mix for 17 h at 37° C. with mixing (20 rpm). After incubation, remove the supernatant and place in another tube to count active phages by double agar layered conventional method. Add phage-modified magnetic particles to 1 ml PBS blocking buffer to incubate at 37° C. with agitation for 2 h. Then, phage coated beads are submitted to five washing steps for 5 mins at room temperature in PBS wash buffer, before being finally resuspended in 1 ml to use.

Coating mycobacteriophages to 1× and 10× BcMag 1 μm Tosylactivated magnetic beads When ready to coat beads, transfer 35 μl of resuspended beads (concentration 30 mg/ml in 100% isopropanol) into a microcentrifuge tube and place on a magnetic rack for 5 min. Discard isopropanol and replace with 1 ml coupling buffer (0.1 M sodium carbonate buffer pH 9.5) before vortexing beads vigorously for 1-2 min. Then, place the tube on a magnetic rack and wash with coupling buffer for 5 times. When ready to coat phages onto beads, remove the coupling buffer from the washed magnetic beads by placing tube on a magnetic rack and replace with 150 μl of D29 mycobacteriophage solution plus 850 μl 2.4. Capture of MAP from Broth Using Phage-Coated Beads Compared with Peptide-Coated Beads.

The procedure of this experiment is magnetic separation of MAP ATCC 19698 from a dilution series prepared in 7H9 broth using Ademtech 300 nm Carboxylated beads, MyOne Tosylactivated Dynabeads, 1× BcMag Tosylactivated beads and 10× BcMag Tosylactivated beads coated with D29 phages, compared to the currently used biotin-aMp3 and biotin-aMptD peptide-coated BcMag 1 μm tosylactivated beads. Magnetic separation was carried out using the Dynal BeadRetriever (Life Technologies). Magnetic capture was carried out for 30 min at room temperature under continuous mixing, followed by two washes in 1 ml Phosphate buffered saline (PBS) containing 0.05% (v/v) Tween 20 (PBS-T20, Sigma), and final resuspension of the beads in 1 ml storage buffer.

2.5. Capture of MAP from Milk Sample Using Phage-Coated Beads Compared With Peptide-Coated Beads.

In this experiment, magnetic separation of MAP ATCC 19698 from a dilution series prepared in UHT Whole Milk using MyOne Tosylactivated Dynabeads, 1× and 10× BcMag 1 μm Tosylactivated Beads coated with D29 phages, was compared to the currently used biotin-aMp3 and biotin-aMptD biotinylated peptide-coated BcMag 1 μm tosylactivated beads. The procedure was described as before for capture from broth.

Results 3.1. Covalent Coupling of D29 Mycobacteriophages on Magnetic Beads and Coupling Efficiency Study.

D29 phages were covalently coupled to three types of Tosylactivated magnetic beads and Carboxyl magnetic beads by the reaction of aminated aminoacidic moieties of the main capsid nanomeric protein.

By titering D29 phages before and after coating on four different magnetic beads, a determination of the coupling efficiency was obtained as detailed in Table 3b. For phage D29, MyOne Tosylactivated Dynabeads, 1× and 10× BcMag 1 μm Tosylactivated magnetic beads all showed near-perfect coupling efficiency of 99.9%.

TABLE 3b

Number of active D29 phages that were coated onto Ademtech Carboxylated, MyOne Tosylactivated and BcMag Tosylactivated magnetic beads.

| Type of phage-coated bead | No. phages present during coating (PFU/150 μl) | No. phages left in supernatant after coating (PFU/250 μl) | No. phages attached to beads (PFU) | Bead coating efficiency |
|---|---|---|---|---|
| D29-Carboxyl | $1.5 \times 10^8$ | $1.3 \times 10^7$ | $1.4 \times 10^8$ | 91.3% |
| D29-Tosyl | $1.5 \times 10^8$ | $2.5 \times 10^4$ | $1.5 \times 10^8$ | 99.9% |
| D29-1x BcMag | $1.5 \times 10^8$ | $<1 \times 10^1$ | $1.5 \times 10^8$ | >99.9% |
| D29-10x BcMag | $1.5 \times 10^8$ | $7 \times 10^1$ | $1.5 \times 10^8$ | >99.9% | coupling buffer. Resuspend the magnetic beads and mix very well by vortexing before placing tube on Stuart rotator mixer (10-20 rpm). Incubate the coupling reaction with continuous mixing at 37° C. overnight. After incubation, remove the supernatant and place in another tube to count active phages by double agar layered conventional method. Add 1 ml blocking buffer (PBS pH 7.4 with 0.5% (w/v) BSA) to the phage-coated beads and incubate at room temperature (21° C.) for 2 h with continuous mixing. Then, wash beads five times for 5 min with 1 ml washing buffer, with vortexing and magnetic separation between washes. Finally, resuspend the phage-coated BcMag beads in 1 ml storage buffer to reach a 1 mg beads/ml stock dilution. For magnetic separation use 10 μl of phage-coated BcMag beads per 1 ml test sample.

3.2. Capture of MAP from Broth Using Phage-Coated Beads Compared with Peptide-Coated Beads.

PCR technology was used to amplify the desired DNA for the final genosensing detection. The chosen set of primers amplified exclusively the IS900 insertion sequence, according to the agarose gel electrophoresis shown in FIG. 1. As shown in FIG. 1, 10× BcMag beads showed the strongest combination efficiency on D29. For mycobacteriophage D29, the coupling efficiency of BcMag beads was better than MyOne Tosylactivated beads and Carboxy beads, as evidenced by the brightness of the PCR product bands.

3.3. Capture of MAP from Milk Sample Using Phage-Coated Beads Compared with Peptide-Coated Beads.

In this experiment, MyOne Tosylactivated Beads and two different concentrations of BcMag beads were used to capture MAP from milk. The result for IS900PCR applied to spiked milks without prior IMS show that no target (or desired) DNA was detectable, due to PCR inhibition by milk components (FIG. 2). D29-coated 10× BcMag beads showed the best recovery of MAP after MS; similar to the result of capture of MAP from broth. The trends in capture of MAP by phage-coated MyOne Tosylactivated Beads and 1× BcMag Beads were also consistent with the results for capture of MAP from broth using these types of beads.

Examples 2 and 3—Optimised Method

Titerinq of D29 Phages Before and After Coating On Beads.

10-fold dilution series of the D29 mycobacteriophage stock (containing approximately $10^9 10^{10}$ CFU/ml) were prepared in Middlebrook 7H9/10% OADC broth by adding 10 µl of the D29 stock into 90 µl broth, vortex thoroughly.

For titering D29 stock, dilute *Mycobacterium smegmatis* mc² 155 to provide a suspension of sensor cells with $OD_{600\ nm}$ of 1.0. Transfer 10 µl of $10^{-6}$, $10^{-7}$, $10^{-8}$ and $10^{-9}$ dilutions of D29 phage into four empty 9 cm Petri dishes. To each petri dish, add 1 ml *Mycobacterium smegmatis* mc² 155 culture, 5 ml Middlebrook 7H9/10% OADC/1 mM CaCl₂ broth (pre-warmed at 37° C.° C.) and, finally, 5 ml molten Middlebrook 7H9 (1.5%) agar/10% OADC was added. Once 7H9 ager is added, promptly swirl Petri dish gently five times in each direction to mix contents, then let agar solidity for 10 min before incubating plates at 37° C. overnight.

Then examine the plates for evidence of plaques (zones of clearing). Count the plaques for the dilution containing up to 300 plaques and then calculate PFU/ml of original D29 stock suspension as follows:

No. of plaques at countable dilution×dilution factor× inoculum factor

For titering of D29 phages after coating on four types of beads use the same method with titering D29 mycobacteriophages before coating on beads, as described before. Covalent Coupling of D29 Mycobacteriophages to Four Types of Tosylativated Magnetic Beads and Carboxyl Magnetic Beads.

Two types of Tosylativated magnetic beads and Carboxylated magnetic beads were used in this study, as detailed in Table 3a. D29 mycobacteriophages were covalently coupled to 1 µm MyOne Tosylactivated Dynabeads, 300 nm Carboxyl-Adembeads, and 1 µm BcMag Tosylactivated magnetic beads through the amine moeities of their capsid proteins. BcMag Tosylactivated beads were used as recommended by supplier (1×) and as 10-fold concentrated (10×) suspension, to increase number of beads in 10 µl aliquot used for MS.

The composition of the solutions used for the immobilization on MyOne beads was: 0.1 mol/L sodium borate, pH 8.5 for coating buffer; Ammonium sulphate (3 mol/L prepared in coating buffer); 0.01 mol/L sodium phosphate, 0.15 mol/L NaCl, 0.5% w/v BSA, pH 7.4 for blocking buffer; 0.01 mol/L sodium phosphate, 0.15 mol/L NaCl, 0.1% w/v BSA, pH 7.2 for washing and storage buffer.

For the immobilization of phages on Carboxyl-Ademtech 300 nm beads, the following solutions were used: 1× Ademtech Activation buffer; 0.01 mol/L sodium phosphate, 0.15 mol/L NaCl, 0.5% w/v BSA, pH 7.4 for blocking buffer; 0.01 mol/L sodium phosphate, 0.15 mol/L NaCl, 0.1% w/v BSA, pH 7.2 for washing and storage buffer.

For the immobilization of phages on 1× and 10× BcMag 1 µm Tosylactivated beads the following solutions were used: 0.1 M sodium carbonate buffer pH 9.5 for coupling buffer; 0.01 mol/L sodium phosphate, 0.15 mol/L NaCl, 0.5% w/v BSA, pH 7.4. for blocking buffer; 0.01 mol/L sodium phosphate, 0.15 mol/L NaCl, 0.1% w/v BSA, pH 7.2. for washing and storage buffer.

Coating mycobacteriophages to MyOne tosylactivated Dynabeads Wash 35 µl of MyOne Tosylactivated Dynabeads (100 mg/ml, 1×10¹² magnetic particles/ml) twice with 1 ml sodium borate buffer. Add 150 µl of the purified D29 mycobacteriophage solution to 100 µl of (NH₄)SO₄ and mix properly. Magnetic particles were incubated at 37° C.° C. under shaking for 17 h. After incubation, remove the supernatant and place in another tube to count active phages by double agar layered conventional method. Then, phage-modified Tosylactivated beads were submitted to five washing steps for 5 min at room temperature in 1 ml washing buffer. For magnetic separation use 10 µl of phage-coated MyOne Tosylactivated Dynabeads per 1 ml test sample.

Coating mycobacteriophages to Carboxyl-Adembeads Firstly, wash 35 µl of Carboxyl-Adembeads 300 nm (30 mg/ml, 1.1×10¹² beads) twice in Ademtech activation buffer. Add the washed beads to 80 µl EDC (4 mg/ml) and 80 µl sulfo-NHS (9 mg/ml) to incubate for 5 h at room temperature under shaking to active carboxylic groups on nanoparticles. Then, wash the beads twice with activation buffer, before adding 150 µl of D29 bacteriophage solution and 100 µl of activation buffer. Incubate the mix for 17 h at 37° C. with mixing (20 rpm). After incubation, remove the supernatant and place in another tube to count active phages by double agar layered conventional method. Then, phage coated beads are submitted to five washing steps for 5 mins at room temperature in PBS wash buffer, before being finally resuspended in 1 ml to use.

Coating mycobacteriophages to 1× and 10× BcMag 1 µm Tosylactivated magnetic beads When ready to coat beads, transfer 35 µl of resuspended beads (concentration 30 mg/ml in 100% isopropanol) into a microcentrifuge tube and place on a magnetic rack for 5 min. Discard isopropanol and replace with 1 ml coupling buffer (0.1 M sodium carbonate buffer pH 9.5) before vortexing beads vigorously for 1-2 min. Then, place the tube on a magnetic rack and wash with coupling buffer for 5 times. When ready to coat phages onto beads, remove the coupling buffer from the washed magnetic beads by placing tube on a magnetic rack and replace with 150 µl of D29 mycobacteriophage solution plus 850 µl coupling buffer. Resuspend the magnetic beads and mix very well by vortexing before placing tube on Stuart rotator mixer (10-20 rpm). Incubate the coupling reaction with continuous mixing at 37° C. overnight. After incubation, remove the supernatant and place in another tube to count active phages by double agar layered conventional method. Add 1 ml blocking buffer (PBS pH 7.4 with 0.5% (w/v) BSA) to the phage-coated beads and incubate at room temperature (21° C.) for 2 h with continuous mixing. Blocking was later omitted because it reduced capture capability of D29-coated BcMag beads. Then, wash beads five times for 5 min with 1 ml washing buffer, with vortexing and magnetic separation between washes. Finally, resuspend the phage-coated BcMag beads in 1 ml storage buffer to reach a 1 mg beads/ml stock dilution. For magnetic separation use 10 µl of phage-coated BcMag beads per 1 ml test sample.

Capture of MAP from broth using phage-coated beads compared with peptide-coated beads. The procedure of this experiment is magnetic separation of MAP ATCC 19698 from a dilution series prepared in 7H9 broth using Ademtech 300 nm Carboxylated beads, MyOne Tosylactivated Dyna-beads, 1x BcMag Tosylactivated beads and 10x BcMag Tosylactivated beads coated with D29 phages, compared to the currently used biotin-aMp3 and biotin-aMptD peptide-coated BcMag 1 μm tosylactivated beads. Magnetic separation was carried out using the Dynal BeadRetriever (Life Technologies). Magnetic capture was carried out for 30 min at room temperature under continuous mixing, followed by two washes in 1 ml Phosphate buffered saline (PBS) containing 0.05% (v/v) Tween 20 (PBS-T20, Sigma), and final resuspension of the beads in 1 ml storage buffer.

Capture of MAP from milk sample using phage-coated beads compared with peptide-coated beads. In this experiment, magnetic separation of MAP ATCC 19698 from a dilution series prepared in UHT Whole Milk using MyOne Tosylactivated Dynabeads, 1x and 10x BcMag 1 μm Tosylactivated Beads coated with D29 phages, was compared to the currently used biotin-aMp3 and biotin-aMptD biotinylated peptide-coated BcMag 1 μm tosylactivated beads. The procedure was described as before for capture from broth.

Example 2—Development and Optimisation of a One-Day Phage-Based Test to Detect Viable *Mycobacterium avium* Subsp. *Paratuberculosis* (Map) in Milk The aim of this example is to optimise the current PMS-phage assay into:

Faster, one working day test

A more user-friendly format

A test with high throughput capability

BUT same analytical sensitivity as PMS-phage assay ~10 MAP/50 ml milk.

This one-day test detects MAP based on D29 bacterio-phage-mediated magnetic separation (phagomagnetic separation) combined with a MAP-specific qPCR, and is comprised of three parts:

capture of target (or desired) MAP cells by phage-coated magnetic beads

DNA release from phage-infected viable MAP cells due to phage lytic action

Detection of resultant MAP DNA by qPCR

Bacterial strains and growth conditions—Three MAP strains, including one reference strain ATCC19698, one bovine isolate B4 and the strain 796PSS originally isolated from retailed pasteurized milk (Grant et al. 2002), were used in this study. All MAP strains were grown to stationary phase in a static incubator for 2-3 weeks at 37° C. in screw cap glass vials (Cole-Parmer, UK) using 5 ml modified Middlebrook 7H9 broth (Pozzato et al. 2011), containing 0.47% 7H9 powder (Difco), 0.1% Casitone and 0.5% Glycerol (both from Sigma), 10% (v/v) Oleic Albumin Dextrose Catalase (OADC) supplement (Difco) and 2 μg/ml myco-bactin J (Synbiotics Europe SAS, Lyon, France). *Mycobacterium smegmatis* mc$^2$ 155, to be used for the plaque assay, was cultivated at 37° C. to stationary phase for 3 days in conventional Middlebrook 7H9 medium enriched with 10% (v/v) OADC supplement (Difco) without the addition of mycobactin J.

Preparation of MAP inoculum—Bacterial suspensions used to spike broths and milk samples tested in this study were prepared as previously described by Foddai and Grant (2015). Briefly, glass vials containing stationary MAP cultures were processed through ultrasonication, applied at 37 kHz for 4 min on ice in an Ultrasonic PH 30 (Fisher Scientific Ltd, Loughborough, UK) in order to disperse clumps of mycobacteria. The purity of de-clumped MAP suspensions was then verified by Ziehl-Neelsen (ZN) staining in order to ensure presence of only red acid-fast cells. The number of MAP cells per ml of broth was estimated by measuring the optical density at 600 nm ($OD_{600}$) using a WPA CO8000 cell density meter (SISLAB, Cornaredo, Italy). For each sample, optical density was adjusted to $OD_{600}$ 0·1 (approximately $10^6$-$10^7$ MAP cells per ml) followed by serial dilution of cultures in Phosphate Buffered Saline (PBS) containing 0.05% (v/v) Tween 20 (PBS-TW20, Sigma). Four spiking levels ($10^4$-$10^3$, $10^3$-$10^2$, $10^2$-10, and approximately 10 MAP per ml) were finally used to prepare the artificially contaminated broth and milk samples tested in this study to assess recovery rates of MAP by phagomagnetic separation and the new phagomagnetic separation (PhMS)-qPCR test.

Propagation of D29 mycobacteriophage—D29 mycobacteriophage (originally gifted to Prof. Irene Grant by Dr Ruth McNerney, London School of Hygiene and Tropical Medicine circa 2008) was propagated in agar plates containing *M. smegmatis* mc$^2$ 155 (also originally received from Dr Ruth McNerney). Five or six Middlebrook 7H9 agar plates containing around 200 to 300 plaques were flooded with 5 ml 7H9 broth supplemented with 10% OADC and 2 mM CaCl$_2$ then incubated overnight at 37° C., followed by another overnight incubation at 4° C. The broth containing phage particles was recovered and centrifuged at 2,500×g for 10 min, the supernatant was filtered through 0.22 μm Millex GP Millipore Express PES membrane filter units (Millipore UK Limited, Croxley Green, UK). The number of D29 phage particles present in this stock culture was determined by titration, which involved serial dilution of the phage stock in 7H9 broth and plating in Petri dishes along with 1 ml *M. smegmatis* mc$^2$ 155 culture and tempered (55° C.) molten 7H9 agar. The D29 stock solution used to prepared phage-coated paramagnetic beads was standardized to a concentration of $10^{11}$ PFU/ml and then stored at 4° C. until required.

Optimization of protocol to prepare D29 phage-coated beads—BcMag™ Tosylactivated 1 μm paramagnetic beads (Bioclone Inc., San Diego, USA) were coated with D29 phages via covalent linking with amino groups on the surface of mycobacteriophage. Phage-coated paramagnetic beads were prepared using a combination of the manufacturer's instructions and the bead coating protocol described by Laube et al. (2014) for coating paramagnetic beads with *Salmonella*-specific phages. Briefly, upon arrival in the laboratory the BcMag tosylactivated beads (150 mg) were suspended in 1.5 ml of Isopropanol (Sigma), to give a stock bead concentration of 100 mg/ml, and stored at 4° C. as recommended by the manufacturer. A portion (10 mg) of resuspended paramagnetic beads (approximately $1.7×10^9$ particles) was then washed three times with 1 ml 0.1 M Sodium carbonate/bicarbonate buffer pH 9.5, and covalently coated to D29 bacteriophages ($10^{10}$ PFU/ml) previously resuspended in 1 ml of the same buffer. Coating between paramagnetic beads and phage particles proceeded overnight (~12 h) at 37° C. with continuous mixing (30-40 rpm) on a Stuart rotator mixer (Cole-Parmer, Stone, UK). After coating, beads were captured on a magnetic rack and the supernatant was recovered and tested by the phage plaque assay to permit assessment of the efficiency of coupling by comparing PFU counts before and after coating. Impact of blocking paramagnetic beads after coating with phages with BSA was also assessed by splitting coated beads into two portions. One portion of coated beads was resuspended in PBS pH 7.4. The other portion was incubated overnight with 1 ml PBS containing 0.5% BSA, magnetically captured and finally resuspended in 1 ml PBS containing 0.2% BSA. Capture ability of phage-coated beads (10 µl) was assessed by magnetic separation (MS) carried out using the Dynal BeadRetriever (Life Technologies, Paisley, UK) and testing broth samples spiked at different levels with MAP. After MS the quantity of recovered MAP cells was subjectively assessed by conventional IS900 PCR (Millar et al. 1996, see details below) applied on DNA extracted from samples tested before and after MS by boiling at 99° C. for 25 min and centrifugation to clarify supernatant. Optimization of the amounts of phage-coated paramagnetic beads necessary to achieve the desired method sensitivity was also assessed. MS using decreasing amounts of D29 phage-coated paramagnetic beads (10 µl, 5 µl, 1 µl) was carried out on 1 ml broth samples spiked at four different levels with MAP; estimated amounts of paramagnetic beads were $1.7 \times 10^7$, $8.5 \times 10^6$ and $1.7 \times 10^6$ beads/ml of test sample, respectively. After each MS, recovery of bacteria was subjectively assessed by conventional IS900 PCR. To conclude optimization, capture ability of magnetic beads (10 mg, approximately $1.7 \times 10^9$ beads) prepared with decreasing amounts of D29 phage particles was assessed. Phage-coated beads with differing phage/magnetic bead (MB) ratios (10, 5, 1, 0.1 MAP PFU/MB) were prepared and used for MS. For each type of coated bead, efficiency of coupling was assessed by phage plaque assay test by comparing MAP PFU counts before and after coating, and recovery of MAP cells was subjectively assessed by conventional IS900 PCR.

Visualisation of the immobilized phage particles on paramagnetic particles by transmission electron microscopy (TEM)—In order to confirm that D29 phage particles had been immobilized onto the paramagnetic beads in the correct orientation for MAP capture (i.e. tail outwards), as well as demonstrate the successful capture of MAP cells after PhMS using D29 phage-coated beads, TEM was carried out. For the TEM, 10 µl of the D29-phage coated beads were washed three times in 1 ml molecular grade water (Sigma) before being diluted 1:100 in the same medium containing 2% glutaraldehyde. A small quantity of resuspended beads (10-20 µl) was coated overnight onto carbon coated EM grids (TAAB Laboratories Equipment Limited, Aldermaston, UK) at room temperature in a sealed dark box. The grids were then stained for 20 min with 2% uranyl acetate solution (TAAB Laboratories Equipment Limited) previously filtered through 0.2 µm syringe filter to remove precipitate. Excess of stain was soaked up using a Whatman filter paper and grids were finally visualized using a JEOL JEM-1400 Plus Transmission Electron Microscope (JEOL UK, Welwyn Garden City, UK) operated at 100 kV. Images were recorded using a JEOL Ruby 8 MP Bottom mounted CCD digital Camera. A similar protocol was applied to prepare post-PhMS samples for TEM, in order to visualize successful capture of MAP cells by D29 phage coated beads. Gamma-irradiated MAP broth suspensions containing $10^4$-$10^5$ MAP cells were employed for the TEM work for health and safety reasons. After PhMS samples were resuspended in molecular grade water containing 2% glutaraldehyde and processed as for D29 phage-coated beads alone.

Recovery of MAP cells by D29 phage-coated paramagnetic beads from spiked milk—Once optimal conditions for coating beads with D29 phages had been established, recovery rates of the optimal D29 phage-coated beads was assessed through testing four replicates of 50 ml UHT milk (purchased from a local supermarket) spiked with decreasing amounts of MAP cells (from 10 to $10^4$ MAP/50 ml). Before being subjected to MS, each artificially contaminated milk sample was centrifuged at 2,500×g for 15 min, cream and whey fraction were discarded and the milk pellet, which contains the vast majority of MAP bacterial load (Foddai and Grant 2015), was resuspended in 1 ml of PBS-TW20. Three different amounts of D29 phage-coated beads (10 µl, 15 µl and 20 µl/ml of resuspended milk pellet) were tested. PMS using Dynabeads MyOne Tosylactivated beads (Life Technologies) coated with two biotinylated peptides, aMp3 and aMptD (Foddai et al. 2010), was applied in parallel as a control, in order to assess which one of the three test conditions achieved similar analytical sensitivity to the existing PMS test.

Optimization of post-PhMS conditions before qPCR—This experiment was carried out in order to identify optimal post-PhMS conditions to maximize quantity of DNA released from viable MAP cells infected and then lysed by the action of the D29 phages. Broth suspensions containing approximately $10^4$ MAP cells/ml were processed through PhMS using D29 phage-coated BcMag paramagnetic beads. Following PhMS, bead samples were resuspended in 50 µl of 7H9 Middlebrook broth containing 10% OADC and 2 mM $CaCl_2$ and incubated, without shaking, for 1, 2, 3 and 4 h at 37° C. At each incubation time, samples were centrifuged at 10,000×g for 1 min and a small portion (10 µl) of the sample supernatant was processed through conventional IS900 PCR to check for the presence of DNA released from D29-infected MAP cells. In order to maximize the quantity of DNA suitable for PCR purposes, and potentially reduce the time of the test, the impact of introducing a brief, mild heat shock treatment at 55° C. for 1 min applied after each incubation time was evaluated. This mimicked the brief heat shock experienced when a phage-infected sample is plated with molten agar at 55° C. during the original phage amplification assay (Foddai et al. 2009). Quantity of DNA released from viable MAP cells infected with D29 bacteriophages was then subjectively assessed based on intensity of PCR bands achieved from heat-shocked and unheated samples. The same experiment was subsequently carried out on 1 ml broth suspensions containing approximately $10^4$ MAP cells previously subjected to a 10 kGy dose of γ-radiation to completely inactivate them, in order to verify that non-viable MAP cells did not yield any PCR products after PhMS.

Conventional IS900 PCR—Conventional IS900 PCR during the first part of this study to optimize coating protocol for D29 phage coated beads was applied as previously described by Millar et al. (1996) with some modifications. Each PCR reaction was carried out in a final volume of 50 µl containing 1× Platinum™ Green Hot Start PCR mastermix, 1 U Platinum™ Taq Green Hot Start DNA polymerase, 200 µM of each dNTP (all Thermofisher Scientific, Paisley, UK), 3 mM $MgCl_2$, 2 µM forward primer P90 (5' GAA GGG TGT TCG GGG CCG TCG GCC TTA GG 3'), 2 µM reverse primer P91 (5' GGC GTT GAG GTC GAT CGC CCA CGT GAC) and 10 µl genomic DNA extracted by heating pre- and post-MS samples at 99° C. for 25 min. PCR was carried out on a Techne™ Prime thermal cycler (Cole-Parmer), with the following conditions: 4 min of initial denaturation at 95° C., 37 cycles of 95° C. for 30 s, 59.5° C. for 30 s and 72° C. for 30 s, followed by a final elongation at 72° C. for 4 min. PCR products were visualized by agarose gel electrophoresis. The expected size of the IS900 PCR band was 394 bp.

Evaluation of three real time quantitative qPCR protocols combined with new PhMS method—Three different qPCR protocols were evaluated as potential end-point detection methods to be combined with the novel D29-based PhMS method: an IS900 SYBR Green qPCR (Bull et al. 2014), an IS900 TaqMan qPCR (Sidoti et al. 2011), and the commercially available Techne™ PrimePRO qPCR DNA detection Kit, *Mycobacterium avium* subspecies *paratuberculosis* (Techne Ltd, product code TKIT08017M) targeting the f57 gene. IS900 SYBR Green qPCR was performed as previously described by Bull et al. (2014), with minor adjustments. Briefly, each reaction was carried out on a final volume of 20 µl and containing 10 µl 2×SYBR green mastermix (SensiFAST™ SYBR® Hi-ROX Kit, Bioline Reagents Limited, London, UK), 1 µM forward primer (AV1: ATGTGGTTGCTGTGTTGGATGG), 1 µM reverse primer (AV2: CCGCCGCAATCAACTCCAG) and 2 µl template DNA. PCR conditions were: 95° C. for 10 min, followed by 40 cycles of 95° C. for 30 s, 58° C. for 1 min and 72° C. for 1 min. Standard melt curve analysis was applied at the end to evaluate the specificity of each qPCR positive reaction, consisting of 10 s at 95° C. followed by a 0.2° C./s temperature increment between 55° C. and 95° C. IS900 TaqMan qPCR was carried out as previously reported by Sidoti et al. (2011) with some modifications. Each reaction was carried out on a final volume of 20 µl and included 10 µl 2× TaqMan qPCR mastermix (SensiFAST™ Probe® Hi-ROX Kit, Bioline Reagents Limited), 1.5 µM forward primer IS900QF CCGGTAAGGCCGACCATTA, 1.5 µM reverse primer IS900QR ACCCGCTGCGAGAGCA, 6 pmoles IS900 TaqMan Probe FAM-CATGGTTATTAACGACGACGCGCAGC-TAMRA and 4 µl template DNA. PCR cycling conditions included an initial warm up section of 50° C. for 2 min, a denaturation step at 95° C. for 10 min followed by 40 cycles of 95° C. for 15 s and 60° C. for 1 min. The commercially available Techne™ PrimePRO qPCR DNA detection Kit (Techne™) gene was used following the manufacturer's instructions. Briefly, each qPCR reaction (20 microliters) included 10 µl 2×qPCR MasterMix, 1 µl MAP primer/probe mix, 1 µl internal endogenous control primer/probe mix, 3 µl RNAse/ DNAse free water and 5 µl template DNA. PCR cycling conditions involved an initial 37° C. for 10 min, denaturation at 95° C. for 2 min, followed by 50 cycles of 95° C. for 10 s and 60° C. for 1 min. All qPCR reactions were carried out using an Eco™ Real-Time PCR system (Illumina, Inc., San Diego, USA) and the associated software. A standard curve was included in each qPCR run, to permit quantitation of MAP detected. Standard curve consisted of DNA samples extracted from a serial dilution of broth suspensions containing 10 to $10^4$ MAP cells/mi.

Recovery of MAP cells from artificially contaminated milk samples—Analytical sensitivity of the new PhMS-qPCR was firstly evaluated by testing 50 ml UHT milk samples spiked at four levels ($10^3$-$10^4$, $10^2$-$10^3$, 10-$10^2$, 1-10) with MAP. A preliminary set of experiments was carried out with three MAP strains, ATCC 19698, B4 and 796PSS tested individually. In order to better estimate the limit of detection ($LOD_{50}$) of the new test a blind trial to test both spiked and non-spiked UHT milk samples was arranged. Twenty-five 50 ml UHT milk samples, including 20 samples spiked at four levels of MAP contamination (five at $10^3$-$10^4$, five at $10^2$-$10^3$, five at 10-$10^2$, five at 1-10) and five non-spiked, were included in the trial. The operator was blinded to sample details until test results became available. Test conditions used for this spiked milk analysis were: PhMS using D29 phage-coated beads, post-PhMS incubation of samples for 2 hours at 37° C., brief heat shock at 55° C. for 1 min, brief centrifugation at 10,000×g for 1 min to sediment cell debris, and IS900 Taqman qPCR applied on the DNA released from MAP cells at the end of lytic cycle.

Shelf-life of D29 phage-coated beads—The shelf-life of D29-coated BcMag™ paramagnetic beads stored at 4° C. was determined by evaluating the impact of storage for up to 1 year on MAP cell capture. Along with PBS pH 7.4, the resuspension buffer used for the first stock of D29-coated BcMag™ prepared in this study, three other storage buffers (50 mM Tris HCl pH9, 50% Glycerol and 7H9-OADC-2 mM CalCl₂ broth), was also evaluated. Four stocks of D29 coated beads resuspended in four preservation buffers were prepared and stored for up to 6 months at 4° C. with testing at monthly intervals by PhMS and conventional IS900 PCR. The MAP capture capability of each stock of phage-coated beads was assessed over time by testing broth suspensions spiked at different levels (10 to $10^4$ cells/ml) with MAP.

Maintenance of infectivity of the phage particles coated onto the paramagnetic beads was also monitored over time, to complete the shelf-life assessment of the D29 coated beads. A stock of D29 phage-coated beads stored for up to 12 months after preparation was tested monthly via plaque assay to check impact of prolonged refrigeration on D29 activity. Survival of D29 phages coated onto paramagnetic beads was estimated based on plaque forming units (PFU/ ml) generated by dilutions of coated beads being plated with *M. smegmatis* mc² 155 and molten 7H9 agar at monthly intervals during refrigerated storage.

Application of the novel PhMS-qPCR for testing bulk tank milk samples—Between September and October 2019, samples of bulk tank milk from 100 Northern Ireland dairy farms collected for milk testing purposes by Dale Farm Ltd (Belfast, Northern Ireland) were provided to QUB for MAP testing by the novel PhMS-qPCR assay. Upon arrival at the QUB laboratory, milk samples (generally ~30-40 ml) were tested immediately for viable MAP by the PhMS-qPCR assay. To aid release of MAP cells for capture, and also minimise size of cream fraction, milk samples were pre-warmed at 37° C. for 10 min in a water bath before centrifugation at 2,500×g for 15 min. After centrifugation the cream and whey fractions were discarded, and the pellet fraction was resuspended in 1 ml of PBS-TW20 and tested for MAP. After PhMS, bead samples were incubated at 37° C. for 4 h (rather than the 2 h used for laboratory-grown MAP) before mild heat shock treatment and subsequent IS900 qPCR. Based on some preliminary observations, this 4 h incubation time was found to be more appropriate for MAP in naturally infected milk samples, particularly when testing samples previously subjected to prolonged refrigeration before delivery. The quantity of MAP detected by qPCR per 30-40 ml milk volumes was corrected to quantity of MAP per 50 ml milk (the more usual manner in which MAP counts in milk are expressed), to permit comparisons between results for the variable volumes of BTM tested.

Statistical analysis of results—The statistical significance of differences between mean plaque counts observed (a) before and after coating of beads and (b) before and after prolonged storage at refrigeration temperature during the shelf life experiments, was assessed by a paired t test using GraphPad Instat software (GraphPad Inc., San Diego, USA); results were statistically significant when P value was <0.05. $LOD_{50}$ and associated 95% confidence limits of new PhMS-qPCR assay was estimated using the generalized Spearman-Karber $LOD_{50}$ calculation for four-level spiking protocols (AOAC International 2006).

Optimization of protocol for preparation of D29 phage-coated beads—Covalent immobilization of D29 phage particles onto paramagnetic beads was assessed by coupling phage particles (approximately $10^{10}$ PFU/ml) to 10 mg of BcMag™ tosylactivated beads and then evaluating the phage concentration before and after the immobilization step. PFU counts repeatedly showed significant 3 $\log_{10}$ PFU/ml decreases (P value=0.00066, paired t-test) after coating, thus demonstrating successful immobilization of phage particles onto the paramagnetic beads by adopting the Laube et al. (2014) protocol. Mean coupling efficiency, obtained by comparing PFU counts before and after coupling for phage-coated paramagnetic beads, was 99.93±0.02%.

A high level of MAP recovery was observed when PhMS using the phage-coated beads was applied to broth spiked at four levels with MAP. Comparison of IS900 PCR results for samples tested before and after PhMS indicated successful recovery of MAP from all the spiking levels when D29 phage-coated BcMag™ tosylactivated beads not previously blocked with BSA were employed. As shown in FIG. 7, the analytical sensitivity of the novel phage-magnetic separation was visually similar to that of samples subjected to PMS. In contrast, when phage-coated beads were blocked with BSA, as suggested in the bead manufacturer's instructions, the capture capability of the phage-coated beads was substantially diminished. The amount of paramagnetic beads used for each PhMS was also found to be a crucial factor to maximize capture sensitivity. PhMS using 10 µl (10 mg) D29 phage-coated beads (equivalent to $1.7 \times 10^7$ beads/ml test sample) showed the optimal capture sensitivity and demonstrated successful recovery from all the spiking levels. Use of lower amounts of paramagnetic beads (5 µl and 1 µl/ml sample) was found to adversely affect the detection sensitivity of PhMS (FIG. 6). A similar trend was observed for PhMS carried out using beads prepared with lower phage/MB ratios. Paramagnetic beads coated with $10^{10}$ PFU/ml bacteriophage (10 PFU/MB) showed the highest MAP detection capability and use of lower phage/MB ratios (5, 3, 1 and 0.1 PFU/MB) adversely impacted sensitivity of the test. The lowest detectable number of MAP from spiked broths captured using paramagnetic beads prepared with decreasing PFU/MB ratios was 1-10 MAP/ml for 10 PFU/MB ratio, 10-100 MAP/ml for 5 PFU/MB ratio and $10^2$-$10^3$ MAP/ml for 3, 1, and 0.1 PFU/MB ratios, respectively (FIG. 5).

Recovery of MAP cells from spiked milk by optimally coated beads—Once the optimal conditions for coating phages onto paramagnetic beads had been established, an experiment was carried to assess recovery of MAP from UHT milk samples spiked at four levels with MAP using optimally coated D29-phage beads. Three different quantities of D29 phage-coated beads (10 µl, 15 µl and 20 µl) were tested to identify the quantity required per sample for optimal recovery of MAP cells from milk. As shown in FIG. 8, similar detection sensitivity was observed for the three different quantities of D29 phage-coated beads compared. MAP was successfully detected from all the spiking levels in all cases. However, the appearance of PCR bands for samples subjected to PhMS using 15 µl of phage-coated beads indicated a slightly higher intensity in samples spiked at the highest level followed by a more gradual reduction of the intensity of the PCR bands in all the other samples at lower MAP spiking levels. The appearance of the PCR bands suggested greater recovery of MAP cells when 15 µl of phage-coated beads, rather than 10 µl, were used for PhMS. Use of a higher quantity of beads (20 µl/ml of resuspended milk pellet) did not result on any apparent improvement in MAP capture capability.

Summary:

A—The Optimal Quantity of D29 Phages to Coat onto BcMaq Tosylactivated Beads for Maximal MAP Cell Capture—10 PFU/Bead—See FIG. 5.

'Before MS' are the control samples, against which capture capability of different types of coated bead was compared—results clearly indicate a PFU/bead ratio of 10 PFU/bead is optimal as all four MAP cell concentrations are still detectable and PCR bands are of similar intensity at all four concentrations, whereas, at other coating ratios, fewer and fewer MAP cell concentrations test PCR positive.

B—Quantity of D29 Phage-Coated Beads/ml Required for Optimal MAP Capture—see FIG. 6

'Before MS' are the control MAP cell concentrations tested by PCR directly, against which capture capability of three different coated bead concentrations are compared. Results indicate that a bead concentration of $1.7 \times 10^7$ beads/ml is optimal for MAP capture, while lower bead concentrations will miss lower MAP concentrations, i.e. won't have sufficient detection sensitivity.

C—Should Phage-Coated Beads be Blocked Before Use for Magnetic Separation, as Per BcMaq Bead Coating Instructions?—see FIG. 7

The results in FIG. 7 clearly indicate that phage-coated BcMag tosylactivated beads should not be blocked with PBS-BSA, as unblocked beads demonstrated superior MAP capture capability than blocked phage-coated beads, and also than blocked peptide-coated tosylactivated beads.

D—What Volume of Phage-Coated Beads to Use Per Sample for Maximal Capture of MAP from Milk?—See FIG. 8

10 µl peptide-coated beads had been used for PMS, but results indicated that 15 µl phage-coated beads gave PCR bands of superior intensity across the four MAP cell concentrations tested.

E—Capture of MAP from Spiked Milk Using Optimised D29 Phage-Coated Beads Compared to Existing Peptide-Mediated Magnetic Separation (PMS) Method—see FIG. 9

'Before MS' is the original inoculum; "tosyl-b-aMp3 +tosyl-b-aMptD is PMS (control); "D29 BcMag" is the novel D29-MS of the present invention. Capture of MAP by phage-coated beads was as good as, or slightly better than, peptide-coated beads, and a detection sensitivity of 10 MAP/50 ml (when the sample is milk) was achieved.

F—Electron Microscopy Evidence of D29 Phages Successfully Attached to BcMaq-Tosylactivated Beads in Correct Orientation and Capture of MAP Cell by Phage-Coated Bead—See FIG. 10

TEM of Phage-Coated Beads

FIG. 10 shows the results of TEM, confirming immobilization of D29 phage particles onto paramagnetic beads in the correct orientation with phage tails pointing outwards from the solid support, and also successful capture of target MAP cells by PhMS. Phage tails clearly visible radiating from magnetic bead and MAP cells clearly attached to phage tails—see FIG. 10.

G—Optimizing Post-MS Conditions to Achieve Maximal DNA Release from Phage-Infected MAP Cells—See FIG. 11

Optimization of Post-PhMS Conditions to Maximize Release of MAP DNA

Our aim was to identify the steps required post-PhMS in order to maximize the quantity of DNA released from viable MAP cells incubated over time with D29-phage coated beads. The intensity of PCR bands was subjectively assessed at the end of each hour of incubation post-PhMS, with and without a brief heat shock at 55° C. for 1 min. Results indicated an increasing quantity of DNA detected over time, as was expected, with maximum quantity of DNA observed after 2 and 3 h of incubation at 37° C. in the presence and absence of the heat shock treatment, respectively (FIGS. 11A and B). After the 2 and 3 h time points, an apparent reduction in PCR signal was observed, which may indicate adverse effect of phage restriction enzymes on MAP DNA, potentially reducing integrity of DNA molecules suitable for PCR amplification. The brief heat shock clearly had a positive effect on the release of DNA (FIG. 11B), presumably because phage-weakened MAP cell walls lysed more easily, and the maximum quantity of DNA was released after 2 h rather than 3 h. This suggested that the addition of this brief heat shock had the potential to reduce the overall time of the PhMS-qPCR assay. No PCR bands were ever observed from samples processed immediately after PhMS (T0), confirming that the mild heating step alone was not sufficient to lyse MAP cells. The DNA detected at the end of the test only came from viable MAP cells infected with D29 bacteriophages that had burst as a result of the lytic cycle.

During MS, phages bind to and then infect the MAP cells. The lytic cycle proceeds within viable MAP cells until lysis occurs releasing progeny phages but also MAP DNA. The intensity of the bands in FIG. 11 indicates when maximal amounts of MAP DNA are released post-MS during incubation of samples at 37° C. for up to 4 h. We decided to test effect of a brief heat shock, mimicking the heat shock experienced by phage-infected MAP cells in the conventional phage assay when samples are plated with molten agar at 55° C. Inclusion of the heat shock step speeded up release of MAP DNA and hence would shorten the overall test time by 1 h.

H—Same Experiment (as G above) Done with Radiation-Killed MAP cells—Results Demonstrate the Absence of any Released DNA even after 55° C. Heat Shock—See FIG. 12

Confirmation that the PhMS-PCR assay only detects viable MAP—In order to assess the specificity of the new test for viable MAP cells, the above experiment was repeated with broth samples spiked ($10^3$-$10^4$ MAP/ml) with a radiation-killed MAP cell suspension. DNA release was monitored over time during incubation at 37° C. following PhMS and with and without a brief heat shock at 55° C. for 1 min. No PCR bands were observed for either non-heated or heat-shocked samples (FIG. 12). Thus, it was demonstrated that D29 bacteriophage can only complete its lytic cycle within viable MAP cells, and that DNA detected at the end of the PhMS-qPCR assay is a reliable indicator of viable MAP being present in the original sample.

This experiment was exactly the same as Experiment G, except that a gamma radiation-killed MAP culture was tested. There was absolutely no evidence of any MAP DNA release, even with the 55° C. heat shock. This demonstrated that our test is specific for detection of viable MAP.

I—When Optimised Phage Capture and Lysis of MAP Cells was Combined with a MAP-Specific qPCR Same Results Obtained—Maximal Release of MAP DNA 2 h Post-MS when Brief Heat Shock at 55° C. For 1 Min is Included, Otherwise 3-4 h Post-MS—See FIG. 13

Combine optimized phage-mediated MAP capture and lysis with quantitative qPCR—Three different qPCR methods were evaluated to assess which should be combined with the novel phagomagnetic separation method. Application of IS900 Taqman qPCR provided clearer information about the quantity of DNA from detected MAP cells and showed superior detection rates than the other two qPCR protocols applied in parallel. The novel PhMS method was initially employed in combination with IS900 TagMan qPCR to test recovery of MAP DNA from broth suspensions spiked at high level ($10^4$ MAP/ml) with three different lab-grown MAP strains originally isolated from milk. Results indicated close to 100% MAP recovery after 3 h of incubation at 37° C. post-PhMS (FIG. 13). Slightly higher numbers of MAP were consistently detected from all the three MAP strains 1 h earlier (after 2 h incubation instead of 3 h at 37° C.) if samples were briefly heat shocked at 55° C. for 1 min at the end of the 2 h incubation period, to lyse MAP cells already weakened by phage lytic action.

J—Demonstration of Sufficient Analytical Sensitivity and Quantitation Capability of New Phagomagnetic-qPCR Assay By Testing MAP-spiked Broth And Milk—See FIG. 14

A second round of experiments was carried out to assess the analytical sensitivity of the test to detect MAP in 50 ml 7H9 broth and UHT milk samples spiked at four levels (10 to $10^4$ MAP/50 ml). Two versions of the test involving incubation post-PhMS at 37° C. for 2 h (quick version) and 4 h (long version), followed in both cases by a mild heating at 55° C. for 1 min and IS900 Taqman qPCR, were tested in parallel for comparison. Results of experiments carried out with three MAP strains demonstrated successful detection of 10 MAP cells/50 ml of broth or milk in both cases, and no significant difference in detection sensitivity (P value=0.940319, paired t-test) between the two versions of the test (FIG. 14). A lower level of detection was observed for the other two qPCR protocols applied in parallel to IS900 TagMan qPCR. A higher detection limit (>100 MAP/ml broth or/50 ml milk) was achieved with the commercially available Techne qPCR kit (data not shown), possibly due to the lower number of copies of the f57 gene in MAP genome compared to IS900. No DNA amplification was observed when IS900 SYBR Green was used in combination with PhMS (data not shown), possibly due to OADC or $CaCl_2$ in the bead suspension buffer inhibiting the SYBR biochemical reaction.

Most of the optimization work was done on MAP spiked broth. This parallel testing of both MAP spiked broth and milk demonstrated that the novel test was equally applicable for milk testing and that the target (or desired) detection sensitivity of 10 MAP/50 ml was achievable.

Figure 15:
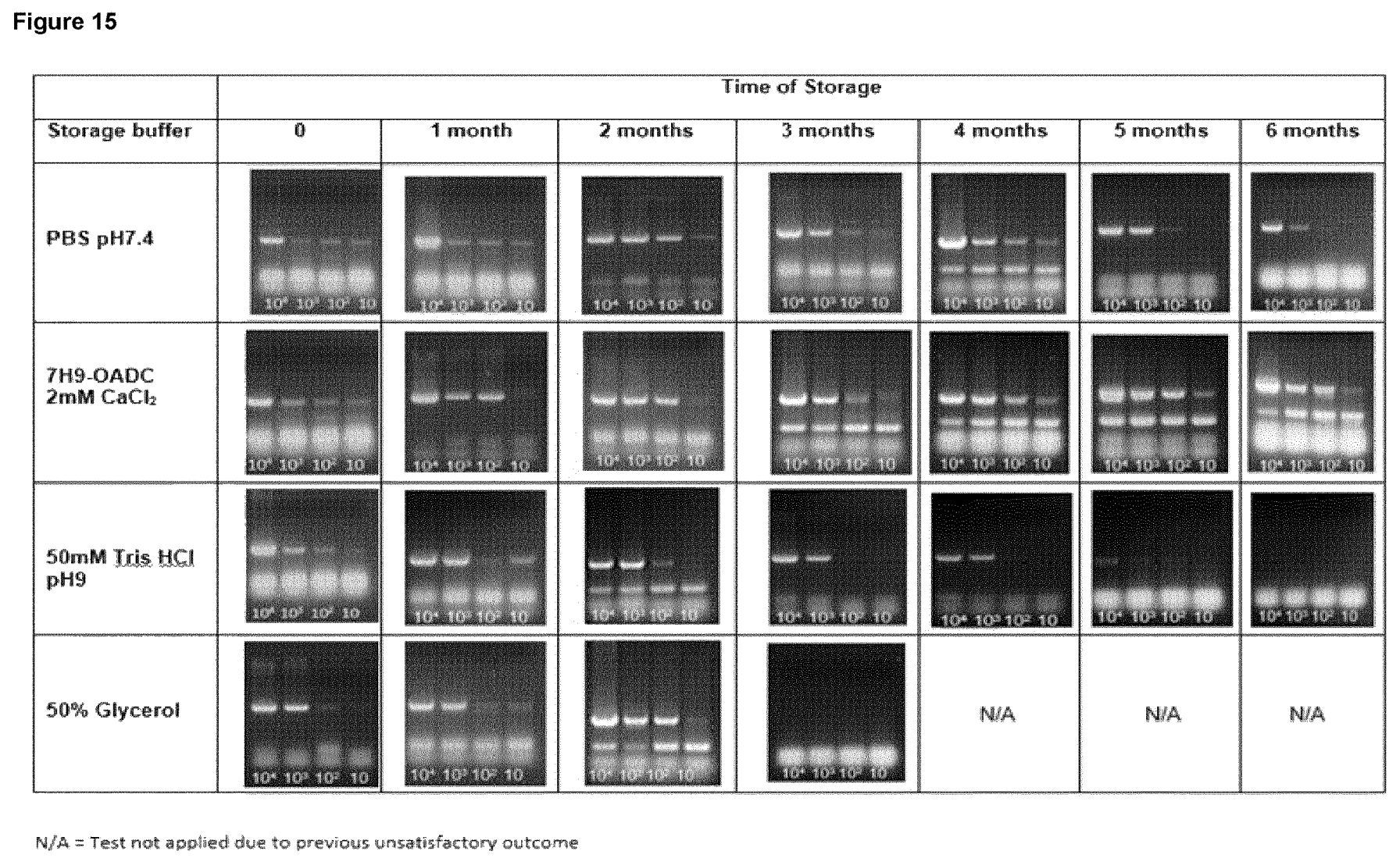

K—Determination of Shelf-Life of D29 Phage-Coated BcMag Tosylactivated Magnetic Beads Stored at 4° C.—see FIG. 15

With a view to the phage-coated beads eventually becoming part of a commercial test, we assessed which storage buffer would maximize the shelf-life of phage-coated beads without loss of detection capability—storage of beads in 7H9-OADC-2 mM $CaCl_2$ broth maintains phage activity for at least 6 months. Phage activity diminished to varying degrees in three other storage buffers tested.

FIG. 17 is essentially a follow-on shelf life study in the best storage buffer (7H9-OADC-2 mM $CaCl_2$). FIG. 17 shows that the phage-coated beads are stable for at least 8 months at 4° C., after which there was evidence of some decline in numbers of viable D29 phage present on the beads. Of the four different storage buffers tested (PBS pH7.4, 50 mM Tris-HCl pH 9, Glycerol 50% and 7H9-OADC-2 mM $CaCl_2$ broth), only the D29 phage-coated beads stored in 7H9-OADC-2 mM $CaCl_2$ broth maintained their MAP capture capability and demonstrated recovery of MAP cells from all four spiking levels tested, even after 6 months of storage at 4° C. The bead stocks resuspended in the three other storage buffers showed visible drop off in capture capability after a couple of months of storage (data not shown). A new stock of D29 phage-coated beads was prepared and stored in 7H9-OADC-2 mM $CaCl_2$ at 4° C. and tested monthly for 12 months through the plaque assay. Phage numbers remained constant for 8 months at 4° C., but then progressively declined over the next 4 months of storage by 2 $\log_{10}$ (FIG. 17).

Based on these data, a CaCl$_2$-containing broth is the preferred storage buffer; and 7H9-OADC-2 mM CaCl$_2$ broth is a preferred CaCl$_2$-containing broth.

L—Selection of the Most Appropriate qPCR Method to Combine with Phagomagnetic Separation—See FIG. 16

A published MAP-specific Taqman probe-based IS900 qPCR method (Sidoti et al "Validation and standardization of IS900 and F57 real-time quantitative PCR assays for the specific detection and quantification of *Mycobacterium avium* subsp. *paratuberculosis*. *Can J Microbiol*. 2011 May; 57(5):347-54. proved to be superior to a commercially available MAP qPCR kit from Techne™, in terms of both detection sensitivity and MAP enumeration potential. The IS900 Taqman method recognizes an insertion element IS900 as the signature DNA sequence. The Techne kit is devised to recognize the unique gene sequence f57 for *Mycobacterium avium* subsp. *paratuberculosis* (MAP) as the signature DNA sequence.

M—Detection Sensitivity of the New PhMS-qPCR Test

Blind testing of artificially contaminated UHT milk samples was carried out to determine detection sensitivity and specificity of the test for MAP. A total of 25 UHT milk samples, including 20 samples spiked with MAP at four different levels (five spiked with $10^3$-$10^4$ MAP/50 ml; five spiked with $10^2$-$10^3$ MAP/50 ml; five spiked with 10-$10^2$ MAP/50 ml and five spiked with 1-10 MAP/50 ml) and five non-spiked milk samples, were tested. MAP was successfully detected in all five samples spiked at $10^3$-$10^4$ MAP/50 ml and $10^2$-$10^3$ MAP/50 ml, but in only 3 out of 5 samples spiked with both 10-$10^2$ MAP/50 ml and 1-10 MAP/50 ml. No viable MAP cells were detected in any of the five non-spiked UHT milk samples. Estimated limit of detection 50% (LOD$_{50\%}$) was calculated to be 10.004 (95% CI: 1.20-82.83) MAP cells/50 ml using the online Excel LOD$_{50\%}$ calculator.

N—PhMS-qPCR Testing of BTM Samples

Analysis of BTM samples confirmed that the PhMS-qPCR assay was a sensitive test for viable MAP. Forty-nine (49%) of the 100 BTM tested PhMS-qPCR positive for viable MAP, with the number of viable MAP detected ranging from 3 and 126 MAP/50 ml. The vast majority (71%) of the MAP positive BTM samples contained between 1-10 MAP/50 ml milk. The limited volumes of BTM available for testing meant that culture could not be carried out in parallel with the phage-based assay in order to confirm the presence of viable MAP in PhMS-qPCR positive milk samples.

Discussion

Bacteriophages can be used in various ways for the detection of pathogens (Schmelcher and Loessner 2014). The most common lytic phage-based test is the phage amplification assay, or simply the plaque assay. The original FASTPlaqueTB assay for *Mycobacterium tuberculosis* and the PMS-phage assay for MAP are examples of phage amplification assays. Both tests rely upon phage-infected mycobacterial cells being plated with molten agar and fast-growing *M. smegmatis* before the lytic cycle of the phage is completed. When phage-infected *M. tuberculosis* or MAP cells burst in situ within the agar they release progeny phages which create a plaque (zone of clearing) around the initiator *M. tuberculosis* or MAP cell (or clump) by repeatedly infecting and bursting *M. smegmatis* cells in the surrounding lawn. Unfortunately, due to the fact that the D29 phage can infect a range of *Mycobacterium* spp. (Rybniker et al. 2006) in addition to *M. tuberculosis*, MAP and *M. smegmatis*, the observation of plaques is not definitive proof of the presence of viable *M. tuberculosis* or MAP in a sample. DNA must be harvested from some plaques and target pathogen-specific PCR performed to confirm this. In contrast, for the new PhMS-qPCR assay reported here, the lytic D29 phage was immobilised on tosylactivated paramagnetic beads to be used for phage-mediated capture of MAP cells and, once captured, phage infection of MAP cells would have been initiated also.

To our knowledge, the only other published PhMS assay is a method using phage P22 coated onto tosylactivated M-280 Dynabeads to capture *Salmonella Typhimurium* cells, before detection in an immunoassay format using specific anti-*Salmonella* antibodies conjugated to horseradish peroxidase as an optical reporter (Laube et al. 2014). These authors did not choose to take advantage of the fact that phage-captured *Salmonella* cells would subsequently be lysed due to P22 phage action. In contrast, for our novel assay, we did choose to wait for cell lysis to occur naturally, so that a test for viable MAP would be achieved. Only viable MAP cells will support amplification of the D29 phage internally resulting in subsequent lysis. Thus, for our test, PhMS of MAP from milk was followed by an incubation period at 37° C. to allow amplification of D29 phages within the infected MAP cells, to the point that the cells burst from within by action of phage endolysins and host cell DNA was released and became available for qPCR confirmation and quantitation of MAP. We found that inclusion of a brief heat shock (55° C. for 1 min) at the end of incubation, mimicking the temperature of molten agar during plating in the PMS-phage assay, aided the earlier, maximal release of DNA from phage-weakened MAP cells (FIGS. 11 to 13).

Table 4 provides a summary of the key differences between our previous PMS-phage assay and the new PhMS-qPCR assay.

TABLE 4

| Summary of the differences between PMS-phage and PhMS-qPCR assays. | |
|---|---|
| PMS-phage assay (Foddai and Grant 2017) | PhMS-qPCR assay (This study) |
| Peptides used to capture MAP cells and phage assay carried out subsequently | Phages used to both capture and infect MAP cells simultaneously |
| FAS treatment needed to inactivate exogenous seed phage | Not required; presence of phages on magnetic beads is irrelevant to test outcome |
| Plating of sample with *M. smegmatis* and molten 7H9 agar required | Not required; endpoint of test is no longer plaque formation but qPCR |
| Brief heat shock when sample is plated with tempered (55° C.) molten agar | Brief heat shock (55° C./1 min) applied to aid earlier MAP cell lysis |
| MAP cells burst within agar necessitating | MAP cells burst to release DNA into 50 μl |

TABLE 4-continued

Summary of the differences between PMS-phage and PhMS-qPCR assays.

| PMS-phage assay (Foddai and Grant 2017) | PhMS-qPCR assay (This study) |
|---|---|
| extraction of DNA from plaques before PCR Plaques after overnight incubation can be counted, but confirmation they are due to MAP requires plaque PCR | volume, so no other DNA extraction required IS900 Taqman qPCR permits specific detection and quantitation of MAP |
| DNA from only 10 plaques is typically harvested, irrespective of plaque number observed | Viable MAP cells in entire sample contribute towards template DNA available for qPCR |
| Total assay time is 24-48 h | Total assay time is ~7 h |

In the course of test development, a number of things needed to be confirmed/optimised in order to maximise subsequent MAP cell capture, including confirming correct phage orientation on the paramagnetic bead surface by TEM, bead to phage ratio to use during bead coating, number of phage-coated beads to add per PhMS reaction and optimal storage buffer for coated beads. The results presented in FIGS. 5, 6, 7, 8 and 10 should clearly demonstrate our decision-making in relation to these parameters, on the basis of conventional IS900 PCR testing immediately after PhMS. We had previously used this subjective evaluation approach to successfully optimise MS methods for MAP (Foddai et al. 2010b, O'Brien et al. 2016) and *Mycobacterium bovis* (Stewart et al. 2012). Our objective was to achieve similar or better MAP capture capability and detection sensitivity with the D29 phage-coated BcMag tosylactivated beads as we had previously with biotinylated peptide-coated tosylactivated Dynbeads, and we have done this (FIGS. 7 and 8). We also demonstrated that only viable MAP cells can support phage amplification, and consequently be lysed by phage action during the incubation period following PhMS to contribute DNA for qPCR purposes (FIGS. 11 and 12). Furthermore, we showed that the brief heat shock at 55° C. for 1 min did not contribute enough heat to lyse non-viable MAP cells in a sample (FIG. 12B); which is a vitally important consideration in terms of specificity of the PhMS-qPCR assay for viable MAP only.

Real-time qPCR was selected as the endpoint detection method after PhMS because it provides rapid and quantitative results. We evaluated three different qPCR endpoint detection options to combine with PhMS—two published IS900 qPCR assays (one SYBR green-based (Bull et al. 2014), the other Taqman probe based (Sidoti et al. 2011)) and a commercially available qPCR kit for MAP targeting f57 rather than IS900. All three methods had quantitation potential so long as a standard MAP DNA curve was run alongside samples. The Taqman qPCR and the commercial qPCR kit detected MAP after PhMS, whereas the SYBR green qPCR assay did not yield any positive results. The difference in detection sensitivity of the commercial MAP f57 qPCR kit compared to the Taqman IS900 qPCR will be due to the lower copy number of f57 target than IS900 target in MAP cells. Further investigation revealed that the OADC component of the 7H9-OADC-2 mM $CaCl_2$ broth used to resuspend the magnetic beads after PhMS, which was still present at DNA template stage, caused inhibition of the SYBR green PCR amplification. These results demonstrate that potential users of the phage-coated beads could combine them with whichever MAP-specific qPCR they are familiar with in their laboratory.

In order to demonstrate that the new PhMS-qPCR was capable of detecting viable MAP in naturally contaminated milk samples, and also to show a potential application of the new PhMS-qPCR test (i.e. milk surveillance), 100 BTM samples kindly provided by a local dairy cooperative were tested. MAP counts indicated by the PhMS-qPCR results were in line with previous reports of levels of viable MAP in BTM samples elsewhere (Foddai et al. 2011; Foddai and Grant 2017; Slana et al. 2008, 2009), although the detection of viable MAP in 49% of these BTM samples from Northern Ireland dairy herds was a little surprising and higher than anticipated. It was not possible to culture the 100 BTM in parallel with PhMS-qPCR due to the low volumes of milk recording samples available to us. Had this been possible, the validity of a PhMS-qPCR positive result as an indication of the presence of viable MAP could have been verified. More extensive PhMS-qPCR testing and culture of BTM and individual milks in comparison with milk-ELISA testing (the test routinely used to screen dairy herds within JD control programmes in several endemically infected countries (Geraghty et al. 2014)) will be reported on in due course.

To conclude, a novel, rapid phage-based PhMS-qPCR test for viable MAP in milk that uses the D29 phage in a different manner to the previous PMS-phage assay was successfully developed and optimised during this study. For naturally infected milk samples, the PhMS-qPCR assay involves PhMS using paramagnetic beads coated with D29 phages, post-PhMS incubation of samples at 37° C. for 4 h (rather than 2 h required for laboratory-grown MAP) followed immediately by a brief heat shock at 55° C. for 1 min, and then MAP-specific IS900 Taqman qPCR. The whole test takes ~7 h, so is potentially a one-day test.

Based on results obtained for BTM, the new PhMS-qPCR assay appears to be a sensitive ($LOD_{50\%}$ 10 MAP/50 ml milk), specific, simpler-to-apply and potentially useful phage-based assay for detecting viable MAP in milk.

REFERENCES

AOAC International (2006) International Presidential Task Force on Best Practices in Microbiological Methodology Final report and executive summaries. Appendix K. Proposed use of a 50% limit of detection value in defining uncertainty limits in the validation of presence-absence microbial detection methods. https://www.fda.gov/downloads/Food/FoodScienceResearch/UCM088764.pdf Last accessed 24 Jul. 2020

Beaver A, Sweeney R W, Hoving E, Wolfgang D R, Gröhn Y T, Schukken Y H (2017) Longitudinal relationship between fecal culture, fecal quantitative PCR and milk ELISA in *Mycobacterium avium* ssp *paratuberculosis*-infected cows from low-prevalence dairy herds. J Dairy Sci 100, 7507-7521. https://doi.org/10.3168/jds.2017-12928.

Bower K, Begg D J, Whittington R J (2010) Optimization of culture of *Mycobacterium avium* subspecies *paratuberculosis* from blood samples. J Microbiol Methods 80, 93-99. https://doi.org/10.1016/j.mimet.2009.11.005.

Bull T J, Vrettou C, Linedale R, McGuinnes C, Strain S, McNair J, Gilbert S C, Hope J C (2014) Immunity, safety and protection of an Adenovirus 5 prime—Modified Vaccinia virus Ankara boost subunit vaccine against *Mycobacterium avium* subspecies *paratuberculosis* infection in calves. Vet Res 45:112. https://doi.org/10.1186/s13567-014-0112-9.

Butot S, Ricchi M, Sevilla I A, Michot L, Molina E, Tello M, Russo S, Arrigoni N, Garrido J M, Tomas D (2019) Estimation of the performance characteristics of analytical methods for *Mycobacterium avium* subsp. *paratuberculosis* detection in dairy products. Front Microbiol 10, 509. https://doi.org/10.3389/fmicb.2019.00509.

Christopher-Henning J, Dammen M A, Weeks S R, Epperson W B, Singh S N, Steinlicht G L, Fang Y, Skaare J L, Larsen J I, Payeur J B, Nelson E A (2003) Comparison of two DNA extractions and nested PCR, real-time PCR, a new commercial PCR assay, and bacterial culture for detection of *Mycobacterium avium* subsp. *paratuberculosis* in bovine feces. J Vet Diagn Invest 15, 87-93. https://doi.org/10.1177/104063870301500201.

Collins M T, Gardner I A, Garry F B, Roussel A J, Wells S J (2006) Consensus recommendations on diagnostic testing for the detection of *paratuberculosis* in cattle in the United States. J Am Vet Med Assoc 229, 1912-1919. https://doi.org/10.2460/javma.229.12.1912.

European Food Safety Authority (2017) Assessment of listing and categorisation of animal diseases within the framework of the Animal Health Law (Regulation (EU) No 2016/429): *Paratuberculosis*. Scientific Opinion adopted 30 Jun. 2017. EFSA J 15(7):4960. https://doi.orq/10.2903/i.efsa.2017.4960.

Foddai A, Elliott C T, Grant I R (2009) Optimization of a phage amplification assay to permit accurate enumeration of viable *Mycobacterium avium* subsp. *paratuberculosis* cells. Appl Environ Microbiol 75, 3896-3902. https://doi.org/10.1128/AEM.00294-09.

Foddai A, Elliott C T, Grant I R (2010a) Rapid assessment of the viability of *Mycobacterium avium* subsp. *paratuberculosis* cells after heating using an optimized phage amplification assay. Appl Environ Microbiol 76(6), 1777-1782. https://doi.org/10.1128/AEM.02625-09

Foddai A, Elliott C T, Grant I R (2010b) Maximizing capture efficiency and specificity of magnetic separation for *Mycobacterium avium* subsp. *paratuberculosis* cells. Appl Environ Microbiol 76, 7550-7558. https://doi.org/10.1128/AEM.01432-10.

Foddai A, Strain S, Whitlock R H, Grant I R. (2011) Application of a novel peptide-mediated phage assay for the detection of viable *Mycobacterium avium* subsp. *paratuberculosis* to bovine bulk tank milk and feces samples. J Clin Microbiol 49, 2017-2019. https://doi.org/10.1128/JCM.00429-11.

Foddai A C G, Grant I R (2015) An optimised milk testing protocol to ensure accurate enumeration of viable *Mycobacterium avium* subsp. *paratuberculosis* by the PMS-phage assay. Int Dairy J 51, 16-23. https://doi.org/10.1016/j.idairyj.2015.07.004

Foddai A C G, Grant I R (2017) Sensitive and specific detection of *Mycobacterium avium* subsp. *paratuberculosis* in raw milk by the peptide-mediated magnetic separation (PMS)-phage assay. J Appl Microbiol 122,1357-1367. https://doi.org/10.1111/jam.13425

Foddai A C G, Grant I R (2020) Methods for detection of viable foodborne pathogens: current state-of-art and future prospects Appl Microbiol Biotechnol 104, 4281-4288—accepted but not yet published Gilardoni L R, Paolicchi F A, Mundo S L (2012) Bovine *paratuberculosis*: a review of the advantages and disadvantages of different diagnostic tests. Rev Argent Microbiol 44, 201-15.

Geraghty, T., Graham, D. A., Mullowney, P., More, S. J. (2014) A review of bovine Johne's disease control activities in 6 endemically infected countries. Prev Vet Med 116, 1-11. https://doi.org/10.1016/j.prevetmed.2014.06.003

Grant I, Ball H, Rowe M (2002) Incidence of *Mycobacterium avium* subsp. *paratuberculosis* in bulk raw and commercial pasteurized cow's milk from approved dairy processing establishments in the United Kingdom. Appl Env Microbiol 68, 2428-2435. https://doi.org/10.1128/AEM.68.5.2428-2435.2002.

Grant I R, Foddai A C G, Tarrant J C, Kunkel B, Hartmann F A, Mc Guirk S, Hansen C, Talaat A M, Collins M T (2017) Viable *Mycobacterium avium* ssp. *paratuberculosis* isolated from calf milk replacer. J Dairy Sci 100, 9723-9735. https://doi.org/10.3168/jds.2017-13154

Laube T, Cortés P, Llagostera M, Alegret S, Pividori M I (2014) Phagomagnetic immunoassay for the rapid detection of *Salmonella*. Appl Microbiol Biotech 98(4), 1795-1805. https://doi.org/10.1007/s00253-013-5434-4

Millar D, Ford J, Sanderson S, Whitey S, Tizard M, Doran T, Hermon-Taylor J (1996) IS900 PCR to detect *Mycobacterium paratuberculosis* in retail supplies of whole pasteurized cows' milk in England and Wales. Appl Environ Microbiol 62, 3446-3452.

O'Brien L M, McAloon C G, Stewart L D, Strain S A J, Grant I R (2018) Diagnostic potential of the peptide-mediated magnetic separation (PMS)-phage assay and PMS-culture to detect *Mycobacterium avium* subsp. *paratuberculosis* in bovine milk samples. Transbound Emerg Dis 65, 719-726. https://doi.org/10.1111/tbed.12794

O'Brien L, Strain S A, Grant I R (2016) Novel monoclonal antibody and peptide binders for *Mycobacterium avium* subsp. *paratuberculosis* and their application for immunomagnetic separation. PLoS ONE 11(1), e0147870. https://doi.org/10.1371/journal.pone.0147870

Pozzato N, Gwozdz J, Gastaldelli M, Capello K, Dal Ben C, Stefani E (2011) Evaluation of a rapid and inexpensive liquid culture system for the detection of *Mycobacterium avium* subsp. *paratuberculosis* in bovine faeces. J Microbiol Meth 84, 413-417. https://doi.org/10.1016/j.mimet.2011.01.019

Radomsky N, Kreitmann L, McIntosh F, Behr M A (2013) The critical role of DNA extraction for detection of mycobacteria in tissues. PLoS One 8, e78749. https://doi.org/10.1371/journal.pone.0078749.

RybnikerJ, Kramme S, Small P L (2006) Host range of 14 mycobacteriophages in *Mycobacterium ulcerans* and seven other mycobacteria including *Mycobacterium tuberculosis*—application for identification and susceptibility testing. J Med Microbiol 55, 37-42. https://doi.org/10.1099/imm.0.46238-0.

Schmelcher M, Loessner M J (2014) Application of bacteriophages for detection of foodborne pathogens. Bacteriophage 4(2):e28137. https://doi.org/10.4161/bact.28137

Sidoti F, Banche G, Astegiano S, Allizond V, Cuffini A M, Bergallo M (2011) Validation and standardization of IS900 and F57 real-time quantitative PCR assays for the specific detection and quantification of *Mycobacterium*

*avium* subsp. *paratuberculosis*. Can J Microbiol 57, 347-354. https://doi.org/10.1139/w11-022.

Slana I, Kralik P, Kralova A, Pavlik I (2008) On farm spread of *Mycobacterium avium* subsp. *paratuberculosis* in raw milk studied by IS900 and F57 competitive real time quantitative PCR and culture examination. Int J Food Microbiol 128, 250-257. https://doi.org/10.1016/j.ijfood-micro.2008.08.013.

Slana I, Liapi M, Moravkova M, Kralova A, Pavlik I (2009) *Mycobacterium avium* subsp. *paratuberculosis* in cow bulk tank milk in Cyprus detected by culture and quantitative IS900 and F57 real-time PCR. Prev Vet Med 89, 223-226. https://doi.org/10.1016/j.prevetmed.2009.02.020.

Stanley E C, Mole R J, Smith R J, Glenn S M, Barer M R, McGowan M, Rees C E D (2007) Development of a new, combined rapid method using phage and PCR for detection and identification of viable *Mycobacterium paratuberculosis* bacteria within 48 Hours. Appl Environ Microbiol 73, 1851-1857. https://doi.org/10.1128/AEM.01722-06.

Stewart L D, McNair J, McCallan L, Thompson S, Kulakov L, Grant I R (2012) Production and evaluation of antibodies and phage display-derived peptide ligands for immunomagnetic separation of *Mycobacterium bovis*. J Clin Microbiol 50, 1598-1605. https://doi.org/10.1128/JCM.05747-11

Stratmann J B, Strommenger K, Stevenson K, Gerlach G F (2002) Development of a peptide-mediated capture PCR for detection of *Mycobacterium avium* subsp. *paratuberculosis* in milk. J Clin Microbiol 40, 4244-4250. https://doi.org/10.1128/JCM.40.11.4244-4250.2002.

Stratmann J, Dohmann K, Heinzmann J, Gerlach G F (2006) Peptide aMptD-mediated capture PCR for detection of *Mycobacterium avium* subsp. *paratuberculosis* in bulk milk samples. Appl Environ Microbiol 72, 5150-5158. https://doi.org/10.1128/AEM.00590-06.

Swift B M C, Meade N, Sandoval Barron E, Bennett M, Perehenic T, Hughes V, Stevenson K, Rees C E D (2019) The development and use of Actiphage® to detect viable mycobacteria from bovine tuberculosis and Johne's disease-infected animals. Microb Biotechnol 13, 738-746. https://doi.org/10.1111/1751-7915.13518.

Van Schaik G, Rossiter C R, Stehman S M, Shin S J, Shukken Y H (2003) *Longitudinal study to investigate variation in results of repeated ELISA and culture samples for Mycobacterium avium subspecies paratuberculosis in commercial dairy herds*. Amer J Vet Res 64, 479-484. https://doi.org/10.2460/agvr.2003.64.479.

Example 3—Performance of New One-Day Phagomagnetic-qPCR Assay of the Present Invention, Relative to Currently Applied 'Gold Standard' Tests for Diagnosing Johne'S Disease/Map Infection in Cattle The kits used for Blood ELISA and faecal qPCR in this Example are:

| Test | Matrix (blood, etc) | Test kit (name and manufacturer) - insert lines if more than two kits used | Type (blocking/indirect ELISA/PCR etc) |
|---|---|---|---|
| MAP AB (ELISA) | Blood | *Mycobacterium paratuberculosis* Antibody Test Kit. (IDEXX) | Indirect Antibody ELISA |
| PCR | Faeces | VetMAX MAP Real-Time PCR screening kit. (Applied Biosystems by Life Technologies) | Real time PCR |

Testing of faeces and milk from 28 dairy cattle confirmed to be MAP infected by the 'gold standard' tests (Faecal qPCR and/or blood-ELISA).

| Cow ID | 'Gold standard' diagnostic tests | | New Phagomagnetic-qPCR assay | |
|---|---|---|---|---|
| | Blood-ELISA | Faecal qPCR | Faeces | Milk |
| 1 | pos | pos | pos | pos |
| 2 | pos | neg | neg | neg |
| 3 | pos | pos | pos | pos |
| 4 | pos | pos | n/a | pos |
| 5 | pos | neg | neg | neg |
| 6 | pos | neg | pos | neg |
| 7 | pos | neg | neg | pos |
| 8 | pos | pos | pos | pos |
| 9 | pos | pos | pos | pos |
| 10 | pos | pos | pos | pos |
| 11 | pos | pos | pos | neg |
| 12 | pos | neg | pos | pos |
| 13 | pos | neg | neg | pos |
| 14 | pos | pos | pos | neg |
| 15 | pos | neg | neg | neg |
| 16 | pos | neg | neg | neg |
| 17 | n/a | pos | pos | neg |
| 18 | pos | neg | pos | neg |
| 19 | pos | neg | pos | pos |
| 20 | pos | neg | pos | pos |
| 21 | pos | neg | pos | neg |

-continued

| | 'Gold standard' diagnostic tests | | New Phagomagnetic-qPCR assay | |
| Cow ID | Blood-ELISA | Faecal qPCR | Faeces | Milk |
| --- | --- | --- | --- | --- |
| 22 | pos | neg | neg | neg |
| 23 | pos | neg | pos | neg |
| 24 | pos | neg | neg | neg |
| 25 | pos | pos | pos | pos |
| 26 | n/a | neg | pos | neg |
| 27 | pos | neg | pos | pos |
| 28 | pos | pos | pos | pos |
| No. of positive test results/total no. of animals tested (%) | 26/26 (100%) | 11/28 (39.2%) | 19/27 (70.4%) | 14/28 (50%) | n/a, sample not available for testing

The new phagomagnetic (PhMS)-qPCR assay of the present invention detected viable MAP in the faeces of 8 (28.6%) more of the 28 MAP-infected cattle than the 'gold standard' faecal qPCR assay, illustrating the new test's greater detection sensitivity. There was only fair agreement between the results of the two faecal tests:

| | Faecal qPCR+ | Faecal qPCR− | Total |
| --- | --- | --- | --- |
| PhMS-qPCR+ | 10 | 9 | 19 |
| PhMS-qPCR− | 0 | 8 | 8 |
| Total | 10 | 17 | 27 |

Number of observed agreements: 18 (66.67% of the observations)
Number of agreements expected by chance: 12.1 (44.72% of the observations)

Kappa=0.397
SE of kappa=0.131
95% confidence interval: From 0.140 to 0.654
The strength of agreement is considered to be 'fair'.

Milk samples collected from 14 (50%) of the 28 MAP-infected cattle also tested positive for viable MAP by the new phagomagnetic-qPCR assay of the present invention; illustrating that the new assay has sufficient sensitivity to detect low numbers of viable MAP in naturally contaminated milk.

Testing of faeces and milk from 60 dairy cattle that tested negative by both currently applied diagnostic tests for Johne's disease.

Faeces and milk from a further cohort of 60 dairy cattle on a single farm that showed no evidence of MAP infection when the 'gold standard' tests were applied were also subjected to the new phagomagnetic-qPCR assay of the present invention.

| | 'Gold standard' JD diagnostic tests | | New Phagomagnetic-qPCR assay | |
| Cow ID | Blood-ELISA | Faecal qPCR | Faeces | Milk |
| --- | --- | --- | --- | --- |
| 1 | Neg | Neg | pos | pos |
| 2 | Neg | Neg | pos | pos |
| 3 | Neg | Neg | pos | pos |
| 4 | Neg | Neg | pos | neg |
| 5 | Neg | Neg | neg | neg |
| 6 | Neg | Neg | pos | neg |
| 7 | Neg | Neg | pos | neg |
| 8 | Neg | Neg | neg | pos |
| 9 | Neg | Neg | neg | neg |
| 10 | Neg | Neg | neg | neg |
| 11 | Neg | Neg | pos | pos |
| 12 | Neg | Neg | pos | pos |
| 13 | Neg | Neg | pos | pos |
| 14 | Neg | Neg | neg | pos |
| 15 | Neg | Neg | neg | neg |
| 16 | Neg | Neg | neg | neg |
| 17 | Neg | Neg | pos | neg |
| 18 | Neg | Neg | neg | neg |
| 19 | Neg | Neg | neg | pos |
| 20 | Neg | Neg | pos | pos |
| 21 | Neg | Neg | neg | neg |
| 22 | Neg | Neg | neg | neg |
| 23 | Neg | Neg | pos | neg |
| 24 | Neg | Neg | neg | neg |
| 25 | Neg | Neg | pos | pos |
| 26 | Neg | Neg | neg | neg |
| 27 | Neg | Neg | neg | neg |
| 28 | Neg | Neg | pos | pos |
| 29 | Neg | Neg | pos | neg |
| 30 | Neg | Neg | neg | pos |
| 31 | Neg | Neg | pos | neg |
| 32 | Neg | Neg | neg | neg |
| 33 | Neg | Neg | neg | neg |

-continued

| | 'Gold standard' JD diagnostic tests | | New Phagomagnetic-qPCR assay | |
| Cow ID | Blood-ELISA | Faecal qPCR | Faeces | Milk |
| --- | --- | --- | --- | --- |
| 34 | Neg | Neg | pos | pos |
| 35 | Neg | Neg | pos | pos |
| 36 | Neg | Neg | neg | neg |
| 37 | n/a | Neg | neg | neg |
| 38 | n/a | Neg | pos | neg |
| 39 | n/a | Neg | pos | pos |
| 40 | n/a | Neg | pos | pos |
| 41 | n/a | Neg | pos | pos |
| 42 | n/a | Neg | pos | neg |
| 43 | n/a | Neg | pos | pos |
| 44 | Neg | Neg | neg | neg |
| 45 | Neg | Neg | pos | pos |
| 46 | n/a | Neg | neg | neg |
| 47 | n/a | Neg | pos | pos |
| 48 | Neg | Neg | neg | neg |
| 49 | Neg | Neg | neg | neg |
| 50 | Neg | Neg | pos | pos |
| 51 | Neg | Neg | neg | neg |
| 52 | n/a | Neg | pos | neg |
| 53 | n/a | Neg | neg | neg |
| 54 | n/a | Neg | neg | neg |
| 55 | n/a | Neg | neg | neg |
| 56 | n/a | Neg | pos | pos |
| 57 | n/a | Neg | neg | neg |
| 58 | Neg | Neg | pos | pos |
| 59 | n/a | Neg | neg | neg |
| 60 | n/a | Neg | neg | neg |
| No. of positive test results/total no. of animals tested (%) | 0/60 (0%) | 0/60 (0%) | 30/60 (50%) | 20/60 (33.3%) | n/a, sample not available for testing

The results from the new phagomagnetic-qPCR assay of the present invention indicated the presence of low levels of viable MAP in the faeces and milk of 50% and 33.3% of 60 'gold standard test' negative cows, respectively. There was moderate agreement between the faeces and milk phago-magnetic-qCPR results from the same cow:

| | Faeces+ | Faeces− | Total |
| --- | --- | --- | --- |
| Milk+ | 17 | 3 | 20 |
| Milk− | 13 | 27 | 40 |
| Total | 30 | 30 | 60 |

Number of observed agreements: 44 (73.33% of the observations)
Number of agreements expected by chance: 30.0 (50.00% of the observations)
Kappa=0.467
SE of kappa=0.108
95% confidence interval: From 0.256 to 0.678
The strength of agreement is considered to be 'moderate'.
These findings suggest that the 'gold standard' tests currently being applied to test cattle for Johne's disease lack detection sensitivity, which means that negative test results are being obtained for cows that are actually MAP infected.

Example 4—Phagomagnetic qPCR: a Rapid, Sensitive and Specific Surveillance Tool for Viable *Mycobacterium AVIUM* Subsp. *Paratuberculosis* in Bulk Tank and Individual Cows' Milk Bulk tank milk (BTM) and individual cow's milk were tested by a new phage-based assay (phagomagnetic-qPCR)

for detection of viable *Mycobacterium avium* subsp. *para-tuberculosis* (MAP) in parallel with milk-ELISA to test for presence of MAP antibodies. There was no significant correlation between results of the two tests. PhMS-qPCR proved to be a much more sensitive test for detecting MAP infected dairy herds via BTM testing, and for identifying MAP infected and shedding animals within four of these herds. We have demonstrated that the new PhMS-qPCR assay would be useful for Johne's disease surveillance or milk quality assurance programs.

Bulk tank milk samples from 392 Northern Ireland dairy farms, and individual milk from animals (n=293) on four of these farms, were tested by a novel phagomagnetic separa-tion (PhMS)-qPCR assay able to detect and quantify viable *Mycobacterium avium* subsp. *paratuberculosis* (MAP), in order to demonstrate its potential utility as a milk surveil-lance tool. Viable MAP were detected in 26.5% of the bulk tank milks, with MAP contamination levels ranging from 1-8432 MAP/50 ml milk; <2% of farms had MAP contami-nation levels >100 MAP/50 ml in their bulk tank milk. Follow up PhMS-qPCR testing of milk from individual animals on four farms that had the highest numbers of MAP in their bulk tank milks indicated the existence of 17-24% of animals in each herd shedding viable MAP in their milk. Mean MAP numbers detected ranged between 6.7 and 42.1 MAP/50 ml milk. No significant correlation was observed between detection of viable MAP in bulk or individual milks by PhMS-qPCR and parallel milk-ELISA result, or indeed between PhMS-qPCR results and any other milk recording parameter (somatic cell count, total bacterial count (Bac-toscan), butterfat % or protein %). A second 50 ml aliquot of 61 PhMS-qPCR positive individual milk samples from the four farms was cultured in MH7+ (Pozzato) broth following peptide-mediated magnetic separation. Fifty-two (85.2%)

broth cultures showed evidence of MAP by IS900 qPCR after incubation, thereby confirming that a PhMS-qPCR positive result was generally a true indication of the presence of viable MAP in the milk sample. Our findings clearly demonstrate that the novel PhMS-qPCR assay could be a useful milk surveillance tool for dairy processors, or a milk monitoring tool for Johne's disease control or milk quality assurance programs.

Milk is one of three specimen types collected for Johne's disease diagnosis purposes, the other two being feces and blood. Milk represents a more convenient sample type to collect, since the presence of a vet is not required, and it can be sampled from the bulk tank for herd-level screening purposes or from individual animals on a dairy farm. Animals infected with *Mycobacterium avium* subsp. *paratuberculosis* (MAP), the causative agent of Johne's disease, shed the bacterium in their feces and milk even when they are not showing any clinical signs of Johne's disease (Barkema et al. 2010). Direct shedding of MAP within the udder of infected animals may be augmented by indirect contamination during the milking process with MAP from feces, which generally contains much higher numbers of MAP than milk (Okura et al. 2013). The presence of MAP in milk or colostrum of infected dams represents a Johne's disease transmission risk for calves, which is why not feeding calves with MAP-infected milk is one of the main recommendations within Johne's disease control programmes (Whittington et al. 2019). MAP contaminated milk may also represent a vehicle for human exposure to MAP since cows' milk is widely consumed by humans from a young age. Debate continues about whether or not pasteurisation of milk effectively kills MAP (Lund et al. 2002; Robertson et al. 2017) and whether MAP is the cause of or a contributory factor for Crohn's disease in humans (Chiodini et al. 2012; Waddell et al. 2015). There are several reasons why governments, animal health organisations, farmers or milk processors may wish to test milk for evidence of MAP contamination. Firstly, to monitor levels of MAP in bulk tank milk over time in herds within Johne's disease control programmes (McAloon et al. 2019) or milk quality assurance programmes (Weber et al. 2008). Secondly, to assure consumer safety in relation to consumption of raw (Giacometti et al. 2012) or commercially pasteurised (Gerrard et al. 2018) milk. Thirdly, to be able to demonstrate freedom from infection in MAP test-negative herds (Meyer et al. 2019), or to certify milk from dairy herds as MAP-free (Köhler et al. 2017). In a recent study, Gamberale et al. (2019) wanted to be able to ascertain the MAP status of colostrum in order to establish a safe colostrum bank.

Currently, the only Johne's diagnostic test widely applied to test milk is the milk-ELISA, which detects antibodies to MAP rather than the pathogen itself (Office International des Epizooties 2019). This test is considered to be a non-invasive, practical and cost-effective approach for surveillance for MAP infection in dairy cattle (Pesquiera et al. 2017; Köhler et al. 2017), but it has certain limitations. The milk-ELISA when applied to bulk tank milk only permits identification of herds with very high herd prevalence of MAP shedders (Köhler et al. 2017; Sergeant et al. 2019), and when applied to test milk from individual animals is unreliable in MAP negative and low prevalence herds (Lavers et al. 2014). Kostoulas et al. (2013) reported that the ability of the milk ELISA to discriminate between healthy and MAP infected cattle was extremely poor, but high between healthy and MAP-infectious cattle. The sensitivities of commercial milk ELISAs applied to cows' milk are in the range 21-61%, and the specificities of milk ELISA are in the range 83-100%

(Nielsen and Toft, 2008). Milk-ELISA is considered less sensitive than blood-ELISA for individual animal testing (Khol et al. 2013). Culture of milk for diagnostic purposes is not often undertaken, despite the fact that this is considered the only method capable of confirming the viability of MAP. This is principally because of the length of time it takes for results to become available and the distinct possibility that the low levels of viable MAP present might not be detected because of the detrimental effects of chemical decontamination, which usually forms part of the milk culture procedure, on MAP viability (Dundee et al. 2001; Bradner et al. 2013). A rapid diagnostic test able to detect and quantify viable MAP in milk, as an alternative to slow culture, would be an attractive proposition for Johne's disease surveillance. Above, we reported the development and optimisation of a novel phage-based test for viable MAP, called phagomagnetic (PhMS)-qPCR. This PhMS-qPCR assay is a much simplified and streamlined version of our previous peptide-mediated magnetic separation (PMS)-phage assay for detection of viable MAP in milk (Foddai et al. 2011; Foddai and Grant 2015, 2017). D29 mycobacteriophage-coated paramagnetic beads are used for magnetic separation of MAP from the milk sample, rather than MAP-specific biotinylated peptides. In our hands, the PMS-phage assay has proven to be a very sensitive and specific test for viable MAP in milk. Unfortunately, due to its requirement for two overnight incubations, multiple timed steps and additions of reagents, and the need to harvest plaques for PCR confirmation of a positive result (Foddai and Grant 2017), transfer of the PMS-phage assay to other laboratories has proven to be problematic for a variety of reasons (Butot et al. 2018). The new PhMS-qPCR assay differs from the PMS-phage assay in a number of key respects (detailed in unpublished Foddai and Grant 2020; and reported in Example 2 above). The main differences are: molten agar and an *M. smegmatis* culture are no longer required, the new test yields results in ~7 h rather than 48 h, and confirmation of MAP presence is by MAP-specific, and faster, Taqman qPCR applied directly to the sample and not by conventional IS900 PCR applied to DNA that has to be extracted from plaques. We believe that the PhMS-qPCR assay may represent the long awaited alternative test to MAP culture.

The objective of this study was to demonstrate the potential utility of the novel phage-based PhMS-qPCR assay as a surveillance tool to detect viable MAP contamination in bulk tank milk at herd level or in the milk of individual animals within MAP-infected dairy herds. PhMS-qPCR testing was carried out contemporaneously with milk-ELISA and other milk recording tests so that any agreement or correlation between test results could be determined.

Materials and Methods

Description of PhMS-qPCR Assay

Full details of the development and optimisation of the new PhMS-qPCR assay were reported in unpublished Foddai and Grant (2020) and set out in Example 2 above. The assay employs D29 mycobacteriophages coated onto BcMag tosylactivated paramagnetic beads (Bioclone Inc., San Diego, USA) to both capture and then subsequently lyse any viable MAP cells in a milk sample, to provide MAP DNA for IS900 Taqman qPCR. Briefly, milk samples were pre-warmed in a water bath at 37° C. for 15 min prior to centrifugation at 2500×g for 15 min to obtain the milk pellet. This was thoroughly resuspended in 1 ml phosphate buffered saline containing 0.05% Tween 20 (PBS-T20, Sigma-Aldrich, Poole, UK) before addition of 15 μl D29 phage-coated BcMag beads (prepared as described in Example 2 above and in unpublished Foddai and Grant, 2020) to each sample. Automated magnetic separation proceeded in a Dynal BeadRetriever (Life Technologies, Paisley, UK) using the built-in 'Environmental' programme which consists of mixing of the sample plus phage-coated beads for 30 min, two washes of bead-MAP cell complexes in 1 ml PBS-T20 for 1 min, and then final elution of bead-MAP cell complexes in 50 µl Middlebrook 7H9 broth containing 10% OADC (both Difco) and 2 mM $CaCl_2$(Sigma-Aldrich). Fifteen milk samples were processed in each BeadRetriever run. When PhMS was complete, the beads were quickly transferred to 1.5 ml Eppendorf tubes and incubated at 37° C. for 4 h; at which point the tubes were transferred to a Stuart block heater (Cole-Parmer, Stone, UK) operating at 55° C. for 1 min, before being centrifuged at 10,000×g for 2 min. Sample supernatant (8 µl per reaction) was used as template DNA for IS900 Taqman qPCR, carried out immediately or the following day after storage of DNA samples at −80° C. Duplicate qPCR reactions per sample were performed. The qPCR was carried out on an Eco-qPCR system (Illumina Inc., San Diego, USA) with primers/probe sequences originally reported by Sidoti et al. (2011) and using SensiFAST™ Probe® Hi-ROX mastermix (Bioline Reagents Limited, London, UK). Different from the original Sidoti et al. (2011) protocol, the qPCR reaction setup included increased primer concentrations and twice the amount of template DNA; which we found to improve detection sensitivity. PCR cycling conditions consisted of an initial warm up section of 50° C. for 2 min, a denaturation step at 95° C. for 10 min followed by 40 cycles of 95° C. for 15 s and 60° C. for 1 min. A Real-time PCR threshold cycle (Ct) cut-off of 38 cycles was consistently applied to all the samples to improve interpretation of qPCR outcomes. Results were considered positive if the Ct values were A standard curve determination was included in each qPCR run, comprised of duplicate samples of DNA equivalent to $10^4$, $10^3$, $10^2$ and 10 MAP cells/ml, which permitted quantitation of the detected MAP cells in the milk samples. Duplicate (rather than triplicate) aliquots of each sample and control DNA were subjected to qPCR due to the limited 48 well capacity of the Eco-qPCR plates (Illumina Inc.).

Bulk Tank Milk Testing

A single bulk tank milk (BTM) sample from 392 Northern Ireland dairy farms supplying Dale Farm Limited was tested by the new PhMS-qPCR assay between October 2019 and January 2020. These samples were residual BTM samples from the Dale Farm laboratory testing stream and so milk sample volume was rather inconsistent; varying between 15 and 40 ml. These 392 herds represent ~30% of the total ~1280 dairy herds supplying Dale Farm with milk for processing. All BTM samples were to have been tested by a commercially available MAP milk-ELISA at an external laboratory (Cattle Information Services (CIS), Telford, UK), but due to one batch of samples not being sent in error, only 340 of the 392 bulk tank milk samples were tested by milk-ELISA. PhMS-qPCR and milk-ELISA results were collated along with other available milk quality results (Somatic Cell Count, Total Bacterial Count (Bactoscan), Butterfat %, Protein %) provided by Gary Watson, Dale Farm. Due to the variable milk volume tested, the PhMS-qPCR qPCR result (estimated MAP count/volume tested) was corrected to per 50 ml to permit comparison of MAP load between BTM samples.

Individual Milk Testing

Milk samples (100 ml) for MAP testing purposes were collected during February and March 2020 from 294 individual cows on four dairy herds (Farms A-D). These herds were selected from amongst the 392 farms whose BTM had been tested because they had the highest MAP loads. The individual milk samples were sampled from collection jars in the milking parlour (rather than by hand-milking) at the same time as samples were being collected for routine milk recording purposes. Upon arrival at the Queen's University Belfast laboratory, each 100 ml sample was aseptically split into two sterile 50 ml centrifuge tubes. One 50 ml sample was tested by the PhMS-qPCR test and the other was frozen at −80° C. until the PhMS-qPCR result was known. Dale Farm sent the milk recording samples from the same animals, collected at the same time, to CIS Telford for MAP milk-ELISA testing, and their in-house laboratory carried out the other milk recording analyses. PhMS-qPCR and milk-ELISA results were collated along with other available milk recording results (lactation number, milk weight kg, butterfat %, protein %, somatic cell count) for these animals provided by Gary Watson, Dale Farm.

PMS followed by culture, as described by Foddai and Grant (2017), was performed on the second 50 ml aliquot of any milk samples that had tested PhMS-qPCR positive. The MH7+ broth described by Pozzato et al. (2011) without the addition of egg yolk (hereinafter referred to as Pozzato broth) and supplemented with PANTA antibiotics (Becton Dickinson) was employed. Cultures were incubated at 37° C. for several months, and visually examined periodically for signs of growth from 4 weeks of incubation onwards. Once an increase in turbidity was observed, a 1 ml aliquot of the culture was carefully removed, centrifuged and resuspended in 100 µl Tris-EDTA pH 8.0, which was heated at 99° C. for 30 min in a heating block to lyse MAP cells to release DNA. Five µl of the supernatant was then subjected to IS900 Taqman qPCR (see optimized qPCR protocol described above) in order to confirm the presence of MAP biomass in the culture.

Statistical Analysis of Results

Correlations between PhMS-qPCR and all other available milk testing results were assessed by Pearson r correlation test performed using GraphPad Prism version 8.4.3 (GraphPad Software, San Diego, USA). Contingency tables (2×2) were constructed and Kappa agreement between PhMS-qPCR and milk-ELISA results was determined using EpiTools Epidemiological Calculators (http://epitools.au-svet.com.au). P values <0.05 were considered statistically significant.

Results and Discussion

The primary purpose of the milk testing reported here was to assess the utility of the new PhMS-qPCR assay as a milk surveillance tool and to compare its performance with the assay commonly applied to test milk for evidence of MAP infection in many countries, the milk-ELISA (Geraghty et al. 2014; Meyer et al. 2019). The PhMS-qPCR assay is a much simpler and easy-to-apply version of the PMS-phage assay, previously optimised for testing milk by Foddai and Grant (2015), and hence it could potentially be suitable for larger scale milk testing as a rapid alternative to culture of MAP.

To our knowledge, the BTM testing reported here represents the first reasonably sized survey for MAP in cows' milk produced by N. Ireland dairy herds. Viable MAP was detected in 104 (26.5%) of the 392 BTM from different N. Ireland dairy farms tested by the new PhMS-qPCR assay, with numbers of viable MAP detected ranging from 1-8432 MAP/50 ml BTM. No previous survey for Johne's disease in N. Ireland dairy herds has been carried out, however it is likely that the proportion of infected herds in N. Ireland is within the range 20% (United Kingdom data, Animal Health and Welfare Northern Ireland, 2014) to 35% (Republic of Ireland data, McAloon et al., 2016). Thus, the figure of 26.5% for MAP infection prevalence in the N. Ireland dairy herds supplying a local dairy cooperative falls within the anticipated range. FIG. 18 shows the distribution of MAP contamination levels detected in 50 ml samples of BTM. The majority of BTM samples (286/392, 73.15%) tested negative for viable MAP by the PhMS-qPCR assay, and only 2 (0.5%) and 5 (1.28%) bulk tank milk samples had MAP contamination levels in the highest 1,001-10,000 MAP/50 ml and 101-1,000 MAP/50 ml categories. These PhMS-qPCR-derived MAP counts are consistent with those reported for BTM tested by earlier versions of the phage assay (2-320 PFU/50 ml by Phage-PCR assay, Botsaris et al. 2013; 18-685 PFU/50 ml by PMS-phage assay, Foddai and Grant 2017) and by f57 qPCR (<15-32.4 cells/ml, Ricchi et al. 2016). They are also consistent with figures predicted by Okura et al. (2013) for BTM from Danish dairy herds with within-herd MAP infection prevalence from 7.5-60.0%. In the case of BTM, the restricted volumes of residual milk available for testing meant that culture could not be carried out on PhMS-qPCR positive samples in order to confirm that viable MAP were indeed present. However, later on in our study, PhMS-qPCR positive individual milk samples were cultured and 85.2% of the liquid cultures yielded IS900 qPCR positive biomass; so, in the light of this, we believe a PhMS-qPCR positive result is indicative of milk contaminated with viable MAP.

In contrast to the 26.5% of BTM positive by the PhMS-qPCR assay, only 21 (7.2%) of 340 (one batch of 50 BTM was not tested and one milk sample was sour and could not be tested) BTM samples tested 'positive' (nine with S/P ratio >0.3) or 'doubtful' (twelve with S/P ratio 0.2-0.3) by the MAP milk-ELISA. Only three milk-ELISA 'positive' samples also tested PhMS-qPCR positive (Table A).

TABLE A

2 × 2 contingency table of PhMS-qPCR and milk-ELISA results for 340 bulk tank milk samples.

| | Milk-ELISA +ve | Milk-ELISA −ve | Total |
|---|---|---|---|
| PhMS-qPCR +ve | 3 | 101 | 104 |
| PhMS-qPCR −ve | 6 | 230 | 236 |
| Total | 9 | 331 | 340 |

Kappa = 0.0046 'No agreement',
95% CI: −0.0463-0.0555,
P(kappa) = 0.4281

No significant correlation, positive or negative, was found to exist between the PhMS-qPCR and milk-ELISA results ($r^2$=−0.02, p=0.520) for BTM samples. This is probably not surprising since the two tests detect different things; shedding of MAP antigen in the case of PhMS-qPCR and presence of MAP antibody in the case of milk-ELISA. Kappa value (0.0046, 95% CI: −0.0463-0.0555, P(kappa) 0.4281) indicated 'no agreement' between PhMS-qPCR and 'positive' milk-ELISA results for BTM (Table A). The milk-ELISA has been used to test BTM for MAP surveillance purposes previously in some countries (Nielsen and Toft, 2014; van Weering et al., 2007). However, it is generally acknowledged that the milk-ELISA test is likely to be a more reliable indicator of MAP infection status when applied to milk from individual animals within dairy herds rather than BTM (van Weering et al. 2007), and when applied to test milk from older animals (Kostoulas et al. 2013; Wilson et al. 2010). The presence of viable MAP detected by the PhMS-qPCR assay in BTM was also not significantly correlated with any of the other milk recording results (somatic cell count, total bacterial count (Bactoscan), % Butterfat or % Protein), illustrated by the correlation matrix in FIG. 19.

Individual Milk Testing

The four dairy herds (Farms A-D) selected for follow-up testing of milk from individual animals were amongst the seven N. Ireland herds with the highest MAP load indicated for their BTM in the earlier part of the study. The purpose of this individual milk testing was twofold. Firstly, to identify which animals within the suspected MAP infected herds were shedding the bacterium in their milk and in what numbers, and secondly to determine if there may be a better correlation between results of the new PhMS-qPCR assay and milk-ELISA when applied at individual cow-level. Individual milks tested were collected from milk recording jars in the milking parlour for convenience and speed, as individual milks normally would be for milk recording purposes, rather than being collected after meticulous udder cleaning by hand. We, therefore, cannot exclude the possibility of carryover of MAP contamination between the milks of different cows.

TABLE B

Summary of PhMS-qPCR, milk-ELISA and other milk recording results for 294 individual milk samples collected from cows on four Northern Ireland dairy farms that had the highest MAP loads in their bulk tank milk during the initial survey.

| Parameter | Farm A | Farm B | Farm C | Farm D |
|---|---|---|---|---|
| No. of milking cows sampled | 62 | 42 | 123 | 67 |
| *PhMS-qPCR results:* | | | | |
| No. (%) cows with PhMS-qPCR positive milk sample | 12 (17.7) | 10 (23.8) | 29 (23.6) | 12 (17.9) |
| Mean no. (±SD) viable MAP/50 ml detected by PhMS-qPCR | 6.7 ± 5.2 | 42.1 ± 37.2 | 14.0 ± 12.47 | 22.2 ± 36.67 |
| *Milk-ELISA results:* | | | | |
| *No. (%) milk samples with S/P ratio:* | | | | |
| >0.30 (positive) | 7 (11.3) | 11 (26.2) | 9 (7.5) | 0* (0) |
| 0.20-0.30 (doubtful) | 3 (4.8) | 2 (4.8) | 7 (5.8) | 1 (1.5) |
| <0.20 (negative) | 52 (83.9) | 29 (69.0) | 104 (86.7) | 64 (98.5) |
| *Milk recording data (mean ± SD):* | | | | |
| Lactation no. | 3.47 ± 2.29 | 2.86 ± 1.60 | 2.91 ± 2.05 | 2.72 ± 1.95 |
| Milk weight (kg) per cow | 25.56 ± 7.97 | 29.83 ± 8.22 | 30.68 ± 7.16 | 18.81 ± 7.15 |
| Somatic cell count ('000) | 125.0 ± 174.2 | 132.1 ± 429.0 | 200.9 ± 453.1 | 94.39 ± 138.1 |

TABLE B-continued

Summary of PhMS-qPCR, milk-ELISA and other milk recording results for 294 individual
milk samples collected from cows on four Northern Ireland dairy farms that had
the highest MAP loads in their bulk tank milk during the initial survey.

| Parameter | Farm A | Farm B | Farm C | Farm D |
|---|---|---|---|---|
| Butterfat (%) | 5.30 ± 0.79 | 4.28 ± 0.58 | 4.53 ± 0.66 | 5.43 ± 1.41 |
| Protein (%) | 3.44 ± 0.41 | 3.41 ± 0.36 | 3.50 ± 0.27 | 3.49 ± 0.38 |

*For Farm D only, Milk-ELISA was carried out on previously frozen and thawed milk samples because of a misunderstanding between Dale Farm and the testing laboratory.

Table B, above, summarises the results of testing of individual milks from 294 animals on Farms A-D. PhMS-qPCR results confirmed the existence of individual animals shedding MAP in their milk on all four of the farms. On Farms A and D, ~17% of cows were shedding MAP into their milk, and on Farms B and C ~24%. Milk-ELISA results indicated the existence of MAP positive animals on three of the four farms (all except Farm D); Farm B had the highest number of cows testing milk-ELISA positive (11/42, 26.2%) and Farm D had no positive results and only one 'doubtful' result. However, in the case of Farm D only, the milk-ELISA test had to be carried out on previously frozen milk samples, due to a misunderstanding between Dale Farm and the testing laboratory. Consequently, we cannot rule out the possibility that frozen storage may have had a negative impact on milk-ELISA results, as has been reported previously for serum-ELISA results (Alinovi et al. 2009). The mean number of viable MAP being shed by PhMS-qPCR positive animals ranged from 6.7 MAP/50 ml milk for Farm A to 42.1 MAP/50 ml milk for Farm B. Once again, these MAP counts are consistent with numbers reported for milk from individual animals in the UK and N. Ireland contexts when tested using the optimised PMS-phage assay (6-948 PFU/50 ml, Foddai and Grant 2017; 8-94 PFU/50 ml, O'Brien et al. 2018).

and milk-ELISA results also varied by farm, with Farm A results showing 'fair agreement', Farm C results showing 'slight agreement', and Farm B results showing 'no agreement' (Table C). Kappa agreement for Farm D results could not be calculated due to the issue of ELISA testing of frozen and thawed milks potentially impacting milk-ELISA results, as mentioned earlier. Similar to the BTM findings, there were no significant correlations between the presence of viable MAP detected by PhMS-qPCR and any of the milk recording parameters (lactation number, weight of milk (kg), % butterfat, % protein or somatic cell count), as illustrated by the correlation matrices for the four farms in FIG. 20.

In the case of the individual milks, PMS-culture was carried out on a second 50 ml aliquot of each PhMS-qPCR positive milk sample (collected at the same time but stored frozen at −20° C. until required), in order to confirm the presence of viable MAP in these samples and hence verify that a PhMS-qPCR positive was not a false positive result. Of 61 PhMS-qPCR positive milk samples cultured in Pozzato broth, 52 (85.2%) cultures yielded a pellet at the end of a 12-week incubation period that tested IS900 Taqman qPCR positive, indicating the presence of viable MAP. Only liquid culture was applied, and pure MAP colonies have yet to be isolated. This high percentage of IS900 qPCR positive cultures strongly suggests that a positive PhMS-qPCR result

TABLE C

Agreement between PhMS-qPCR and milk-ELISA results
for milk from individual animals on Farms A-D.

| | Test result combination, n (%[a]) | | | | | |
|---|---|---|---|---|---|---|
| | Milk-ELISA | | | | | |
| | + | + | − | − | | |
| | | PhMS-qPCR | | | Kappa | |
| | + | − | + | − | (95% CI) | P(kappa) |
| Farm A | 4 (6.5) | 3 (4.8) | 8 (12.9) | 47 (75.8) | 0.3248 0.0226-0.6269 | 0.0036** |
| Farm B | 2 (4.8) | 9 (21.4) | 7 (16.7) | 23 (54.8) | −0.0547 (−0.3445-−0.2352) | 0.3620[NS] |
| Farm C | 3 (2.4) | 6 (4.9) | 25 (20.3) | 86 (69.9) | 0.0549 (−0.1801-0.2179) | 0.2304[NS] |
| Farm D | 0 | 0 | 12 (17.9) | 53 (79.1) | —[b] | — |

[a]calculated as % of total number of animals tested in herd, rather than % of animals for which both test results were available;
[b]not calculable because no milk-ELISA positive animals detected Statistical analysis (see Table C above) indicated that for individual milks, as for BTM, there were no significant correlations, positive or negative, between PhMS-qPCR and milk-ELISA results on any of the four farms ($r^2$=0.22 (p=0.080), −0.17 (p=0.284), 0.02 (p=0.817) and 0.13 (p=0.300) for Farms A, B, C and D, respectively). With the exception of Farm C, the $r^2$ values were higher than for BTM and the correlation p value approached statistical significance for Farm A. Kappa agreement between PhMS-qPCR is a real indication of the presence of viable MAP in a milk sample, and not a false positive result.

In terms of how the new PhMS-qPCR test might be applied as a screening test for viable MAP in milk, this could easily be added to the existing range of tests applied to either bulk tank milk or milks from individual animals for milk recording purposes by milk processors. A remaining difficulty is the limitation of the Beadretriever instrument only being able to process 15 samples at a time, meaning that multiple runs are needed to process a reasonable number of milk samples (probably maximum of three runs, 45 samples), in order to complete the assay within a working day. Larger capacity magnetic separation instruments do exist (e.g. Kingfisher Flex from Thermofisher Scientific and BioSprint 96 from Qiagen) that are capable of processing up to 96×1 ml samples in a single run. However, these have primarily been designed for DNA extraction and not bacterial cell separation purposes. It may be possible to customize software protocols to make these instruments suitable for MAP cell separation and concentration. Of course, PhMS could be performed manually with samples in 1.5 ml Eppendorf tubes, a rotator mixer and a suitable magnetic rack; which would facilitate the processing of as many samples as wished in a working day. However, the limitations of manual PhMS would be its laborious nature, increased amount of plastic consumables required, and the probability that more than one wash of the captured bead-cell complexes would not be feasible. It also needs to be remembered that, after PhMS, an incubation period of 4 h for naturally contaminated milk samples is required before DNA can be harvested (before storage at –80° C. overnight prior to IS900 Taqman qPCR next day), so in this scenario the manual PhMS-qPCR assay is no longer a one-day test.

Our recently developed PhMS-qPCR assay for viable MAP in milk was demonstrated to have greater MAP infection detection capability than the widely used milk-ELISA method. The findings of this study clearly demonstrate that the novel PhMS-qPCR assay could be a useful milk surveillance tool for dairy processors, as it provides information on the MAP infection status of supplying dairy herds and individual cows within the herds, as well as an indication of the numbers of viable MAP present. For milk monitoring purposes, as part of Johne's disease control programs or for milk quality assurance purposes, for example, PhMS-qPCR assay results would be more meaningful than milk-ELISA results because viable MAP cells (the infectious agent) are being detected and not simply antibodies to MAP.

REFERENCES

Alinovi, C., M. Ward, T. Lin, and C. Wu. 2009. Sample handling substantially affects Johne's ELISA. Prev. Vet. Med. 90:278-283. https://doi.org/10.1016/j.prevetmed.2009.04.004.

Animal Health and Welfare Northern Ireland (2014) A Guide to Johne's Disease for Northern Ireland Farmers and Vets. Online: http://www.animalhealthni.com/Johnes %20Brochure %20A4.pdf last accessed 17 Aug. 2020.

Barkema, H. W., J. W. Hesselink, S. L. B. McKenna, G. Benedictus, and H. Groenendaal. 2010. Global prevalence and economics of infection with *Mycobacterium avium* subsp. *paratuberculosis* in ruminants. In: Behr, M. A., Collins, D., editors. *Paratuberculosis*: Organism, Disease, Control. Wallingford, UK: CAB International, pp. 10-21.

Botsaris, G., M. Liapi, C. Kakogiannis, C. E. R. Dodd, and C. E. D. Rees. 2013. Detection of *Mycobacterium avium* subsp. *paratuberculosis* in bulk tank milk by combined phage-PCR assay: Evidence that plaque number is a good predictor of MAP. Int. J. Food Microbiol. 164:76-80. https://doi.org/10.1016/j.ijfoodmicro.2013.03.023.

Bradner, L., S. Robbe-Austerman, D. C. Beitz, and J. R. Stabel. 2013. Optimization of hexadecylpyridinium chloride decontamination for culture of *Mycobacterium avium* subsp. *paratuberculosis* from milk. J. Clin. Microbiol. 51(5):1575-1577. https://doi.org/10.1128/JCM.00333-13.

Butot, S., M. Ricchi, I. A. Sevilla, L. Michot, E. Molina, M. Tello, S. Russo, N. Arrigoni, J. M. Garrido, and D. Tomas. 2019. Estimation of the performance characteristics of analytical methods for *Mycobacterium avium* subsp. *paratuberculosis* detection in dairy products. Front. Microbiol. 10:509. https://doi.org/10.3389/fmicb.2019.00509.

Chiodini, R. J., W. M. Chamberlin, J. Sarosiek, and R. W. McCallum. 2012. Crohn's disease and the mycobacterioses: a quarter century later. Causation or simple association? Crit. Rev. Microbiol. 38:52-93. https://doi.org/10.3109/1040841X.2011.638273.

Dundee, L., I. R. Grant, H. J. Ball, and M. T. Rowe. 2001. Comparative evaluation of four protocols for the isolation of *Mycobacterium avium* ssp. *paratuberculosis* from milk. Lett. Appl. Microbiol. 33:173-177. https://doi.org/10.1046/j.472-765x.2001.00979.x.

Foddai, A., S. Strain, R. H. Whitlock, and I. R. Grant. 2011. Application of a novel peptide-mediated phage assay for the detection of viable *Mycobacterium avium* subsp. *paratuberculosis* to bovine bulk tank milk and feces samples. J. Clin. Microbiol. 49:2017-2019. https://doi.org/10.1128/JCM.00429-11.

Foddai, A. C. G., and I. R. Grant. 2015. An optimised milk testing protocol to ensure accurate enumeration of viable *Mycobacterium avium* subsp. *paratuberculosis* by the PMS-phage assay. Int. Dairy J. 51:16-23. https://doi.org/10.1016/j.idairyj.2015.07.004.

Foddai, A. C. G., and I. R. Grant. 2017. Sensitive and specific detection of *Mycobacterium avium* subsp. *paratuberculosis* in raw milk by the peptide-mediated magnetic separation (PMS)-phage assay. J. Appl. Microbiol. 122:1357-1367. https://doi.org/10.1111/jam.13425.

Foddai, A. C. G., and I. R. Grant. 2020. A novel one-day phage-based test for rapid detection and enumeration of viable *Mycobacterium avium* subsp. *paratuberculosis* in cows' milk. Appl. Microbiol. Biotechnol, submitted but not yet published.

Gamberale, F., G. Pietrella, M. Sala, P. Scaramella, S. Puccica, V. Antognetti, N. Arrigoni, M. Ricchi, and A. Cersini. 2019. Management of *Mycobacterium avium* subsp. *paratuberculosis* in dairy farms: Selection and evaluation of different DNA extraction methods from bovine and buffaloes milk and colostrum for the establishment of a safe colostrum farm bank. Microbiology Open 8:e875. https://doi.org/10.1002/mbo3.875.

Geraghty, T., D. A. Graham, P. Mullowney, and S. J. More. 2014. A review of bovine Johne's disease control activities in 6 endemically infected countries. Prev. Vet. Med. 116, 1-11. https://doi.org/10.1016/j.prevetmed.2014.06.003.

Gerrard, Z. E., B. M. C. Swift, G. Botsaris, R. S. Davidson, M. R. Hutchings, J. N. Huxley, and C. E. D. Rees. 2018. Survival of *Mycobacterium avium* subspecies *paratuberculosis* in retail pasteurised milk. Food Microbiol. 74:57-63. https://doi.org/10.1016/j.fm.2018.03.004.

Giacometti, F., A. Serraino, G. Finazzi, P. Daminelli, M. N. Losio, N., Arrigoni, S. Piva, D. Florio, R. Riu, and R. G. Zanoni. 2012. Sale of raw milk in Northern Italy: Food safety implications and comparison of different analytical methodologies for detection of foodborne pathogens. Foodborne Pathog. Dis. 9:293-297. https://doi.org/10.1089/fpd.2011.1052.

Khol, J. L., M. Wassertheurer, E. Sodoma, S. Revilla-Fernandez, J. Damoser, E. Österreicher, M. Dünser, U. Kleb, and W. Baumgartner. 2013. Long-term detection of *Mycobacterium avium* subspecies *paratuberculosis* in individual and bulk tank milk from a dairy herd with a low prevalence of Johne's disease. J. Dairy Sci. 96:3517-3524. https://doi.org/10.3168/jds.2012-6466.

Köhler, H., M. Ziller, F. Gierke, and K. Donat. 2017. Within-pool prevalence limits for the identification of *paratuberculosis* infected herds using antibody detection in pooled milk samples. Berliner and Münchener Tieräztliche Wochenschrift 130:34-41. https://doi.org/10.2376/0005-9366-16019.

Kostoulas, P., W. J. Browne, S. S. Nielsen, and L. Leontides. 2013. Bayesian mixture models for partially verified data: Age- and stage-specific discriminatory power of an antibody ELISA for *paratuberculosis*. Prev. Vet. Med. 111(3-4):200-205. https://doi.org/10.1016/j.prevetmed.2013.05.006.

Lavers, C. J., H. W. Barkema, I. R. Dohoo, S. L. McKenna, and G. P. Keefe. 2014. Evaluation of milk ELISA for detection of *Mycobacterium avium* subspecies *paratuberculosis* in dairy herds and association with within-herd prevalence. J. Dairy Sci. 97:299-309. https://doi.org/10.3168/jds.2013-7101.

Lund, B. M., G. W. Gould, and A. M. Rampling. 2002. Pasteurization of milk and the heat resistance of *Mycobacterium avium* subsp. *paratuberculosis*: A critical review of the data. Int. J. Food Microbiol. 77:135-145. https://doi.org/10.1016/S0168-1605(02)00057-0.

McAloon, C. G., M. L. Doherty, P. Whyte, L. O'Grady, S. J. More, L. L. M. Messam, M. Good, P. Mullowney, S. Strain, and M. J. Green. 2016. Bayesian estimation of prevalence of *paratuberculosis* in dairy herds enrolled in a voluntary Johne's Disease control program in Ireland. Prev. Vet. Med. 128:95-100. https://doi.org/10.1016/j.prevetmed.2016.04.014.

McAloon, C. G., S. Roche, C. Ritter, H. W. Barkema, P. Whyte, S. J. More, L. O'Grady, M. J. Green, and M. L. Doherty. 2019. A review of *paratuberculosis* in dairy herds—Part 2: On-farm control. Vet. J. 246:54-58. https://doi.org/10.1016/j.tvjl.2019.01.009.

Meyer, A., C. G. McAloon, J. A. Tratalos, S. J. More, L. R. Citer, D. A. Graham, and E. S. G. Sergeant. 2019. Modeling of alternative testing strategies to demonstrate freedom from *Mycobacterium avium* ssp. *paratuberculosis* infection in test-negative dairy herds in the Republic of Ireland. J. Dairy Sci. 102:1-16. https://doi.org/10.3168/jds.2018-14883.

Nielsen, S. S., and N. Toft. 2008. Ante mortem diagnosis of *paratuberculosis*: a review of accuracies of ELISA, interferon-gamma assay and faecal culture techniques. Vet. Microbiol. 129:217-235. https://doi.org/10.1016/j.vetmic.2007.12.011.

Nielsen, S. S., and N. Toft. 2014. Bulk tank milk ELISA for detection of antibodies to *Mycobacterium avium* ssp. *paratuberculosis*: Correlation between repeated tests and within-herd antibody-prevalence. Prev. Vet. Med. 113:96-102. https://doi.org/10.1016/j.prevetmed.2013.10.013.

O'Brien, L. M., C. G. McAloon, L. D. Stewart, S. A. J. Strain, and I. R. Grant. 2018. Diagnostic potential of the peptide-mediated magnetic separation (PMS)-phage assay and PMS-culture to detect *Mycobacterium avium* subsp. *paratuberculosis* in bovine milk samples. *Transbound. Emerg. Dis.* 65(3):719-726. https://doi.org/10.1111/tbed.12794.

Office International des Epizooties. 2019. Chapter 3.1.15. *Paratuberculosis* (Johne's Disease). In Manual of Diagnostic Tests and Vaccines for Terrestrial Animals 2019, pp. 544-559. Online: https://www.oie.int/fileadmin/Home/eng/Health standards/tahm/3.01.15 PARATB.pdf last accessed 17 Aug. 2020

Okura, H., S. S. Nielsen, and N. Toft. 2013. Modelling the effect of direct and indirect contamination of on-farm bulk tank milk with *Mycobacterium avium* subsp. *paratuberculosis*. Foodborne Pathog. Dis. 10:270-277. https://doi.org/10.1089/fpd.2012.1280.

Pesqueira, M. N., E. Yus, C. Factor, I. Mato, M. L. Sanjuán, C. Eiras, I. Arnaiz, and F. J. Diéguez. 2017. Short communication: Correlation between within-herd antibody prevalence and bulk tank milk antibody levels to *Mycobacterium avium* ssp. *paratuberculosis* using 2 commercial immunoassays. J. Dairy Sci. 100:7544-7548. https://doi.org/10.3168/jds.2017-12706.

Pozzato, N., J. Gwozdz, M. Gastaldelli, K. Capello, C Dal Ben, and E. Stefani. 2011. Evaluation of a rapid and inexpensive liquid culture system for the detection of *Mycobacterium avium* subsp. *paratuberculosis* in bovine feces. J. Microbiol. Meth. 84:413-417. https://doi.org/10.1016/j.mimet.2011.01.019.

Ricchi, M., R. Savi, L. Bolzoni, S. Pongolini, I. R. Grant, C. De Cicco, G. Cerutti, G. Cammi, C. A. Garbarino, and N. Arrigoni. 2016. Estimation of *Mycobacterium avium* subsp. *paratuberculosis* load in raw bulk tank milk in Emilia-Romagna Region (Italy) by qPCR. Microbiol. Open 5(4):551-559. https://doi.orq/10.1002/mbo3.350.

Robertson, R. E., O. Cerf, R. J. Condron, J. Donaghy, C. Heggum, and K. Jordan. 2017. Review of the controversy over whether or not *Mycobacterium avium* subsp. *paratuberculosis* poses a food safety risk with pasteurised dairy products. Int. Dairy J. 73:10-18. https://doi.org/10.1016/j.idairyj.2017.04.009.

Sergeant, E. S. G., C. G. McAloon, J. A. Tratalos, L. R. Citer, D. A. Graham, and S. J. More. 2019. Evaluation of national surveillance methods for detection of Irish dairy herds infected with *Mycobacterium avium* subsp. *paratuberculosis*. J. Dairy Sci. 102(3):2525-2538. https://doi.org/10.3168/jds.2018-15696.

Sidoti, F., G. Banche, S. Astegiano, V. Allizond, A. M. Cuffini, and M. Bergallo. 2011. Validation and standardization of IS900 and F57 real-time quantitative PCR assays for the specific detection and quantification of *Mycobacterium avium* subsp. *paratuberculosis*. Can. J. Microbiol. 57:347-354. https://doi.org/10.1139/w11-022.

Van Weering, H., G. van Schaik, A. der Meulen, M. Waal, P. Franken, and K. van Maanen. 2007. Diagnostic performance of the Pourquier ELISA for detection of antibodies against *Mycobacterium avium* subspecies *paratuberculosis* in individual milk and bulk milk samples of dairy herds. Vet. Microbiol. 125:49-58. https://doi.org/10.1016/j.vetmic.2007.05.010.

Waddell L. A., A. Rajic, K. D. C. Stark, and S. A. McEwen. 2015. The zoonotic potential of *Mycobacterium avium* ssp. *paratuberculosis*: a systematic review and meta-analyses of the evidence. Epid. Infect. 143(15):3135-3157. https://doi.org/10.1017/5095026881500076X.

Weber, M. F., A. G. Nielen, J. Velthuis, and H. J. W. van Roermund. 2008. Milk quality assurance for *paratuberculosis*: Simulation of within-herd infection dynamics and economics. Vet. Res. 39:12. https://doi.org/10.1051/vetres:2007050.

Whittington, R., K. Donat, M. F. Weber, D. Kelton, S. S. Nielsen, S. Eisenberg, N. Arrigoni, R. Juste, J. L. Sáez, N. Dhand, A, Santi, A. Michel, H. Barkema, P. Kralik, P. Kostoulas, L. Citer, F. Griffin, R. Barwell, M. A. S. Moreira, I. Slana, H. Köhler, S. V. Singh, H. S. Yoo, G.

55

Chávez-Gris, A. Goodridge, M. Ocepek, J. Garrido, K. Stevenson, M. Collins, B. Alonso, K. Cirone, F. Paolicchi, L. Gavey, M. T. Rahman, E. de Marchin, W. Van Praet, C. Bauman, G. Fecteau, S. McKenna, M. Salgado, J. Fernández-Silva, R. Dziedzinska, G. Echeverría, J. Seppanen, V. Thibault, V. Fridriksdottir, A. Derakhshandeh, M. Haghkhah, L. Ruocco, S. Kawaji, E. Momotani, C. Heuer, S. Norton, S. Cadmus, A. Agdestein, A. Kampen, J. Szteyn, J. Frossling, E. Schwan, G. Caldow, S. Strain, M. Carter, S. Wells, M. Munyeme, R. Wolf, R. Gurung, C. Verdugo, C. Fourichon, T. Yamamoto, S. Thapaliya, E. Di Labio, M. Ekgatat, A. Gil, A. Nuñez Alesandre, J. Piaggio,

56

A. Suanes, and J. H. de Waard. 2019. Control of *paratuberculosis*: who, why and how. A review of 48 countries. BMC Vet. Res. 15:198. https://doi.orq/10.1186/s12917-019-1943-4. Wilson, D. J., K. Rood, P. Biswas, and T. M. Byrem. 2010. Herd-level prevalence of Johne's disease in Utah and adjacent areas of the Intermountain West as detected by a bulk-tank milk surveillance project. J. Dairy Sci. 93(12):5792-5797. https://doi.org/10.3168/jds.2010-3481.

The invention is not limited to the embodiments described herein but can be amended or modified without departing from the scope of the present invention.

---

The invention claimed is:

1. A method for detecting desired *Mycobacterium* species in a sample, the method comprising the steps of:
   a) mixing lytic mycobacteriophage-coupled paramagnetic particles with the sample to form a reaction mixture under conditions suitable to allow the mycobacteriophages to bind to any mycobacteriophage-sensitive *Mycobacterium* species present in the sample;
   b) applying a magnetic field to the sample to collect, and separate, mycobacteriophage-coupled paramagnetic particles with bound desired *Mycobacterium* species;
   c) incubating a suspension of the separated paramagnetic particles with bound *Mycobacterium* species under conditions to allow the lytic mycobacteriophage to replicate inside viable *Mycobacterium* species cells and to lyse the viable *Mycobacterium* species cells;
   d) recovering, from the incubated suspension, nucleic acid of lysed *Mycobacterium* species; and
   e) analysing the nucleic acid released from the lysed *Mycobacterium* species to identify a signature nucleotide sequence that occurs in the desired *Mycobacterium* species;
   in which following step c), the incubated suspension is subjected to heat shock conditions of about 55° C. for about 1 minute to maximise release of nucleic acids from phage-lysed mycobacterial cells before centrifuging the incubated suspension to recover DNA of the lysed *Mycobacterium* species into a supernatant phase.

2. The method according to claim 1, in which, before step c), the collected paramagnetic particles with bound *Mycobacterium* species are washed to remove residual sample that is not paramagnetic particles with bound desired *Mycobacterium* species, and resuspended in a smaller volume.

3. A method according to claim 1, in which the step c) incubation is carried out to the endpoint of cell lysis.

4. A method according to claim 1, in which, in step c), the suspension of the separated paramagnetic particles with bound desired *Mycobacterium* species is incubated at 37° C. for 1 to 5 hours, to allow mycobacteriophage to replicate inside viable *Mycobacterium* species cells and to lyse the viable *Mycobacterium* species cells.

5. A method according to claim 1, in which the nucleic acid is DNA; and step d) comprises centrifuging the incubated suspension to recover, from the incubated suspension, the desired lysed *Mycobacterium* species DNA from a supernatant phase.

6. A method according to claim 1, in which step e) comprises probe-based qPCR.

7. A method according to claim 1, in which, following step c), the incubated suspension is subjected to heat shock conditions.

8. A method according to claim 7, in which the heat shock conditions comprise a temperature in the range of 40 to 70° C. for a period of at least 15 seconds to 1 minute to ensure maximal release of *Mycobacterium* species nucleic acid from cells lysed or weakened by the action of internal mycobacteriophages.

9. A method according to claim 1, in which the lytic mycobacteriophage is selected from Barnyard mycobacteriophage, Black Raspberry mycobacteriophage, Bxz2 mycobacteriophage, Che8 mycobacteriophage, PBI1 mycobacteriophage, Rosebush mycobacteriophage, Cooper mycobacteriophage, Wildcat mycobacteriophage, TM4 mycobacteriophage and D29 mycobacteriophage.

10. A method according to claim 1, in which the paramagnetic particles have a diameter in the range of 0.25 to 1.5 μm.

11. A method according to claim 10, in which the paramagnetic particles are tosylactivated beads having a diameter of 1 μm.

12. A method according to claim 1, in which about 5 to 25 lytic mycobacteriophages are coupled to each paramagnetic particle.

13. A method according to claim 1, in which about 0.5 to $3.5 \times 10^7$ D29 phage-coated beads are present in the step a) reaction mixture, when the sample is milk.

14. A method according to claim 1, in which the *Mycobacterium* species is *Mycobacterium avium* subsp. *paratuberculosis* for detecting and monitoring Johne's disease in ruminants.

15. A method according to claim 1, in which the *Mycobacterium* species is *Mycobacterium bovis* or *Mycobacterium tuberculosis*.

16. A method according to claim 15, for detecting and monitoring bovine tuberculosis in ruminants; optionally cattle; or tuberculosis in humans.

17. A method according to claim 1, in which the sample is selected from milk, faeces, blood, a blood or tissue sample, or a sample of food or animal feed.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Unknown
<220> FEATURE:
<223> OTHER INFORMATION: synthetic

<400> SEQUENCE: 1
ccggtaaggc cgaccatta                                            19

<210> SEQ ID NO 2
<211> LENGTH: 16
<212> TYPE: DNA
<213> ORGANISM: Unknown
<220> FEATURE:
<223> OTHER INFORMATION: Synthetic

<400> SEQUENCE: 2
acccgctgcg agagca                                              16

<210> SEQ ID NO 3
<211> LENGTH: 26
<212> TYPE: DNA
<213> ORGANISM: Unknown
<220> FEATURE:
<223> OTHER INFORMATION: Synthetic

<400> SEQUENCE: 3
catggttatt aacgacgacg cgcagc                                    26

<210> SEQ ID NO 4
<211> LENGTH: 21
<212> TYPE: DNA
<213> ORGANISM: Unknown
<220> FEATURE:
<223> OTHER INFORMATION: Synthetic

<400> SEQUENCE: 4
aactaagcgg atcgacaatt c                                         21

<210> SEQ ID NO 5
<211> LENGTH: 20
<212> TYPE: DNA
<213> ORGANISM: Unknown
<220> FEATURE:
<223> OTHER INFORMATION: Synthetic

<400> SEQUENCE: 5
tggtgtaccg aatgttgttg                                           20
```

-continued

```
<210> SEQ ID NO 6
<211> LENGTH: 22
<212> TYPE: DNA
<213> ORGANISM: Unknown
<220> FEATURE:
<223> OTHER INFORMATION: Synthetic

<400> SEQUENCE: 6
tgcaactcga acacacctgg ga                                          22
```